United States Patent
Amaravadi et al.

(10) Patent No.: US 11,639,335 B2
(45) Date of Patent: *May 2, 2023

(54) ASYMMETRIC BISAMINOQUINOLINES AND BISAMINOQUINOLINES WITH VARIED LINKERS AS AUTOPHAGY INHIBITORS FOR CANCER AND OTHER THERAPY

(71) Applicant: The Trustees of the University of Pennsylvania, Philadelphia, PA (US)

(72) Inventors: Ravi K. Amaravadi, Media, PA (US); Jeffrey D. Winkler, Wynnewood, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/229,012

(22) Filed: Apr. 13, 2021

(65) Prior Publication Data

US 2022/0064118 A1 Mar. 3, 2022

Related U.S. Application Data

(63) Continuation of application No. 16/201,117, filed on Nov. 27, 2018, now Pat. No. 11,001,558, which is a continuation of application No. 15/502,330, filed as application No. PCT/US2015/044282 on Aug. 7, 2015, now Pat. No. 10,221,140.

(60) Provisional application No. 62/034,897, filed on Aug. 8, 2014.

(51) Int. Cl.
| | |
|---|---|
| C07D 215/46 | (2006.01) |
| A61K 31/4706 | (2006.01) |
| A61K 31/4709 | (2006.01) |
| C07D 401/12 | (2006.01) |
| A61K 31/436 | (2006.01) |
| A61K 31/4375 | (2006.01) |
| A61K 31/4545 | (2006.01) |
| A61K 31/4745 | (2006.01) |
| A61K 31/4995 | (2006.01) |
| A61K 31/506 | (2006.01) |
| A61K 31/517 | (2006.01) |
| A61K 31/519 | (2006.01) |
| A61K 31/704 | (2006.01) |
| A61K 31/7056 | (2006.01) |

(52) U.S. Cl.
CPC .......... *C07D 215/46* (2013.01); *A61K 31/436* (2013.01); *A61K 31/4375* (2013.01); *A61K 31/4545* (2013.01); *A61K 31/4706* (2013.01); *A61K 31/4709* (2013.01); *A61K 31/4745* (2013.01); *A61K 31/4995* (2013.01); *A61K 31/506* (2013.01); *A61K 31/517* (2013.01); *A61K 31/519* (2013.01); *A61K 31/704* (2013.01); *A61K 31/7056* (2013.01); *C07D 401/12* (2013.01); *Y02A 50/30* (2018.01)

(58) Field of Classification Search
CPC .............. A61K 31/436; A61K 31/4375; A61K 31/4545; A61K 31/4706; A61K 31/4709; A61K 31/4745; A61K 31/4995; A61K 31/506; A61K 31/517; A61K 31/519; A61K 31/704; A61K 31/7056; Y02A 50/30
See application file for complete search history.

(56) References Cited

U.S. PATENT DOCUMENTS

| | | | |
|---|---|---|---|
| 2,816,893 | A | 12/1957 | Na |
| 5,756,517 | A | 5/1998 | Schohe-Loop et al. |
| 10,221,140 | B2 * | 3/2019 | Amaravadi ............. A61P 31/06 |
| 11,001,558 | B2 * | 5/2021 | Amaravadi ......... A61K 31/4706 |
| 2008/0269259 | A1 | 10/2008 | Thompson et al. |
| 2009/0275612 | A1 | 11/2009 | Higuchi et al. |
| 2010/0267704 | A1 | 10/2010 | Yuan et al. |
| 2012/0047551 | A1 | 2/2012 | Pattar et al. |
| 2014/0050696 | A1 | 2/2014 | Amaravadi et al. |
| 2016/0168099 | A1 | 6/2016 | Amaravadi et al. |
| 2017/0166530 | A1 | 6/2017 | Amaravadi et al. |
| 2018/0111904 | A1 | 4/2018 | Amaravadi et al. |
| 2018/0183897 | A1 | 6/2018 | Singhal |
| 2019/0222653 | A1 | 7/2019 | Dauneria et al. |

FOREIGN PATENT DOCUMENTS

| | | |
|---|---|---|
| DE | 1169948 B | 5/1964 |
| DE | 1296635 B | 9/1969 |
| GB | 0726568 A | 3/1955 |
| GB | 0999237 A | 7/1965 |
| WO | 93/07126 A1 | 4/1993 |
| WO | 97/48705 A1 | 12/1997 |
| WO | 01/00218 A1 | 1/2001 |
| WO | 01/02218 A1 | 1/2001 |
| WO | 2004/091485 A2 | 10/2004 |

(Continued)

OTHER PUBLICATIONS

Girault, J Med Chem, vol. 44, 1658-1605, 2001. (Year: 2001).*
Yin, Frontiers in Immunology, Jul. 2018, vol. 9, Article 1512, 1-11. (Year: 2018).
Zhang H, et al. Synthesis and in vitro cytotoxicity evaluation of 4-aminoquinoline derivatives. Biomedicine $ Pharmacotherapy, 2008;62:65-69.
Aguiar, PLoS ONE, 7(5), e37259, 1-9, 2012.
Amaravadi RK, et al. Autophagy inhibition enhances therapy-induced apoptosis in a Myc-induced model of lymphoma. J Clin Invest, 2007;117(2):326-336.
Amaravadi RK, et al. Principles and Current Strategies for Targeting Autophagy for Cancer Treatment. Clin Cancer Res, 2011;17:654-666.

(Continued)

*Primary Examiner* — D Margaret M Seaman
(74) *Attorney, Agent, or Firm* — BakerHostetler

(57) ABSTRACT

The invention provides novel asymmetric and symmetric bisaminoquinolmes and related compounds, methods of treatment and syntheses. The novel compounds exhibit effective anticancer activity and are useful in the treatment of a variety of autophagy-related disorders.

30 Claims, 21 Drawing Sheets

(56) References Cited

FOREIGN PATENT DOCUMENTS

| | | |
|---|---|---|
| WO | 2007/097450 A1 | 8/2007 |
| WO | 2012/149186 A2 | 11/2012 |

OTHER PUBLICATIONS

Amaravadi RK, Thomson CB. The roles of therapy-induced autophagy and necrosis in cancer treatment. Clin Cancer Res, 2007;13(24)7271-7279.

Amaravadi RK. Autophagy-induced tumor dormancy in ovarian cancer. J Clin Invest, 2008;118(12):3837-3841.

Bergeron RJ, et al. Synthesis of N4-Acylated N1,N8-Big(acyl)spermidines: An Approach to the Synthesis of Siderophores. J. Org. Chem, 1980;45:1589-1592 Rerat V, et al. alphavbeta3 Integrin-targeting Arg-Gly-Asp (RGD) peptidomimetics.

Bernett, J Med Chem, 2007, 50, 2127-2136.

Burnett JC, et al. Novel small molecule inhibitors of botulinum neurotoxin A metalloprotease activity. Biochemical and Biophysical Research Communications, Academic Press Inc, 2003;310(1 ):84-93.
Cadwell K, et al. A key role for autophagy and the autophagy gene Atg1611 in mouse and human intestinal Paneth cells Nature, 2008;456:259-263.
Carew JS, et al. Targeting autophagy augments the anticancer activity of the histone deacetylase inhibitor SAHA to overcome Ber-Abl-mediated drug resistance. Blood, 2007;110:313-322.
Coppens, Essays BIochem, 2011, 51:127-136. (Year: 2011).
Database Registry, (Nov. 16, 1984), Database accession No. 91066-18-1, URL: STN, XP055398170.
Database Registry, (Aug. 22, 2004), Database accession No. 730910-76:-6, URL: STN, XP055398310.
Database Registry, (Aug. 27, 2004), Database accession No. 733728-23-9, URL: STN, XP055398307.
Database Registry, (Sep. 10, 2004), Database accession No. 742637-63-4, URL: STN, XP055398292.
Database Registry, (Nov. 25, 2004), Database accession No. 788758-30-5, URL: STN, XP055398282.
Database Registry, (Aug. 16, 2005), Database accession No. 860346-93-6, URL: STN, XP055398284.
Database Registry, (Jan. 2, 2005), Database accession No. 807289-03-8, URL: STN, XP055398288 Database Registry, (Jan. 2, 2005), Database accession No. 806635-82-5, URL: STN, XP055398291.
De et al., "Structure-Activity Relationships for Antiplasmodial Activity among 7-Substituted 4-Aminoquinolines", Journal of Medicinal Chemistry, vol. 41, No. 25, 1998, pp. 4918-4926.
Degenhardt K, et al. Autophagy promotes tumor cell survival and restricts necrosis, inflammation, and tumorigenesis. Cancer Cell, 2006;10:51-64.
Degtyarev M, et al. Akt inhibition promotes autophagy and sensitizes PTEN-null tumors to lysosomotropic agents. J Cell Biol, 2008;183(1):101-116.
Girault S. Antiplasmodial activity and cytotoxicity of bis-, tris-, and tetraquinolines with linear or cyclic amino linkers. Journal of Medicinal Chemistry, 2001;44(11):1658 1665.
Hermone, Chem Medical Chem, 2008, 3, 1905-1912.
Hu C, et al. A 4-aminoquinoline derivative that markedly sensitizes tumor cell killing by Akt inhibitors with a minimum cytotoxicity to non-cancer cells. Eur J Med Chem, 2010;45(2):705-709.
Jones S, Li X. Synthesis of chiral beta-amino acid derivatives by asymmetric hydrosilylation with, an imidazole derived organocatalyst Tetrahedron, 2012;68:5522-5532.
Klingenstein R, et al. Similar Structure-Activity Relationships of Quinoline Derivatives for Antiprion and Antimalarial Effects. Journal of Medicinal Chemistry, 2006;49(17):5300-5308.
Lu, J Biomedical Science, 2011, 18:8, 1-13.
Lum JJ; et al. Autophagy in metazoans: cell survival in the land of plenty, Nat Rev Mol Cell Biol, 2005;6(6):439-448.
Ma, et al. Measurements of tumor cell autophagy predict invasiveness, resistance to chemotherapy, and survival in melanoma. Clin Can Research, 2011;17(10):3478-3489.
Mahalingam D, et al. Combined autophagy and HDAC inhibition: A phase I safety, tolerability, phannacokinetic, and pharmacodynamic analysis of hydroxychloroquine in combination with the HDAC inhibitor vorinostat in patients with advanced solid tumors. Autophagy, 2014;10(8):1403-1414.
Margolis BJ, et al. Assembly of 4-aminoquinolines via palladium catalysis: a mild and convenient alternative to SNAr methodology. J Org Chem, 2007;72:2232-2235.
Marquez VB, et al. Binding to deoxyribonucleic acid and inhibition of ribonucleic acid polymerase by analogue of chloroquine. Journal of Medicinal Chemistry, 1974;17(8):856-862.
Mathew R, et al. Role of autophagy in cancer. Nature Reviews, 2007;7:961-967.
Mcafee Q, et al. Autophagy inhibitor Lys05 has single-agent antitumor activity and reproduces the phenotype of a genetic autophagy deficiency. Proc Nall Acad Aci USA, 2012;109:8253-8258.
Murakami N, et.al. Facilely accessible multidrug resistance modulator derived from sucrose. Bioorg Med Chem Lett, 2003;12:3267-3270.
Opsenica et al., "4-Amino-7-chloroquinolines: Probing Ligand Efficiency Provides Botulinum Neurotoxin Serotype A Light Chain Inhibitors with Significant Antiprotozoal Activity", Journal of Medicinal Chemistry, 56(14):5860-5871 (2013).
Rangwala R, et al. Combined MTOR and autophagy inhibition: Phasel trial of hydroxychloroquine and temsirolimus in patients with advanced solid tumors and melanoma. Autophagy, 2014;10(8):1391-1402.
Rangwala R, et al. Phase I trial of hydroxychloroquine with dose-intense temozolomide in patients with advanced solid tumors and melanoma. Autophagy, 2014;10(8);1369-1379.
Rebecca VW, et al. Inhibition of autophagy enhances the effects of the KT inhibitor MK-2206 when combined with paclitaxel and carboplatin in BRAF wild-type melanoma. Pigment Cell Melanoma Res, 2014;27(3):465-478.
Rerat V, et al. alphavbeta3 Integrin-targeting Arg-Gly-Asp (RGD) peptidomimetics containing oligoethylene glycol (OEG) spacers. J Med Chem, 2009;52:7029-7043.
Rosenfeld MR, et al. A phase I/II trial of hydroxychloroquine in conjunction with radiation therapy and concurrent and adjuvant temozolomide in patients with newly diagnosed glioblastoma multiforme. Autophagy, 2014;10(8):1359-1368.
Schlosser M, Cottet F. Silyl-Mediated Halogen/Halogen Displacement in Pyridines and Other Heterocycles. Eur J Org Chem, 2002:4181-4184.
Shrivastava A, et al. Designer peptides: learning from nature. Urr Pharm Des, 2009;15(6):675-681.
Sinha BK, et al. Synthesis and Antitumor Properties of Bis(quinaldine) Derivatives. Journal of Medicinal Chemistry, 1977;20(11):1528-1531.
Solomon VR, et al. Design and synthesis of chloroquine analogs with anti-breast cancer property. Eur J Med Chem, 2010;45:3916-3923.
Tanida I, et al. LC3 conjugation system in mammalian autophagy. Int J Biochem Cell Biol, 2004;36:2503-2518.
Thomas KD. Design, synthesis and antimicrobial activities of some newquinoline derivatives carrying 1,2,3-triazole moiety. Euro J Med Chem, 2010:3803.
Van Heerden Lezanne et al.; Synthesis and in vitro antimalarial activiy of a series of bisquinoline and bispyrrolo [1,2a]quinoxaline compounds. European Journal of Medicinal Chemistry 2012, 55, pp. 335-345.
Vance D, et al. Polyvalency: a promising strategy for drug design. Biotechnol Bioeng, 2008;101:429-434.
Vennerstrom J, et al. Bisquinolines. 2. Antimalarial N,N-Bis(7-chloro-quinolin-4-yl) heteroalkanediamines. Antimalarial Bisquinolines, 1998;41:4360-4364.
Adams A, et al. Differences between central and peripheral rat alpha-adrenoceptors revealed using binuclear ligands European Journal of Pharmacology, 1986;127(1):27-35.

(56) References Cited

OTHER PUBLICATIONS

Adams A, et al. Interaction of DNA-intercalating antitumor agents with adrenoceptors. Mol Pharmacol, 1985;27:480-491.
Bailey DM, et al. Bispyridinamines: a new class of topical antimicrobial agents as inhibitors of dental plaque. J Med. Chem, 1984;27:1457-1464.
Chen JQ, et al. Bis-Quinolinium Cyclophanes: 8,14-Diaza-1, 7(1,4)-diquinolinacyclotetrad ecaphane (UCL 1848), a Highly Potent and Selective, Nonpeptidic Blocker of the Apamin-Sensitive Ca 2+ -Activated K+ Channel. Journal of Medicinal Chemistry, 2000;43(19):3478-3481.
Elslager EF, et al. Synthetic Amebicides. VIII. 7,7'-[lminobis(alkyleneimino) [bis[benz[c]acridines] and Congeneric 9-Aminoacridines, 12-Aminobenz[a] acridines, [2-Aminobenz[b] acridines, and 4-Aminoquinolines. Journal of Heterocyclic Chemistry, 1968;5(5):599-607.
Fan HY, et al. Dual-site binding of bivalent 4-aminopyridine- and 4-aminoquinoline-based AChE inhibitors: contribution of the hydrophobic alkylene tether to monomer and dimer affinities. Bioorganic & Medicinal Chemistry, 1999;7 (11):2569-2575.
Fan QW, et al. Akt and autophagy cooperate to promote survival of drug-resistant glioma. Sci Signal, 2010;3:ra81.
Ferguson LR, et al. The mutagenic effects of diacridines and diquinolines in microbial systems. Mutation Research, 1990;232(2):337-343.
Galanakis D, et al. Bis-quinolinium cyclophanes: toward a pharmacophore model for the blockade of apamin-sensitive SKCa channels in sympathetic neurons. Bioorganic & Medicinal Chemistry Letters, 2004;14(16):4231-4235.
Galanakis D, et al. Synthesis and Quantitative Structure-Activity Relationship of a Novel Series of Small Conductance Ca 2+ -Activated K+ Channel Blockers Related to Dequalinium. Journal of Medicinal Chemistry, 1996;39 (2):359-370.
Gourdie TA, et al. DNA-directed alkylating agents. 1. Structure-activity relationships for acridine-linked aniline mustards: consequences of varying the reactivity of the mustard J Med Chem, 1990;33:1177-1186.
Kaschula CH, et al. Structure-activity relationships in 4-aminoquinoline antiplasmodials. The role of the group at the 7-position. J Med Chem, 2002;45:3531-3539.
Kaur, K., et al., "Amino acid, dipeptide and pseudodipeptide conjugates of ring-substituted 8-aminoquinolines: synthesis and evaluation of anti-infective, β-haematin inhibition and cytotoxic activities," European Journal of Medicinal Chemistry, vol. 52, Jun. 2012, pp. 230-241.
Lee WW, et al. Synthesis of Mustards from Putrescine, Cadaverine, and 1,3-Diaminopropane. J Med Chem, 1963;6:567-569.
Madapa, S., et al., "Search for new pharmacophores for antimalarial activity. Part I: synthesis and antimalarial activity of new 2-methyl-6-ureido-4-quinolinamides," European Journal of Medicinal Chemistry, vol. 17, No. 1, Jan. 2009, pp. 203-221.
Pankiv S, et al. p62/SQSTM1 binds directly to Atg8/LC3 to facilitate degradation of ubiquitinated protein aggregtes by autophagy. J Biol Chem, 2007;282:24131-24145.
Rosenfield MR GS, et al. Pharmacokinetic analysis and pharmacodynamic evidence of autophagy inhibition in patients with newly diagnosed glioblastoma treated on a phase I trial of hydroxychloroquine in combination with adjuvant temozolomide and radiation (ABTC 0603). J Clin Oncol, 2010;28:Abstract #3086.
Saleem A, et al. Effect of dual inhibition of apoptosis and autophagy in prostate cancer. Prostate, 2012;72:1374-1381.
Singh A. Studies on Antibacterial Agents. III. Synthesis of N, N'-Bis (4-quinolyl-, 4-quinaldinyl-, 4-quinazolinyl-, or 9-acridinyl) polymethylenediamines and Their Sulfonamides. Chemical and Pharmaceutical Bulletin, 1975, 23(8): 1869-1871.
Singh S. Characterization of Simian Malarial Parasite (Plasmodium knowlesi)-induced Putrescine Transport in Rhesus Monkey Erythrocytes. A Novel Putrescine Conjugate Arrests in Vitro Growth of Simian Malarial Parasite (Plasmodium knowlesi) and Cures Multidrug Resistant Murine Malaria (Plasmodium yoeli) Infec. Journal of Biological Chemistry, 1997;272(23):13506-13511.
Sotelo J, et al. Adding chloroquine to conventional treatment for glioblastome multiforme: a randomized, double-blind, placebo-controlled trial. Ann Intern Med, 2006;144:337-343.
Srivastava S, et al. Synthesis of bisquinolines and their in vitro ability to produce methemoglobin in canine hemolysate, Bioorganic & Medicinal Chemistry Letters, 1999;9(5):653-658.
Ukani R, et al. Potent adjuvantic activity of CCR1-agonistic-quinoline. Bioorganic & Medicinal Chemistry Letters, 2011;22(1):293-295.
Vennerstrom JL. Bisquinolines. 1.,N,N-BIS(7-Chloroquinolin-4-YL)Alkanediamines with Potential Against Chloroquine-Resistant Malaria. Journal of Medicinal Chemistry, 1992;35(11):2129-2134.
Vicker N, et al. Novel angular benzophenazines: dual topoisomerase I and topoisomerase II inhibitors as potential anticancer agents. J Med Chem, 2002;45:721-739.
Yang S, et al. Pancreatic cancers require autophagy for tumor growth. Genes Dev, 2011;25:717-729.

\* cited by examiner

A

| Activities of selected dimeric CQs (A375P 72 hr alamar blue viability 384 well) | |
|---|---|
| Dimeric CQ | Free Base IC$_{50}$ (nm) |
| Lys13 | 1684 |
| Lys01/05 | 1391 |
| Lys36 | 524 |
| Lys37 | 1607 |
| Lys34 | 347 |
| Lys35 | 407 |
| Lys21 | 492 |
| Lys26 | 517 |
| Lys39 | 739 |
| Lys40 | 1379 |
| Lys72/73 | 846 |
| Lys74/75 | 465 |

B

FIGURE 2
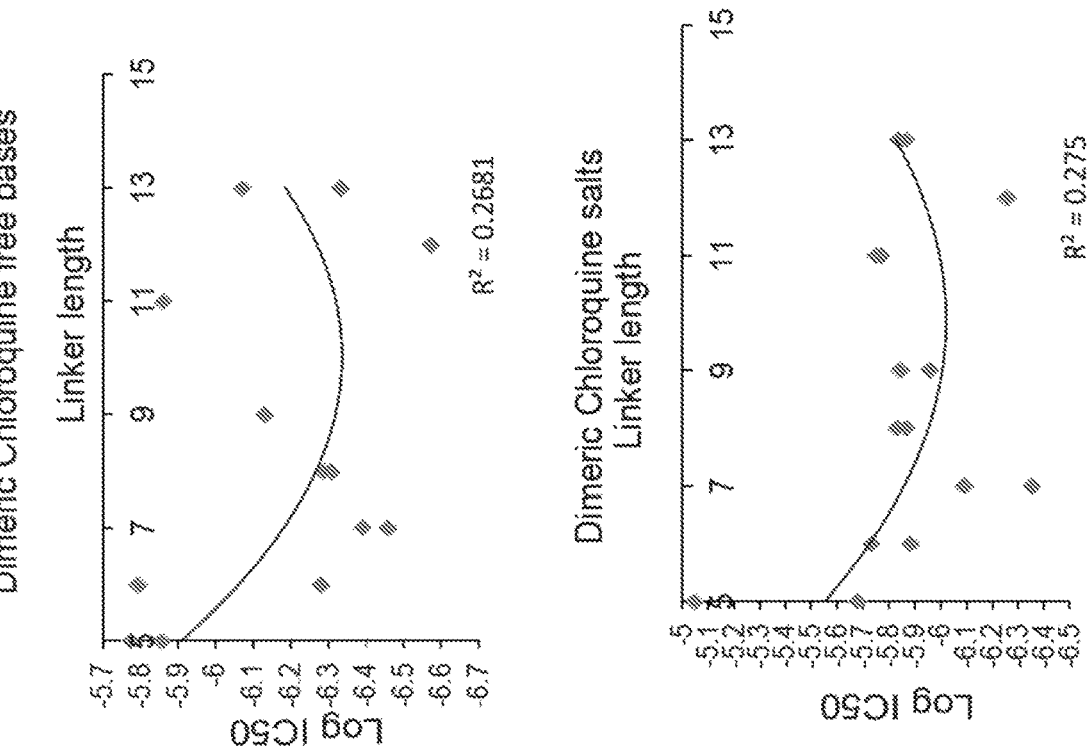
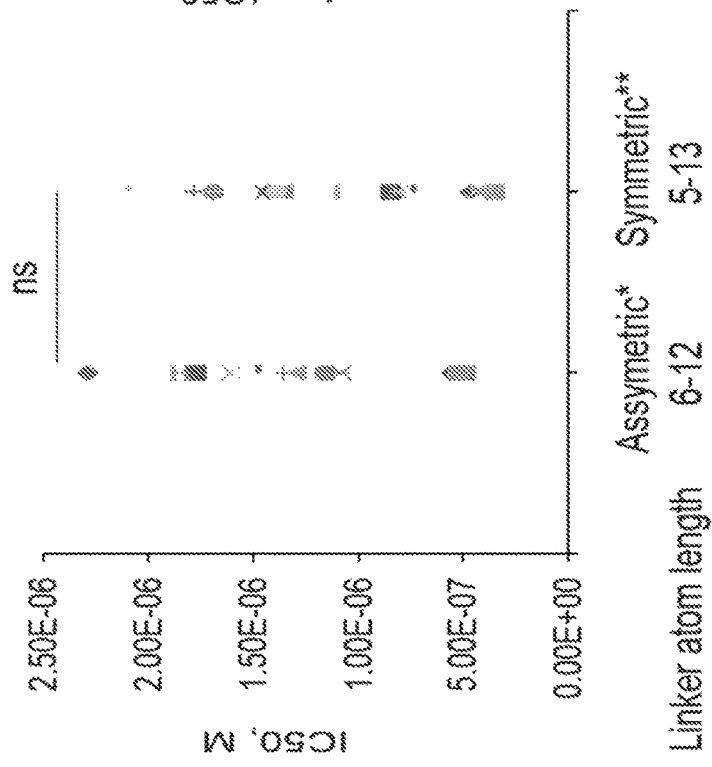

FIGURE 3
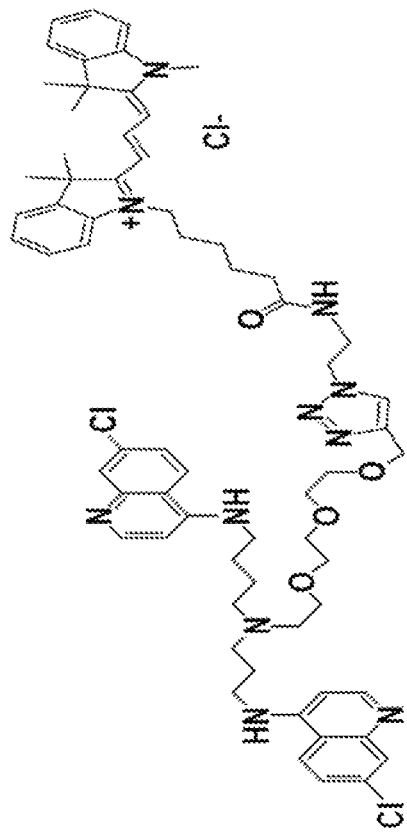
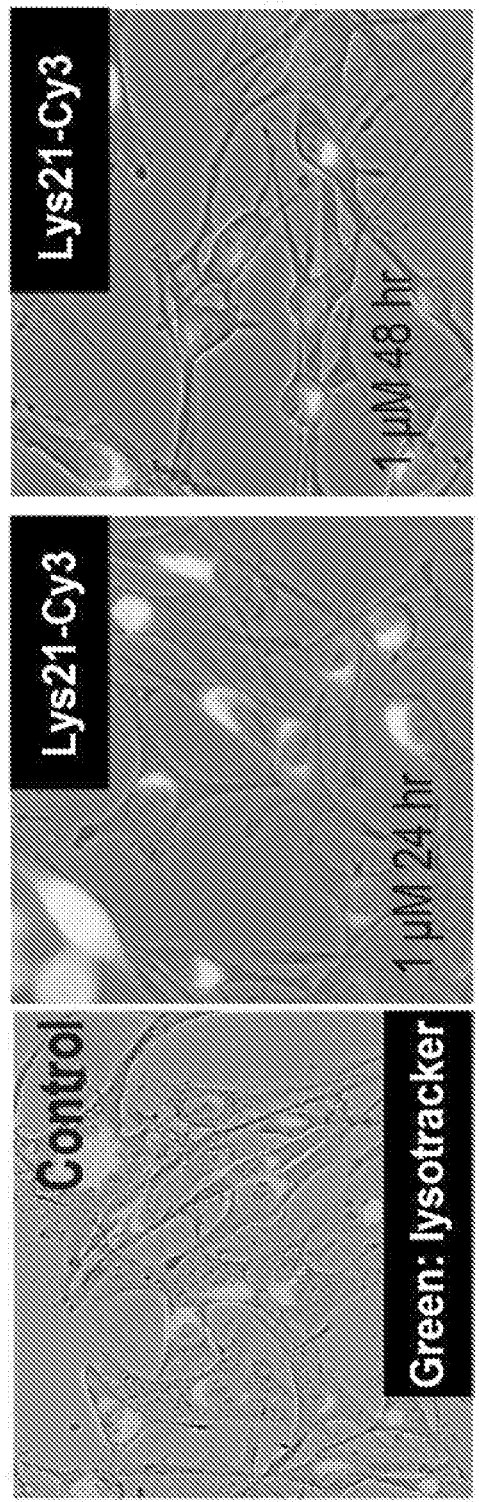

FIGURE 9
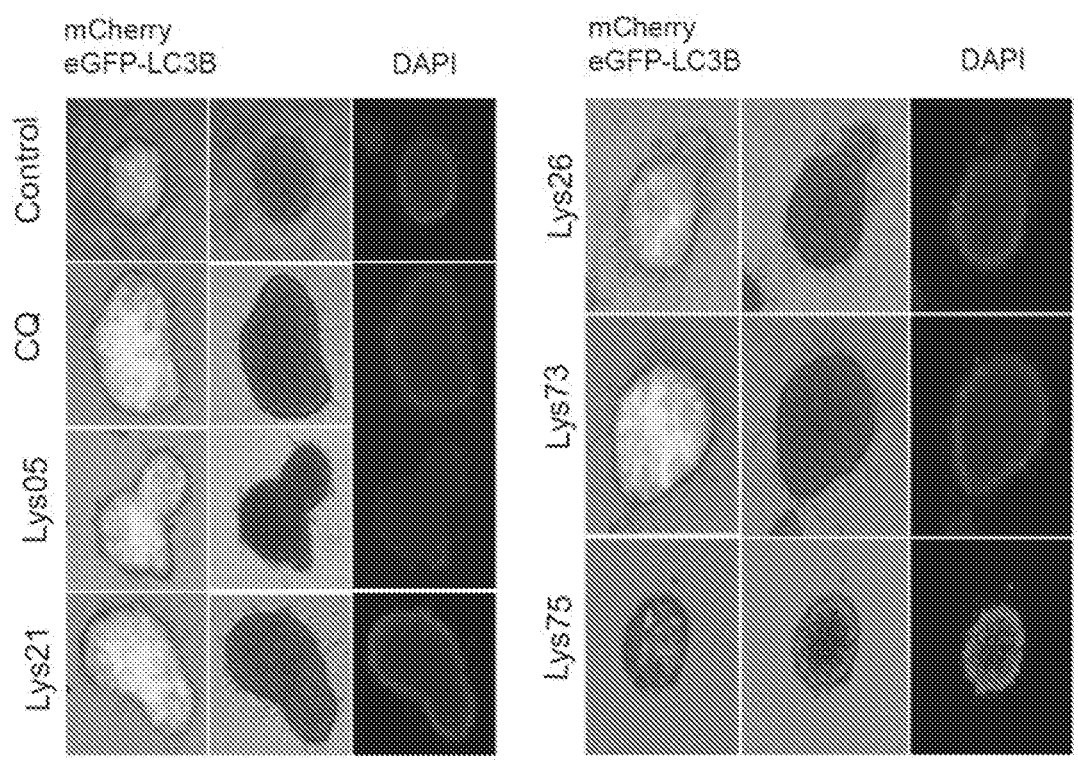
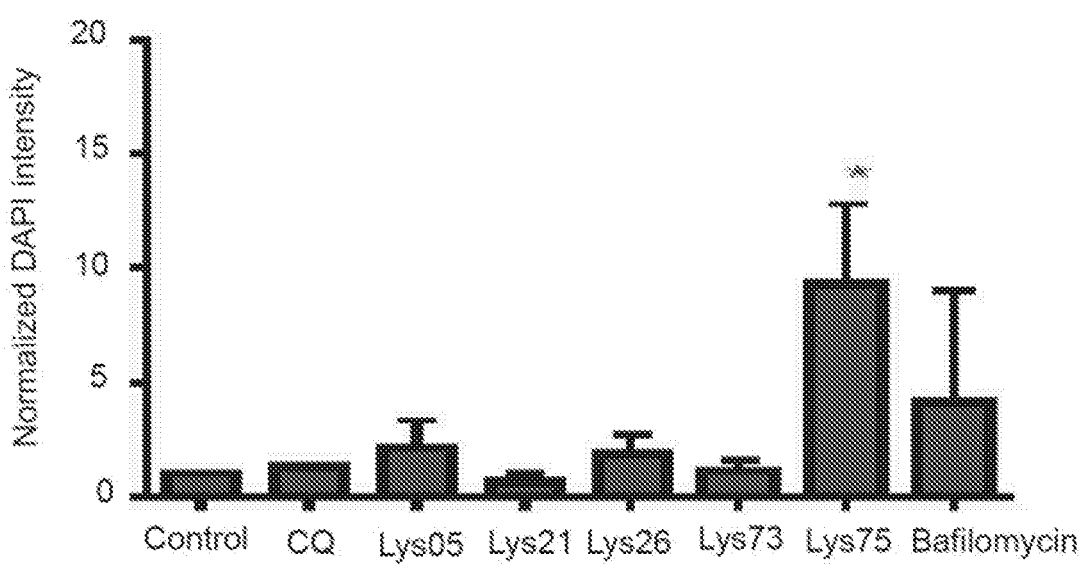

FIGURE 10

| Table 1. Lys01 derivatives IC50 A375P 72 hr 384 well alamar blue | | | | | |
|---|---|---|---|---|---|
| Compound | Type | Central nitrogen | Symmetric? | Linker carbon length | LogIC50 |
| -6.9≤Log IC50 ≤-6.0 | | | | | |
| Lys25 | FB | SP | SP | 12 | -6.57426 |
| Lys34 | FB | U | N | 7 | -6.45923 |
| Lys28 | FB | SP | SP | 12 | -6.43947 |
| Lys35 | FB | M | N | 7 | -6.39022 |
| Lys34 | salt | U | N | 7 | -6.35 |
| Lys74 | FB | M | N | 13 | -6.33224 |
| Lys21 | FB | U | Y | 8 | -6.30845 |
| Lys26 | FB | M | Y | 8 | -6.28629 |
| Lys36 | FB | U | Y | 6 | -6.28066 |
| Lys25 | salt | M | Y | 12 | -6.26 |
| Lys39 | FB | M | N | 9 | -6.13153 |
| Lys35 | salt | M | N | 7 | -6.09 |
| Lys72 | FB | U | N | 13 | -6.07244 |
| Lys20 | FB | U | SP | 12 | -6.05847 |
| Lys11 | FB | | | | -6.0466 |
| Lys29 | FB | X | N | 7 | -6.04421 |
| -5.9≤Log IC50 ≤-5.0 | | | | | |
| Lys22 | FB | X | N | 2 | -5.97858 |
| Lys32 | FB | X | Y | 8 | -5.96431 |
| Lys38 | salt | U | N | 9 | -5.96 |
| Lys31 | FB | X | Y | 8 | -5.93414 |
| Lys36 | salt | U | Y | 6 | -5.89 |
| Lys75 | salt | M | N | 13 | -5.87 |
| Lys26 | salt | M | Y | 8 | -5.87 |
| Lys40 | FB | U | N | 11 | -5.86048 |
| Lys1 | FB | M | N | 5 | -5.85669 |
| Lys39 | salt | M | N | 9 | -5.84 |
| Lys73 | salt | U | N | 13 | -5.84 |
| Lys21 | salt | U | Y | 8 | -5.83 |
| Lys22 | salt | X | N | 2 | -5.83 |
| Lys37 | FB | M | Y | 6 | -5.79393 |
| Spermidine | FB | U | | 8 | -5.78919 |
| Lys30 | FB | SP | N | 10 | -5.78198 |
| Lys13 | FB | U | N | 5 | -5.77361 |
| Lys40 | salt | U | N | 11 | -5.77 |
| Lys28 | salt | X | Y | 12 | -5.75 |
| Lys41 | salt | M | N | 11 | -5.75 |
| Lys37 | salt | M | Y | 6 | -5.73 |
| Lys31 | salt | X | Y | 8 | -5.73 |
| Lys29 | salt | X | N | 7 | -5.73 |
| Lys33 | salt | X | SP | 12 | -5.72 |

FIGURE 10 (cont.)

| | | | | | |
|---|---|---|---|---|---|
| QC | salt | | | | -5.71 |
| Lys30 | salt | X | SP | 12 | -5.71 |
| HCQ | FB | | | | -5.68908 |
| Lys05 | salt | M | N | 5 | -5.68 |
| Lys23 | FB | X | N | 2 | -5.66902 |
| Lys32 | salt | X | Y | 8 | -5.64 |
| Lys09 | FB | M | | 5 | -5.48584 |
| Lys33 | FB | SP | N | 10 | -5.48236 |
| Lys19 | FB | O | N | 11 | -5.45537 |
| Lys08 | FB | M | N | 5 | -5.44391 |
| Lys04 | FB | X | N | 8 | -5.43271 |
| Lys83 | salt | X | N | 9 | -5.43 |
| Lys14 | FB | X | O | 5 | -5.35493 |
| Lys23 | salt | X | N | 2 | -5.28 |
| Lyso-12 | FB | X | O | X | -5.27923 |
| Lys08 | salt | M | N | 5 | -5.23 |
| Lys7 | FB | M | N | 5 | -5.21486 |
| Lys16 | FB | X | O | X | -5.18723 |
| Lys20 | salt | U | SP | 12 | -5.18 |
| Lys19 | salt | O | O | 11 | -5.15 |
| Primaquine | salt | | | | -5.14 |
| Lys24 | FB | X | O | 2 | -5.13192 |
| Lys14 | salt | X | O | 5 | -5.12 |
| Lys04 | salt | X | N | 8 | -5.10 |
| Lys12 | salt | X | NA | X | -5.09 |
| Lys13 | salt | U | N | 5 | -5.05 |
| Lys18 | salt | X | X | X | -5.02 |
| -4.9≤Log IC50 | | | | | |
| Lys09 | salt | M | N | 5 | -4.95 |
| Lys15 | FB | X | O | X | -4.89199 |
| Lys07 | salt | M | N | 5 | -4.82 |
| Lys15 | salt | X | X | X | -4.77 |
| Lys06 | salt | M | N | 5 | -4.71 |
| CQ | salt | | | | -4.70 |
| HCQ | salt | | | | -4.56 |
| Lys02 | salt | M | NA | X | -4.56 |
| Lys03 | salt | M | NA | 5 | -4.37 |
| Lys10 | salt | O | N | 5 | -3.99 |
| CQ | FB | | | | -3.78641 |
| Lys03 | FB | M | | 5 | inactive |
| | FB | | | | inactive |
| Spermine | FB | U | | 12 | inactive |
| primaquine | FB | | | | |
| FB: free base; SP: Spermine; Y: Yes; N: No; X: Other | | | | | |

FIGURE 11

Table 2: Compounds

| Compound Number | IUPAC Name |
|---|---|
| Lys01 | N1-(7-chloroquinolin-4-yl)-N2-(2-((7-chloroquinolin-4-yl)amino)ethyl)-N2-methylethane-1,2-diamine |
| Lys02 | N1-(2-aminoethyl)-N2-(7-chloroquinolin-4-yl)-N1-methylethane-1,2-diamine |
| Lys03 | N1-(7-methoxyquinolin-4-yl)-N2-(2-((7-methoxyquinolin-4-yl)amino)ethyl)-N2-methylethane-1,2-diamine |
| Lys04 | N,N'-((ethane-1,2-diylbis(oxy))bis(ethane-2,1-diyl))bis(7-chloroquinolin-4-amine) |
| Lys05 | N1-(7-chloroquinolin-4-yl)-N2-(2-((7-chloroquinolin-4-yl)amino)ethyl)-N2-methylethane-1,2-diamine trihydrochloride |
| Lys06 | N1-methyl-N2-(quinolin-4-yl)-N1-(2-(quinolin-4-ylamino)ethyl)ethane-1,2-diamine |
| Lys07 | N1-(7-fluoroquinolin-4-yl)-N2-(2-((7-fluoroquinolin-4-yl)amino)ethyl)-N2-methylethane-1,2-diamine |
| Lys08 | N1-methyl-N2-(7-(trifluoromethyl)quinolin-4-yl)-N1-(2-((7-(trifluoromethyl)quinolin-4-yl)amino)ethyl)ethane-1,2-diamine |
| Lys09 | N1-methyl-N2-(7-nitroquinolin-4-yl)-N1-(2-((7-nitroquinolin-4-yl)amino)ethyl)ethane-1,2-diamine |
| Lys10 | N,N'-((methylazanediyl)bis(ethane-2,1-diyl))bis(N-(7-chloroquinolin-4-yl)acetamide) |
| Lys11 | N,N'-(oxybis(ethane-2,1-diyl))bis(7-chloroquinolin-4-amine) |
| Lys12 | N1-(7-chloroquinolin-4-yl)-N2,N2-bis(2-((7-chloroquinolin-4-yl)amino)ethyl)ethane-1,2-diamine |
| Lys13 | N1-(7-chloroquinolin-4-yl)-N2-(2-((7-chloroquinolin-4-yl)amino)ethyl)ethane-1,2-diamine |
| Lys14 | N1-(7-chloroquinolin-4-yl)-N2-(2-((7-chloroquinolin-4-yl)amino)ethyl)-N2-(prop-2-yn-1-yl)ethane-1,2-diamine |
| Lys15 | N1-(2-aminoethyl)-N2-(7-chloroquinolin-4-yl)-N1-(2-((7-chloroquinolin-4-yl)amino)ethyl)ethane-1,2-diamine |
| Lys16 | N1,N1-bis(2-aminoethyl)-N2-(7-chloroquinolin-4-yl)ethane-1,2-diamine |
| Lys17 | N1,N1-bis(2-((7-chloroquinolin-4-yl)amino)ethyl)-N2,N2-diethylethane-1,2-diamine |
| Lys18 | N1-(2-((7-chloroquinolin-4-yl)amino)ethyl)-N1-(2-(diethylamino)ethyl)-N2,N2-diethylethane-1,2-diamine |

FIGURE 11 (cont.)

| Lys19 | N,N'-(((oxybis(ethane-2,1-diyl))bis(oxy))bis(ethane-2,1-diyl))bis(7-chloroquinolin-4-amine) |
|---|---|
| Lys20 | N1,N1'-(butane-1,4-diyl)bis(N3-(7-chloroquinolin-4-yl)propane-1,3-diamine) |
| Lys21 | N1-(7-chloroquinolin-4-yl)-N4-(3-((7-chloroquinolin-4-yl)amino)propyl)butane-1,4-diamine |
| Lys22 | N1,N2-bis(7-chloroquinolin-4-yl)ethane-1,2-diamine |
| Lys23 | (1R,2R)-N1,N2-bis(7-chloroquinolin-4-yl)cyclohexane-1,2-diamine |
| Lys24 | 2-((7-chloroquinolin-4-yl)amino)ethan-1-ol |
| Lys25 | N1,N1'-(butane-1,4-diyl)bis(N3-(7-chloroquinolin-4-yl)-N1-methylpropane-1,3-diamine) |
| Lys26 | N1-(7-chloroquinolin-4-yl)-N4-(3-((7-chloroquinolin-4-yl)amino)propyl)-N4-methylbutane-1,4-diamine |
| Lys27 | N1,N9-bis(6-methoxy-2-methylquinolin-4-yl)nonane-1,9-diamine |
| Lys28 | N1,N1'-(butane-1,4-diyl)bis(N1-benzyl-N3-(7-chloroquinolin-4-yl)propane-1,3-diamine) |
| Lys29 | N1-benzyl-N4-(7-chloroquinolin-4-yl)-N1-(3-((7-chloroquinolin-4-yl)amino)propyl)butane-1,4-diamine |
| Lys30 | N,N'-(butane-1,4-diyl)bis(N-(3-((7-chloroquinolin-4-yl)amino)propyl)benzamide) |
| Lys31 | N-(4-((7-chloroquinolin-4-yl)amino)butyl)-N-(3-((7-chloroquinolin-4-yl)amino)propyl)benzamide |
| Lys32 | N1-(7-chloroquinolin-4-yl)-N4,N4-bis(3-((7-chloroquinolin-4-yl)amino)propyl)butane-1,4-diamine |
| Lys33 | N1,N1'-(butane-1,4-diyl)bis(N3-(7-chloroquinolin-4-yl)-N1-(3-((7-chloroquinolin-4-yl)amino)propyl)propane-1,3-diamine) |
| Lys34 | N1-(7-chloroquinolin-4-yl)-N3-(3-((7-chloroquinolin-4-yl)amino)propyl)propane-1,3-diamine |
| Lys35 | N1-(7-chloroquinolin-4-yl)-N3-(3-((7-chloroquinolin-4-yl)amino)propyl)-N3-methylpropane-1,3-diamine |
| Lys36 | N1-(7-chloroquinolin-4-yl)-N3-(2-((7-chloroquinolin-4-yl)amino)ethyl)propane-1,3-diamine |
| Lys37 | N1-(7-chloroquinolin-4-yl)-N3-(2-((7-chloroquinolin-4-yl)amino)ethyl)-N3-methylpropane-1,3-diamine |
| Lys38 | N1-(7-chloroquinolin-4-yl)-N4-(4-((7-chloroquinolin-4-yl)amino)butyl)butane-1,4-diamine |
| Lys39 | N1-(7-chloroquinolin-4-yl)-N4-(4-((7-chloroquinolin-4-yl)amino)butyl)-N4-methylbutane-1,4-diamine |

FIGURE 11 (cont.)

| Lys40 | N1-(7-chloroquinolin-4-yl)-N5-{5-((7-chloroquinolin-4-yl)amino)pentyl}pentane-1,5-diamine |
|---|---|
| Lys41 | N1-(7-chloroquinolin-4-yl)-N5-{5-((7-chloroquinolin-4-yl)amino)pentyl}-N5-methylpentane-1,5-diamine |
| Lys28' | N1,N1'-(butane-1,4-diyl)bis(N1-benzyl-N3-(7-chloroquinolin-4-yl)propane-1,3-diamine) tetrahydrochloride |
| Lys29' | N1-benzyl-N4-(7-chloroquinolin-4-yl)-N1-{3-((7-chloroquinolin-4-yl)amino)propyl}butane-1,4-diamine trihydrochloride |
| Lys30' | N,N'-(butane-1,4-diyl)bis(N-{3-((7-chloroquinolin-4-yl)amino)propyl}benzamide) dihydrochloride |
| Lys31' | N-{4-((7-chloroquinolin-4-yl)amino)butyl}-N-{3-((7-chloroquinolin-4-yl)amino)propyl}benzamide dihydrochloride |
| Lys32' | N1-(7-chloroquinolin-4-yl)-N4,N4-bis(3-((7-chloroquinolin-4-yl)amino)propyl)butane-1,4-diamine tetrahydrochloride |
| Lys33' | N1,N1'-(butane-1,4-diyl)bis(N3-(7-chloroquinolin-4-yl)-N1-{3-((7-chloroquinolin-4-yl)amino)propyl}propane-1,3-diamine)pentahydrochloride |
| Lys34' | N1-(7-chloroquinolin-4-yl)-N3-{3-((7-chloroquinolin-4-yl)amino)propyl}propane-1,3-diamine trihydrochloride |
| Lys35' | N1-(7-chloroquinolin-4-yl)-N3-{3-((7-chloroquinolin-4-yl)amino)propyl}-N3-methylpropane-1,3-diamine trihydrochloride |
| Lys36' | N1-(7-chloroquinolin-4-yl)-N3-{2-((7-chloroquinolin-4-yl)amino)ethyl}propane-1,3-diamine trihydrochloride |
| Lys37' | N1-(7-chloroquinolin-4-yl)-N3-{2-((7-chloroquinolin-4-yl)amino)ethyl}-N3-methylpropane-1,3-diamine trihydrochloride |
| Lys38' | N1-(7-chloroquinolin-4-yl)-N4-{4-((7-chloroquinolin-4-yl)amino)butyl}butane-1,4-diamine trihydrochloride |
| Lys39' | N1-(7-chloroquinolin-4-yl)-N4-{4-((7-chloroquinolin-4-yl)amino)butyl}-N4-methylbutane-1,4-diamine trihydrochloride |
| Lys40' | N1-(7-chloroquinolin-4-yl)-N5-{5-((7-chloroquinolin-4-yl)amino)pentyl}pentane-1,5-diamine trihydrochloride |
| Lys41' | N1-(7-chloroquinolin-4-yl)-N5-{5-((7-chloroquinolin-4-yl)amino)pentyl}-N5-methylpentane-1,5-diamine trihydrochloride |
| Lys 72 | N1-(7-chloroquinolin-4-yl)-N6-{6-((7-chloroquinolin-4-yl)amino)hexyl}hexane-1,6-diamine |
| Lys 73 | N1-(7-chloroquinolin-4-yl)-N6-{6-((7-chloroquinolin-4-yl)amino)hexyl}hexane-1,6-diamine trihydrochloride |

FIGURE 11 (cont.)

| Lys 74 | N1-(7-chloroquinolin-4-yl)-N6-{6-((7-chloroquinolin-4-yl)amino)hexyl}-N6-methylhexane-1,6-diamine |
|---|---|
| Lys 75 | N1-(7-chloroquinolin-4-yl)-N6-{6-((7-chloroquinolin-4-yl)amino)hexyl}-N6-methylhexane-1,6-diamine trihydrochloride |
| Lys 86 | N1-(7-chloroquinolin-4-yl)-N7-{7-((7-chloroquinolin-4-yl)amino)heptyl}-heptane-1,7-diamine |
| Lys 87 | N1-(7-chloroquinolin-4-yl)-N7-{7-((7-chloroquinolin-4-yl)amino)heptyl}-N7-methylheptane-1,7-diamine |
| Lys 88 | N1-(7-chloroquinolin-4-yl)-N8-{8-((7-chloroquinolin-4-yl)amino)octyl}-octane-1,8-diamine |
| Lys 89 | N1-(7-chloroquinolin-4-yl)-N8-{8-((7-chloroquinolin-4-yl)amino)octyl}-N8-methyloctane-1,8-diamine |
| Lys 90 | N1-(7-chloroquinolin-4-yl)-N9-{9-((7-chloroquinolin-4-yl)amino)nonyl}-nonane-1,9-diamine |
| Lys 91 | N1-(7-chloroquinolin-4-yl)-N9-{9-((7-chloroquinolin-4-yl)amino)nonyl}-N8-methylnonane-1,9-diamine |
| Lys 92 | N1-(7-chloroquinolin-4-yl)-N10-{10-((7-chloroquinolin-4-yl)amino)decyl}-decane-1,10-diamine |
| Lys 93 | N1-(7-chloroquinolin-4-yl)-N10-{10-((7-chloroquinolin-4-yl)amino)decyl}-N10-methyldecane-1,10-diamine |
| Lys 94 | N1-(7-chloroquinolin-4-yl)-N11-{11-((7-chloroquinolin-4-yl)amino)undecyl}-undecane-1,11-diamine |
| Lys 95 | N1-(7-chloroquinolin-4-yl)-N11-{11-((7-chloroquinolin-4-yl)amino)undecyl}-N11-methylundecane-1,11-diamine |
| Lys 96 | N1-(7-chloroquinolin-4-yl)-N12-{12-((7-chloroquinolin-4-yl)amino)dodecyl}-dodecane-1,12-diamine |
| Lys 97 | N1-(7-chloroquinolin-4-yl)-N12-{12-((7-chloroquinolin-4-yl)amino)dodecyl}-N12-methyldodecane-1,12-diamine |

X = F, Cl, Br

Lys 34: R=H; m=n=1
Lys 35: R=Me; m=n=1
Lys 36: R=H; m=1; n=0
Lys 37: R=Me; m=1; n=0
Lys 38: R=H; m=n=2
Lys 39: R=Me; m=n=2
Lys 40: R=H; m=n=3
Lys 41: R=Me; m=n=3
Lys 72: R=H; m=n=4
Lys 73: Lys 72·3HCl (salt form)
Lys 74: R=Me; m=n=4
Lys 75: Lys 74·3HCl (salt form)

Lys 86: R=H; m=n=5
Lys 87: R=Me; m=n=5

Lys 88: R=H; m=n=6
Lys 89: R=Me; m=n=6

Lys 90: R=H; m=n=7
Lys 91: R=Me; m=n=7

Lys 92: R=H; m=n=8
Lys 93: R=Me; m=n=8

Lys 94: R=H; m=n=9
Lys 95: R=Me; m=n=9

Lys 96: R=H; m=n=10
Lys 97: R=Me; m=n=10

ASYMMETRIC BISAMINOQUINOLINES AND BISAMINOQUINOLINES WITH VARIED LINKERS AS AUTOPHAGY INHIBITORS FOR CANCER AND OTHER THERAPY

RELATED APPLICATIONS

This application is a continuation application of U.S. Ser. No. 16/261,117, filed Nov. 27, 2018, now U.S. Pat. No. 11,001,558, which is a continuation application of U.S. Ser. No. 15/502,330, filed Feb. 7, 2017, now U.S. Pat. No. 10,221,140, which is a National Stage Entry of International Patent Application PCT/US2015/044282, flied Aug. 7, 2015, which claims the benefit of priority of U.S. provisional application Ser. No. 62/034,897, filed Aug. 8, 2014, of identical title, the entireties of each of which are incorporated by reference herein.

GOVERNMENT INTEREST

This invention was made with government support under CA114046 awarded by the National Institute of Health. The government has certain rights in the invention.

FIELD OF THE INVENTION

The invention provides novel asymmetric and symmetric bisaminoquinolines and related compounds, methods of treatment and syntheses. The novel compounds exhibit unexpected anticancer activity and are useful in the treatment of a variety of autophagy-related disorders.

BACKGROUND AND DESCRIPTION OF THE INVENTION

Autophagy consists of the sequestration of organelles and proteins in autophagic vesicles (AV) and degradation of this cargo through lysosomal fusion (1). Autophagy allows tumor cells to survive metabolic and therapeutic stresses (2-5). Multiple publications indicate therapy-induced autophagy is a key resistance mechanism to many anti-cancer agents. Chloroquine (CQ) derivatives block autophagy by inhibiting the lysosome (3, 6, 7). Based on these findings, clinical trials combining cancer therapies with hydroxychloroquine (HCQ), (which is safer than CQ to dose escalate) have been launched. Preliminary results indicate these combinations have activity (8-13), but it is still unclear if this activity is consistently due to the addition of HCQ. High micromolar concentrations of HCQ are required to inhibit autophagy. While there is some pharmacodynamic evidence of autophagy inhibition with HCQ in cancer patients, it is inconsistent because adequate concentrations are not achieved in all patients. There is an unmet need to develop more potent inhibitors of autophagy. The design and synthesis of dimeric analogs of CQ, that exploit the thermodynamic advantages imparted by polyvalency (14, 15), has been a subject of intensive study for over 10 years (16-18). An early report by Vennerstrom (17) described the synthesis of heteroalkane-bridged bisquinolines as potential antimalarials, but none of the compounds had sufficient antimalarial activity to warrant further investigation. Subsequently, Sergheraert (16) reported that tetraquinolines, i.e., dimers of bisquinolines, afforded potent antimalarials, confirming the possibility that the application of the polyvalency strategy could afford increased potency, at least with respect to antimalarial activity.

More recently, Lee (19) has described the potentiation of AKT inhibitors by fluorinated quinoline analogs. Solomon (20) has reported the preparation of "repositioned" chloroquine dimers, based on the use of a piperazine connector. These results suggest that these chloroquine analogs could serve as bases for the development of a new group of effective cancer chemotherapeutics. We have examined the application of the strategy of polyvalency (14, 15) to the synthesis of novel autophagy inhibitors by preparing a dimeric chloroquine (Lys01, FIG. 11 or 12), from commercially available materials. We have recently reported a series of BAIs that potently inhibit autophagy and impair tumor growth in vivo (21). The structural motifs that are necessary for improved autophagy inhibition compared to CQ include the presence of two aminoquinoline rings and a triamine linker, as shown in the lead compound, 1 (Lys 01) which is a 10-fold more potent autophagy inhibitor than HCQ. Compared to HCQ, Lys 05, a water soluble salt of Lys01, more potently accumulates within and deacidifies the lysosome, resulting in impaired autophagy and tumor growth. At the highest dose administered, some mice developed Paneth cell dysfunction that resembles the intestinal phenotype of mice and humans with genetic defects in the autophagy gene ATG16L1(22), providing in vivo evidence that Lys05 targets autophagy. Unlike HCQ, significant single agent antitumor activity is observed without toxicity in mice bearing xenograft tumors treated with lower doses of Lys05, establishing the therapeutic potential of this compound in cancer. However, while Lys05 is 10-fold more potent than HCQ in in vitro autophagy assays, it is cytotoxic only at micromolar concentrations in most cancer cells.

In the present invention, we demonstrate the preparation and the unexpected biological activity of asymmetric bisaminoquinolines and related compounds via changing the linker length and/or disrupting the symmetry of the previously employed linkers. We describe unexpected increase in anti-cancer properties and capacity for autophagy inhibition of bivalent aminoquinolines when linker length is changed substantially and/or asymmetrically from Lys01.

SUMMARY OF THE INVENTION

Herein we demonstrate the preparation and the unexpected biological activity of asymmetric bis-4-aminoquinolines and related compounds by changing the linker. We describe the unexpected increase in anti-cancer properties of bivalent 4-aminoquinolines when linker length is changed substantially and asymmetrically from the parent Lys01 scaffold.

In one preferred embodiment, the invention provides a compound of Formula IA:

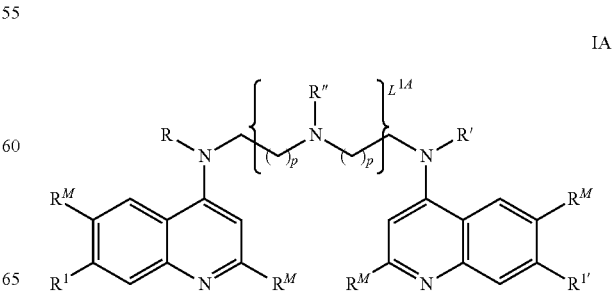

wherein $R^1$ and $R^{1'}$ are each independently H, F, Cl, Br, I, CN, $NO_2$, optionally substituted $C_1$-$C_6$ alkyl (when substituted, preferably substituted with 1 or 2 hydroxyl groups or 3-5 fluoro groups, preferably a $CF_3$ group), optionally substituted O—$C_1$-$C_6$ alkyl (preferably $OCH_3$), optionally substituted $C_2$-$C_7$ acyl (preferably acetyl), optionally substituted —(NH)-acyl, or optionally substituted $C_2$-$C_7$ ester (oxycarbonyl ester or carboxyester, preferably carboxyester) (each of the aforementioned groups, when substituted, is preferably substituted with one or two hydroxyl groups, one two or three halo groups or a methyl group)ss; R and R' are each independently H, a $C_1$-$C_6$ optionally substituted alkyl group, a $C_1$-$C_7$ (preferably $C_2$-$C_7$) optionally substituted acyl group a $C_2$-$C_7$ optionally substituted carboxy ester group (which forms a urethane group with the nitrogen atom to which R or R' is bonded);

R" is H, an amine protecting group (preferably benzoyl or benzyl), $Cy^1$ or $(C=O)_zG$, where $Cy^1$ is an optionally substituted cycloalkyl, aryl or heteroaryl group, G is an optionally substituted $C_0$-$C_{12}$ (preferably $C_1$-$C_8$, often $C_1$-$C_3$ alkyl) alkyl, alkene or alkynyl group (wherein optional substiuents include a $C_1$-$C_{12}$ (preferably $C_1$-$C_8$) alkyl, alkene or alkynyl group substituted by (N—$R^J$)—($C_1$-$C_8$ alkyl, alkene or alkynyl group)$_z$-$(Cy^2)_x$, where $R^J$ is H or a $C_1$-$C_8$ alkyl, alkene or alkynyl group, z is 0, 1, 2, 3, 4 or 5, x is 0 or 1 and $Cy^2$ is an optionally substituted aryl or heteroaryl group (most preferably benzyl or quinoline);

$R^M$ is independently at each occurrence H, F, Cl, Br, I, an optionally substituted $C_1$-$C_{12}$ (preferably $C_1$-$C_8$) alkyl, alkene, alkynyl or alkoxy group (preferably including a $CF_3$ group); Each p in linker group $L^{1A}$ is independently 1-10 (often 1, 2, 3, 4, 5, 6, 7 or 8 or more often 1, 2 or 3) and optionally (preferably) each p in a molecule is different;

and the pharmaceutically acceptable salts, enantiomers, diastereomers, solvates and polymorphs thereof, wherein the length of designated linker group $L^{1A}$ may vary, e.g. as illustrated in the compounds exemplified herein.

In another preferred embodiment, the invention provides a compound of Formula IB:

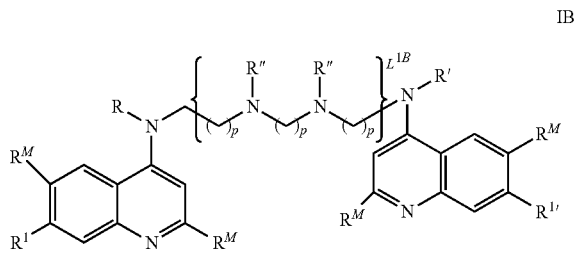

IB or a pharmaceutically acceptable salt, enantiomer, diastereomer, solvate or polymorph thereof, wherein the substituents are the same as defined for Formula IA; and p and p' in linker group $L^{1B}$ are each independently 1, 2, 3, 4, 5, 6, 7, 8, 9 or 10, often 1, 2, 3, 4, 5, or 6 and preferably, at least one of p or p' is different.

In another preferred embodiment, the invention provides a compound of Formula IC:

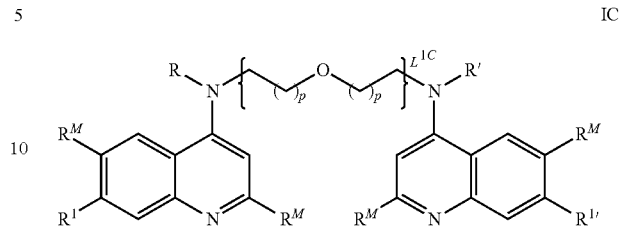

IC or a pharmaceutically acceptable salt, enantiomer, diastereomer, solvate or polymorph thereof, wherein the substituents are the same as defined for Formula IA above, and each p in linker group $L^{1C}$ is independently 1-10 (often 1, 2, 3, 4, 5, 6, 7 or 8 or more often 1, 2 or 3) and optionally (preferably) each p in a molecule is different In another preferred embodiment, the invention provides a compound of Formula ID:

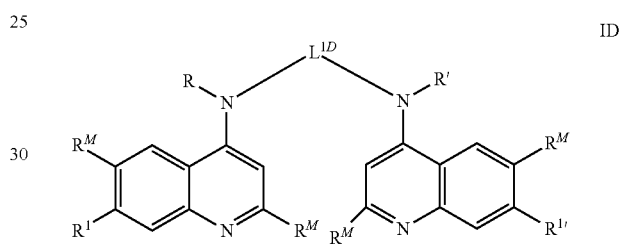

ID or a pharmaceutically acceptable salt, enantiomer, diastereomer, solvate or polymorph thereof, wherein the substituents are the same as defined for Formula IA above and linker group $L^{1D}$ is an optionally substituted alkylene group containing from 1-20, preferably 1, 2, 3, 4, 5, 6, 7, 8, 9, 10, 11, 12, 13, 14 or 15 methylene groups, wherein one or more methylene groups in linker group $L^{1D}$ is preferably substituted with one or two hydroxyl groups, one or two halo groups or one or two $C_1$-$C_3$ alkyl groups.

In still another embodiment, the present invention relates to compounds according to the chemical structure IE:

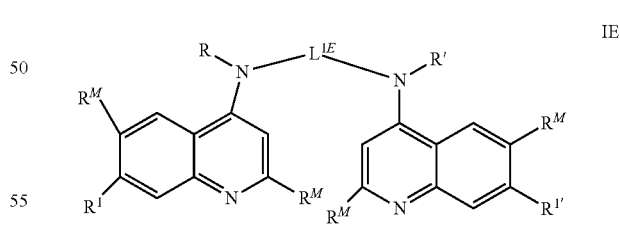

IE

Wherein $R^1$ and $R^{1'}$ are each independently H, halo (F, Cl, Br or I), CN, $NO_2$, optionally substituted $C_1$-$C_6$ alkyl (when substituted, preferably substituted with 1 or 2 hydroxyl groups or 3-5 fluoro groups), optionally substituted O—$C_1$-$C_6$ alkyl (preferably, $OCH_3$), optionally substituted $C_2$-$C_7$ acyl (preferably acetyl), optionally substituted —(NH)-acyl, or optionally substituted $C_2$-$C_7$ ester (oxycarbonyl ester or carboxyester, preferably carboxyester); $R^M$ is independently at each occurrence H, F, Cl, Br, I, an optionally substituted $C_1$-$C_{12}$ (preferably $C_1$-$C_8$) alkyl, alkene, alkynyl or alkoxy group (preferably including a $CF_3$ group); R and R' are each independently H, a $C_1$-$C_6$ optionally substituted alkyl group, a $C_1$-$C_7$ (preferably $C_2$-$C_7$) optionally substituted acyl group, a $C_2$-$C_7$ optionally substituted carboxy ester group (which forms a urethane group with the nitrogen atom to which R or R' is bonded);

Linker group $L^{1E}$ is a

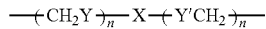

group or a

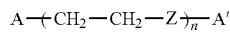

group (either A or A' may be bonded to either of the two amine groups in compound I) wherein at least one of the $CH_2$ groups in L is optionally substituted with an optionally substituted $C_1$-$C_6$ alkyl group including an optionally substituted cyclic alkyl group which, when substituted, are preferably substituted with one or two hydroxyl groups, one two or three halo groups (preferably Cl or F) or one or two $C_1$-$C_3$ alkyl groups (preferably methyl), or at least two methylene groups in linker group L (preferably two adjacent methylene groups) are substituted with alkylene groups to form an optionally substituted $C_3$-$C_8$ (preferably a $C_5$-$C_6$) cycloalkyl group (ring), which itself, when substituted, is preferably substituted with one or two hydroxyl groups, one two or three halo groups (preferably F or Cl) or one or two $C_1$-$C_3$ alkyl groups (preferably methyl), or linker group L is a (poly)ethylene glycol group having from 1 to 20 (preferably 2 to 15, 3 to 10 or 4, 5, 6, 7, 8, 9, or 10) ethylene glycol units, each (poly)ethylene glycol group being optionally substituted at one or both of its distal ends with an A group, or linker group L is a linear group containing from 1 to 5 non-contiguous amine groups N—R", each amine group being separated from an adjacent amine group by an alkylene group containing from 1, 2, 3, 4, 5, 6, 7, or 8 (preferably 2, 3, 4, 5 or 6) methylene groups or an ethylene glycol containing group having from 1 to 6 (preferably 2 to 6, 3 to 6 or 4, 5 or 6) ethylene glycol units;

X is absent, $(CH_2)_j$, O, S or N—R";

Y is absent, $CH_2$, O, $CH_2O$ or N—R" and Y' is absent $CH_2$, O, $OCH_2$ or N—R", with the proviso that when one or more of X, Y and Y' is present, each of X and Y, X and Y' or Y and Y', when present, forms a bond;

R" is H or an optionally substituted $C_1$-$C_6$ (preferably $C_1$-$C_3$) alkyl group or an amine protecting group (preferably H, Me, benzoyl or benzyl);

each j is independently 1, 2, 3, 4, 5 or 6 (preferably 1 or 2);

each n is independently 0, 1, 2, 3, 4, 5, 6, 7, 8, 9 or 10 with the proviso that when n is 0, X is $(CH_2)_j$, where j is at least 1 and at least one $CH_2$ group is optionally substituted, preferably with a $C_1$-$C_3$ alkyl group which itself is optionally substituted with one or two hydroxyl groups or one two or three halo groups;

A is absent, C=O or $(CH_2)_j$ and A' is C=O or $(CH_2)_3$ wherein at least one $CH_2$ group in A or A' is optionally substituted, preferably with a $C_1$-$C_3$ alkyl group which is itself optionally substituted, preferably with one or two hydroxyl groups or one, two or three halo groups;

Z is O or N—$R^Z$;

$R^Z$ is H or an optionally substituted $C_1$-$C_3$ alkyl group, or a pharmaceutically acceptable salt, enantiomer, diastereomer, solvent or polymorph thereof.

In certain preferred embodiments of the invention, at least one (preferably two) $R^M$ is other than H, especially when $R^1$ and $R^{1'}$ are H. In other preferred aspects of the invention, $R^1$ and $R^{1'}$ are each independently H, a halo group (most often Cl or F), a nitro group or a trifluoromethyl group, most often a chloro or fluoro group. R and R' are preferably each independently H or methyl, preferably H and L is preferably an alkylene group containing from 6 to 20 methylene groups (6, 7, 8, 9, 10, 11, 12, 13, 14, 15, 16, 17, 18, 19 or 20), a (poly)ethylene glycol group having from 1 to 20 (1, 2, 3, 4, 5, 6, 7, 8, 9, 10, 11, 12, 13, 14, 15, 16, 17, 18, 19 or 20, preferably 2 to 15, 3 to 10 or 4, 5, 6, 7, 8, 9, or 10) ethylene glycol units, each (poly)ethylene glycol group being optionally substituted at one or both of its distal ends with an A group, or L is a linear group containing from 1 to 5 non-contiguous amine groups N—R", each amine group being separated from an adjacent amine group by an alkylene group containing from 1, 2, 3, 4, 5, 6, 7, or 8 (preferably 2, 3 or 4) methylene groups or an ethylene glycol containing group having from 1 to 6 (preferably 2 to 6, 3 to 6 or 4, 5 or 6) ethylene glycol units. R" is preferably H, methyl or an amine protecting group (preferably a benzyl or benzoyl group which can be removed to introduce other groups on the amine group after deprotection).

In certain embodiments, one or more amine group of L is optionally substituted with one or two 7-substituted-4-quinolinyl group(s) wherein the amine binds to the 4-position of the quinolinyl group through an alkylene group and the 7-position of each quinolinyl group is optionally substituted, preferably with a $R^1$ and/or $R^{1'}$ group as broadly described for generic structure I above, or one or more amines of L is substituted with an alkyl group which itself is further optionally substituted with at least one hydroxyl group, an alkoxy group, an amine, a monoalkyl ($C_1$-$C_6$, preferably $C_1$-$C_3$) amine or a dialkyl ($C_1$-$C_6$, preferably $C_1$-$C_3$) amine wherein the amine or monoalkyl amine is optionally substituted on the amine position with one or two 7-substituted-quinolinyl group(s) wherein the amine binds to the 4-position of the quinolinyl group and the 7-position of each quinolinyl group is optionally substituted, preferably with $R^1$ and/or $R^{1'}$ as broadly described for generic structure I above, and each of said alkoxy groups (e.g. methoxy or ethoxy) is optionally further substituted with a $C_1$-$C_3$ alkosssxy group, preferably a methoxy group, thus forming a diether substituent.

In certain embodiments of the invention, $R^1$ and $R^{1'}$ are each independently H, a halo group, a nitro group or a trifluoromethyl group, preferably a chloro or fluoro group. R and R' are preferably each independently H or a $C_1$-$C_3$ optionally substituted alkyl group itself preferably substituted with at least one hydroxyl group, an amine, monoalkyl amine or dialkyl amine (where one or both alkyl groups is itself further optionally substituted with a dialkyl amine or an amine substituted with one or two (preferably one) 7-substituted-4-quinolinyl group(s) where the amine group is bonded to the 4-position of the quinolinyl group), an alkoxy group (e.g. methoxy or ethoxy) which may be further substituted with an alkoxy group, preferably a methoxy group (thus forming a diether substituent).

In a particularly preferred embodiment, the invention provides compounds of the formulae IIA, IIB, IIC and IID, and the pharmaceutically acceptable salts, enantiomers, diastereomers, solvates or polymorphs thereof:

IIA:

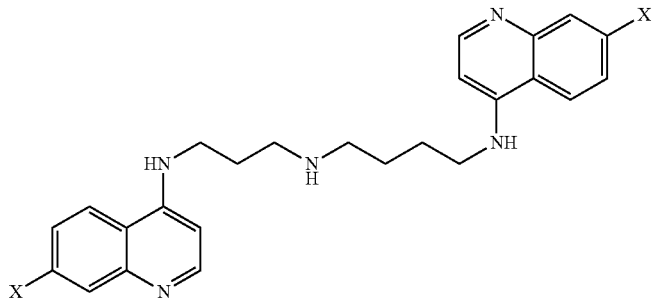

Lys-21: X = Cl
where X is a halogen (preferably F or Cl), or a pharmaceutically acceptable salt thereof;

IIB:

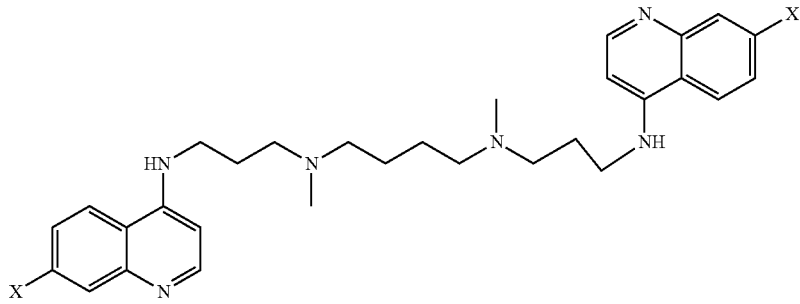

Lys-25: X = Cl;
where X is a halogen (preferably F or Cl), or a pharmaceutically acceptable salt thereof;

IIC:

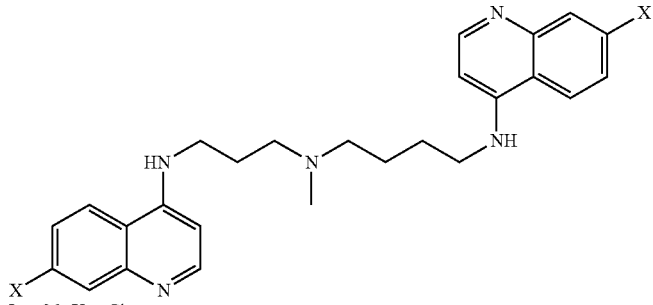

Lys-26: X = Cl
where X is a halogen (preferably F or Cl), or a pharmaceutically acceptable salt thereof; and

IID

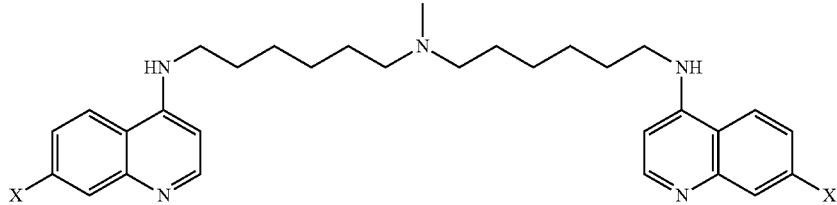

Lys-74: X = Cl
where X is a halogen (preferably F or Cl), or a pharmaceutically acceptable salt thereof.

Further preferred compounds according to the present invention include those which are presented or identified in any of FIGS. 10-13 or the various schemes as presented herein.

In other embodiments, the invention provides methods of treatment and pharmaceutical compositions which use therapeutically-effective amounts of compounds of Formulae IA, IB, IC, ID, IE, IIA, IIB and IIC, the other compounds described herein (e.g. the compounds of Tables 1-2 and FIGS. 10-13) and the pharmaceutically acceptable salts, enantiomers, diastereomers, solvents or polymorphs thereof, to treat cancer and other autophagy-related disorders.

As described further hereinafter, compounds of the invention exhibit an unexpectedly high level of cytotoxicity in a variety of cancer cells and evidence effective autophagy inhibition at surprising low doses, indicating their effectiveness in the treatment of broad spectrum of autophagy-related disorders.

These and other aspects of the invention are illustrated further in the Detailed Description of the Invention.

BRIEF DESCRIPTION OF THE FIGURES

FIG. 2 shows the effects of asymmetry and longer linker length on the cytotoxicity of dimeric chloroquines. A375P melanoma cells were plated in a 384 well format and treated with increasing concentrations of Lys01 derivatives. After 72 hours the cells were analyzed by alamar blue. Complete data is in Table 1, FIG. 10. (A) IC50 according to symmetry of linker (B) IC50 by linker length.

FIG. 3 shows subcellular localization of dimeric chloroquines with varied linkers. (A) Lys21 was tagged with a fluorescent dye Cy3 (B) A375P melanoma cells stained with lysotracker (light grey), and co-treated with Lys21-Cy3. Lighter color in third frame indicates colocalization.

FIG. 9 shows the effects of dimeric CQ's with longer linker on growth and invasion in a 3D tissue like culture model. A375P mCherry eGFP-LC3 cells grown into 3 dimensional spheroids and implanted in collagen. After 72 hours of treatment with 3 uM of indicated compound, cells were counterstained with DAPI. (A) fluorescence microscopy was used to visualize autophagy inhibition (bright areas), inhibition of invasion into the collagen and (B) quantification of the DAPI fluorescence indicative of cell death. * p<0.05

FIG. 10, Table 1 shows the results of cytotoxicity experiments using compounds according to the present invention. LN229 glioma cells, and A375P melanoma cells were plated in a 384 well format and compounds CQ, HCQ, and Lys01-Lys41 and 72-75 (IUPAC names and chemical structures provided in FIGS. 11 and 12) were delivered in concentrations between 0.01-10 micromolar using robotic assisted dispenser. After 72 hours incubation at 37 degrees, Alamar blue was applied and viability was determined using absorbance. Absorbance was normalized to DMSO control, and a log IC50 was estimated using Graphpad Prism software.

FIG. 11, Table 2 provides the IUPAC names for the compounds which are set forth in attached FIG. 12.

DETAILED DESCRIPTION OF THE INVENTION

Figure 1:
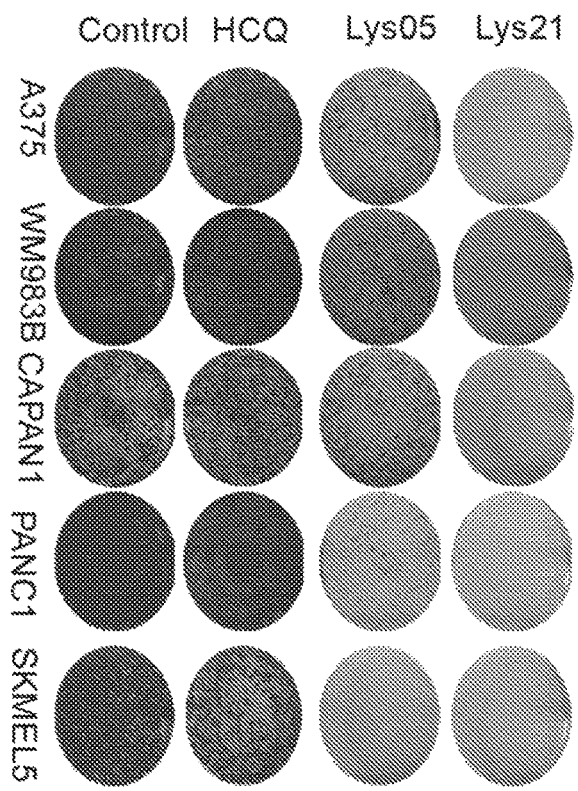
FIG. 1 shows the cytotoxicity of dimeric CQs with longer linkers. (A) IC50 of selected Lys01 derivatives (complete dataset in table 1) with longer linkers in a 72 hour alamar blue viability assay. A375 P cells seeded in a 384 well format were treated with a 10 point dilution of concentrations (0.01 nM-10 uM) (B) Colony formation assay in soft agar. Cells from the indicated melanoma (A375, WM983B, SKMEL5) and pancreatic cancer (PANC1, CAPAN1) cell lines were plated in soft agar. Medium with compound was changed every 48 hours. Crystal violet staining was used to visualize formed colonies after 2 weeks.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges that may independently be included in the smaller ranges are also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diastereomers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein. It is understood that the choice of substituents or bonds within a Markush or other group of substituents or bonds is provided to form a stable compound from those choices within that Markush or other group. In compounds according to the present invention, $R^1$ and $R^M$ or $R^{1'}$ and $R^M$ do not together form a cyclic ring.

The term "bioactive agent" refers to any biologically active compound or drug which may be formulated for use in the present invention. Exemplary bioactive agents include the compounds according to the present invention which are used to inhibit autophagy and to treat cancer as well as other compounds or agents which are otherwise described herein.

The terms "treat", "treating", and "treatment", are used synonymously to refer to any action providing a benefit to a patient at risk for or afflicted with a disease, including improvement in the condition through lessening or suppression of at least one symptom, delay in progression of the disease, prevention or delay in the onset of the disease, etc.

Treatment, as used herein, encompasses both prophylactic and therapeutic treatment, principally of cancer. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease that subsequently occurs, especially including metastasis of cancer. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present invention is effective to decrease the severity of the disease or lengthen the lifespan of the mammal so afflicted, in the case of cancer.

The term "pharmaceutically acceptable" as used herein means that the compound or composition is suitable for administration to a subject to achieve the treatments described herein, without unduly deleterious side effects in light of the severity of the disease and necessity of the treatment.

The term "inhibit" as used herein refers to the partial or complete elimination of a potential effect, while inhibitors are compounds that have the ability to inhibit.

The term "prevention" when used in context shall mean "reducing the likelihood" or preventing a disease, condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients or subjects, administration with compounds according to the present invention will reduce the likelihood or inhibit a particular condition or disease state (in particular, the worsening of a disease state such as the growth or metastasis of cancer) or other accepted indicators of disease progression from occurring.

The term "autophagy" or "autophagocytosis" is used to describe a catabolic process in cells which involves the degradation of a cell's own components through lysosomes. Autophagy is a highly regulated process of biological systems that plays a normal part in cell growth development and homeostasis. helping to maintain a balance between the synthesis, degradation, and subsequent recycling of cellular products. It is a major mechanism by which a cell allocates nutrients from unnecessary processes to more-essential processes.

A number of autophagic processes occur in nature, all of which have the degradation of intracellular components via the lysosome as a common feature. A well-known mechanism of autophagy involves the formation of a membrane around a targeted region of a cell, separating the contents from the rest of the cytoplasm. The resultant vesicle then fuses with a lysosome which subsequently degrades the contents.

Autophagy consists of the sequestration of organelles and proteins in autophagic vesicles (AV) and degradation of this cargo through lysosomal fusion (1). Autophagy allows tumor cells to survive metabolic and therapeutic stresses (2-5). Multiple publications indicate therapy-induced autophagy is a key resistance mechanism to many anticancer agents.

An "autophagy-related disorder" includes diseases, disease states and/or conditions which benefit from the inhibition of autophagy, including, but not limited to, cancer (including the metastasis of cancer), rheumatoid arthritis, malaria, antiphospholipid antibody syndrome, lupus, chronic urticaria and Sjogren's disease.

The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of dysplasia, or loss of differentiation and orientation of cells, and have the properties of invasion and metastasis. The term cancer also within context, includes drug resistant cancers, including multiple drug resistant cancers, metastatic cancers and/or recurrent cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, thyroid, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. It is noted that certain epithelial tumors including ovarian, breast, colon, head and neck, medulloblastoma and B-cell lymphoma, among others are shown to exhibit increased autophagy and are principal target cancers for compounds and therapies according to the present invention.

The term "additional anti-cancer agent" is used to describe an additional compound which may be coadministered with one or more compounds of the present invention in the treatment of cancer. Such agents include, for example, everolimus, trabectedin, abraxane, ILK 286, AV-299, DN-101 pazopanib, GSK690693, RTA 744, ON 0910.Na, AZD 6244 (ARRY-142886), AMN-107, TK1-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PFK-1 modulator, a Bcl-2 inhibitor, an HDAC inhbitor, a c-MET inhibitor, a PARP inhibitor, a Cdk inhibitor, an EGFR TK inhibitor, an IG-FR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001 IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, PD0325901 AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But) 6, Azgly 10] (pyro-Glu-His-Trp-Ser-Tyr-D-Ser(But)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafamib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine. 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU541.6, SU6668, EMD121974, interleukin-12, fM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib among others.

The term "alkyl" is used herein to refer to a fully saturated monovalent radical containing carbon and hydrogen (up to 10 carbon atoms or as otherwise indicated), and which may be a straight chain, branched or cyclic. Examples of alkyl groups are methyl, ethyl, n-butyl, n-heptyl, isopropyl, 2-methyl propyl, tert-butyl, neopentyl, hexyl, heptyl, octyl, nonyl, decyl, etc.

The term "substituted" as that term relates to alkyl groups which are described above include one or more functional groups such as lower alkyl groups containing 1-6 carbon atoms which are optionally substituted with 1 or 2 hydroxyl groups or between 1 and 5 (preferably 3-5) fluoro groups, acyl ($C_1$-$C_6$), halogen (F, Cl, Br, I, e.g., alkyl halos, e.g., $CF_3$), amido, hydroxyl, carboxy/carboxylic acid, thioamido, cyano, nitro, alkenyl ($C_2$-$C_6$) alkynyl ($C_2$-$C_6$), azido, alkoxy ($C_1$-$C_6$), (including alkoxy groups which are further substituted with a $C_1$-$C_6$ alkoxy group thus producing a diether group), amino, $C_1$-$C_6$ alkylamino and dialkyl-amino, where the alkyl groups may be optionally substituted with 1 or 2 hydroxyl groups or an amine, aminoalkyl or dialkyl group which itself is substituted one or two alkyl groups or a 7-substituted-4-quinolinyl group, $C_2$-$C_6$ acylamino, $C_2$-$C_6$ oxyacylester or carboxyester, aryloxy, aryloxy($C_1$-$C_6$)alkyl, carboxamido, thio, $C_2$-$C_6$ ether or thioether, a 7-substituted-4-aminoquinolinyl group (or a substitution on an amine group which forms a 7-substituted-4-aminoqunolinyl group) and the like. Preferred substituents on alkyl groups (within context, especially on the amino group of the 7-substituted-4-aminoquinoline) or a linker which contains at least one amine group, include, for example, at least one hydroxyl group, an amine, monoalkyl amine or dialkyl amine (where one or both alkyl groups is itself further optionally substituted with a dialkyl amine or an amine substituted with one or two (preferably one) 7-substituted-4-quinolinyl group(s) where the amine group is bonded to the 4-position of the quinolinyl group) or an alkoxy group (e.g. methoxy or ethoxy) which may be further substituted with an alkoxy group, preferably a methoxy group, thus forming a diether substituent.

The term "aryl" refers to a substituted or unsubstituted monovalent aromatic radical having a single ring (e.g., phenyl) or multiple condensed rings (e.g., naphthyl). Other examples include heterocyclic aromatic (heteroaromatic or heteroaryl) ring groups having one or more nitrogen, oxygen, or sulfur atoms in the ring, in particular, quinoline groups, in particular, 7-substituted-amino quinoline groups, as well as other groups.

The term "substituted" as used in the term "substituted aryl, substituted aromatic, substituted heteroaryl, or substituted heteroaromatic" herein signifies that a substitution on the 7-position of 4-aminoquinoline may be present, said substituents being selected from atoms and groups, which when present enhance the activity of the compound as an inhibitor of autophagy. Examples of substituents that may be present in a substituted aromatic or heteroaromatic group include, but are not limited to, groups such as H, halo (F, Cl, Br or I), CN, $NO_2$, optionally substituted $C_1$-$C_6$ alkyl (when substituted, preferably substituted with 1 or 2 hydroxyl groups or 3-5 fluoro groups), optionally substituted O—$C_1$-$C_6$ alkyl (preferably, $OCH_3$), optionally substituted $C_2$-$C_7$ acyl (preferably acetyl) or optionally substituted $C_2$-$C_7$ ester (oxycarbonyl ester or carboxyester, preferably carboxyester). It is noted that each of the substituents disclosed herein may themselves be substituted.

The term "co-administration" or "adjunct therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the tem' embraces both administration of two or more agents at the same time or at different times, including sequential administration. Preferably, effective concentrations of all co-administered compounds or compositions are found in the subject at a given time. The term co-administration or adjunct therapy also contemplates other bioactive agents being coadministered with pharmaceutical compositions according to the present invention, especially where a cancer has metastasized or is at risk for metastasis.

The term "amine protecting group" refers to a moiety or group which can be readily removed from a functional group to which the protecting group is attached to allow further reaction. Exemplary amine-protecting groups include carbobenzyloxy (Cbz group, removed by hydrogenolysis), p-Methoxylbenzyl carbon (Moz or MeOZ group, removed by hydrogenolysis), tert-butyloxycarbonyl (BOC group, removed by concentrated strong acid or by heating at elevated temperatures), 9-Fluorenylmethyloxycarbonyl (FMOC group, removed by weak base, such as piperidine or pyridine), acyl group (acetyl, benzoyl, pivaloyl, by treatment with base), benzyl (Bn groups, removed by hydrogenolysis), carbamate, removed by acid and mild heating, p-methoxybenzyl (PMB, removed by hydrogenolysis), 3,4-dimethoxybenzyl (DMPM, removed by hydrogenolysis), p-methoxyphenyl (PMP group, removed by ammonium cerium IV nitrate or CAN); tosyl (Ts group removed by concentrated acid and reducing agents, other sulfonamides, Mesyl, Nosyl & Nps groups, removed by samarium iodide, tributyl tin hydride.

The term "radiotherapy" or "radiation therapy" is used to describe therapy for cancer which may be used in conjunction with the present compounds. Radiation therapy uses high doses of radiation, such as X-rays, or other energy sources such as radioisotopes (gamma, beta or alpha emitters), to destroy cancer cells. The radiation damages the genetic material of the cells so that they can't grow. Although radiation damages normal cells as well as cancer cells, the normal cells can repair themselves and function, while the cancer cells cannot.

Radiation therapy may be used in combination with the presently claimed compounds, alone or in combination with additional anticancer compounds as otherwise disclosed herein, depending on the cancer to be treated. Radiotherapy therapy is most effective in treating cancers that have not spread outside the area of the original cancer, but it also may be used if the cancer has spread to nearby tissue. Radiotherapy is sometimes used after surgery to destroy any remaining cancer cells and to relieve pain from metastatic cancer.

Pharmaceutical Compositions

Compounds according to the present invention may be readily formulated into pharmaceutical compositions, useful in the inhibition of autophagy in a biological system and/or the inhibition, treatment or prevention of diseases states and/or conditions which benefit from the inhibition of autophagy including cancer (and its metastasis), rheumatoid arthritis, malaria, antiphospholipid antibody syndrome, lupus (systemic lupus erythematosus), chronic urticaria and Sjogren's disease. Pharmaceutical compositions comprise an effective amount of one or more compounds according to the present invention in combination with a pharmaceutically acceptable carrier, additive or excipient, optionally in combination with at least one additional agent, in the case of cancer, preferably an anticancer agent as otherwise described herein.

As noted above, the compounds and method of the invention may be used to inhibit autophagy as otherwise described herein, and are useful for the inhibition (including prophylaxis) and/or treatment of cancer and its metastasis, rheumatoid arthritis, malaria, antiphospholipid antibody syndrome, lupus (systemic lupus erythematosus), chronic urticaria and Sjogren's disease. The treatment of cancer or malaria are important aspects of the present invention.

In methods according to the present invention, subjects or patients in need are treated with the present compounds, pharmaceutical compositions in order to inhibit, reduce the likelihood or treat a disease state, condition and/or infection as otherwise described herein. The disease states, conditions and infections treated by the present compounds and compositions are readily recognized and diagnosed by those of ordinary skill in the art and treated by administering to the patient an effective amount of one or more compounds according to the present invention.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, irathecally or intramuscular injection, among others, including buccal, rectal and transdermal administration. Compositions may also be administered by inhalation to the lungs. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for inhibiting autophagy in a biological system, including a patient or subject according to the present invention.

Method of Treatment

According to one aspect of the invention, a method is provided for treating a mammalian patient or subject to inhibit autophagy in that patient or subject. Compounds according to the present invention described herein may be used to inhibit autophagy in a manner consistent with inhibiting, treating and/or preventing disease states and/or conditions including cancer (including metastasis of cancer), rheumatoid arthritis, malaria, antiphospholipid antibody syndrome, lupus, chronic urticaria and Sjogren's disease.

According to the present invention, in patients or subjects in need thereof, are treated by administering to the patient or subject an effective amount of one or more compounds according to the present invention, optionally in combination with at least one additional bioactive agent useful for treating the same disease state or condition. Compounds according to the present invention may be used to inhibit, reduce the likelihood or treat cancer, including the metastasis of cancer in a patient or subject in need of such treatment. The treatment is useful for any cancer for which inhibition of autophagy represents a favorable result or for which metastasis is a risk element. Therapy with at least one additional anticancer agent as otherwise described herein is also contemplated in the present methods. The numerous cancers which may be treated pursuant to the present method are described hereinabove.

In another aspect the present invention is directed to a method for treating a disease state and/or condition which benefits from the inhibition of autophagy, including rheumatoid arthritis, malaria, antiphospholipid antibody syndrome, lupus, chronic urticaria and Sjorgen's disease. In this method, a patient or subject in need of treatment is administered an effective amount of a compound as otherwise described herein optionally in combination with a pharmaceutically acceptable carrier, additive or excipient in order to inhibit, treat and/or prevent the above disease states of conditions. In alternative embodiments, at least one additional bioactive agent is coadministered with a compound according to the present invention.

In certain preferred embodiments of the invention, at least one (preferably two) $R^M$ is other than H, especially when $R^1$ and $R^{1'}$ are H. In other preferred aspects of the invention, $R^1$ and $R^{1'}$ are each independently H, a halo group (most often Cl or F), a nitro group or a trifluoromethyl group, most often a chloro or fluoro group. R and R' are preferably each independently H or methyl, preferably H and L is preferably an alkylene group containing from 6 to 20 methylene groups (6, 7, 8, 9, 10, 11, 12, 13, 14, 15, 16, 17 18, 19 or 20), a (poly)ethylene glycol group having from 1 to 20 (1, 2, 3, 4, 5, 6, 7, 8, 9, 10, 11, 12, 13, 14, 15, 16, 17, 18, 19 or 20, preferably 2 to 15, 3 to 10 or 4, 5, 6, 7, 8, 9, or 10) ethylene glycol units, each (poly)ethylene glycol group being optionally substituted at one or both of its distal ends with an A group, or L is a linear group containing from 1 to 5 non-contiguous amine groups N—R", each amine group being separated from an adjacent amine group by an alkylene group containing from 1, 2, 3, 4, 5, 6, 7, or 8 (preferably 2, 3 or 4) methylene groups or an ethylene glycol containing group having from 1 to 6 (preferably 2 to 6, 3 to 6 or 4, 5 or 6) ethylene glycol units. R" is preferably H, methyl or an amine protecting group (preferably a benzyl or benzoyl group which can be removed to introduce other groups on the amine group after deprotection).

In certain embodiments, one or more amine group of L is optionally substituted with one or two 7-substituted-4-quinolinyl group(s) wherein the amine binds to the 4-position of the quinolinyl group through an alkylene group and the 7-position of each quinolinyl group is optionally substituted, preferably with a $R^1$ and/or $R^{1'}$ group as broadly described for generic structures IA, IB, IC, ID and IE above, or one or more amines of the linker group is substituted with an alkyl group which itself is further optionally substituted with at least one hydroxyl group, an alkoxy group, an amine, a monoalkyl ($C_1$-$C_6$, preferably $C_1$-$C_3$) amine or a dialkyl ($C_1$-$C_6$, preferably $C_1$-$C_3$) amine wherein the amine or monoalkyl amine is optionally substituted on the amine position with one or two 7-substituted-quinolinyl group(s) wherein the amine binds to the 4-position of the quinolinyl group and the 7-position of each quinolinyl group is optionally substituted, preferably with $R^1$ and/or $R^{1'}$ as broadly described for generic structures IA, IB, IC, ID and IE above, and each of said alkoxy groups (e.g. methoxy or ethoxy) is optionally further substituted with a $C_1$-$C_3$ alkoxy group, preferably a methoxy group, thus forming a diether substituent.

Further preferred methods relate to the use/administration of the compounds according to the present invention which are presented in the various schemes which are presented in the tables and figures presented herein.

In the methods treating or inhibiting cancer or the metastasis of cancer, the compounds described above may be coadministered with at least one additional anticancer agent including, for example, everolimus, trabectedin, abraxane, ILK 286, AV-299. DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd21.71, batabulin, ofatumumab, zanolimumab, edotecarin, tetrancirine, rubitecan, tesmilifene, oblimersen, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, sodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But) 6, Azgly 10] (pyro-Glu-His-Trp-Ser-Tyr-D-Ser(But)-Leu-Arg-Pro-Azgly-$NH_2$ acetate [$C_{59}H_{84}N_{18}Oi_4$-$(C_2H_4O_2)_X$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, megestrol acetate, CP-724714; TAK-165, HKI-272, erlotinib, lapatanib, canertinib, ABX-EGF antibody, erbitux, EKB-569, PKI-166, GW-572016, Ionalarnib, BMS-214662, tipifarnib; amifostine, NVP-LAQ824, suberovl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, ciadribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levatnisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, inarimastat, COL-3, neovastat, BMS-275291 squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others, and mixtures thereof.

In methods involving infections, disease states and/or conditions caused by rheumatoid arthritis, malaria, antiphospholipid antibody syndrome, lupus, chronic urticaria and Sjogren's disease, the compounds according to the present invention may be coadministered with additional agents which are traditionally used in therapy for these disease states and/or conditions.

EXAMPLES

Figure 12:
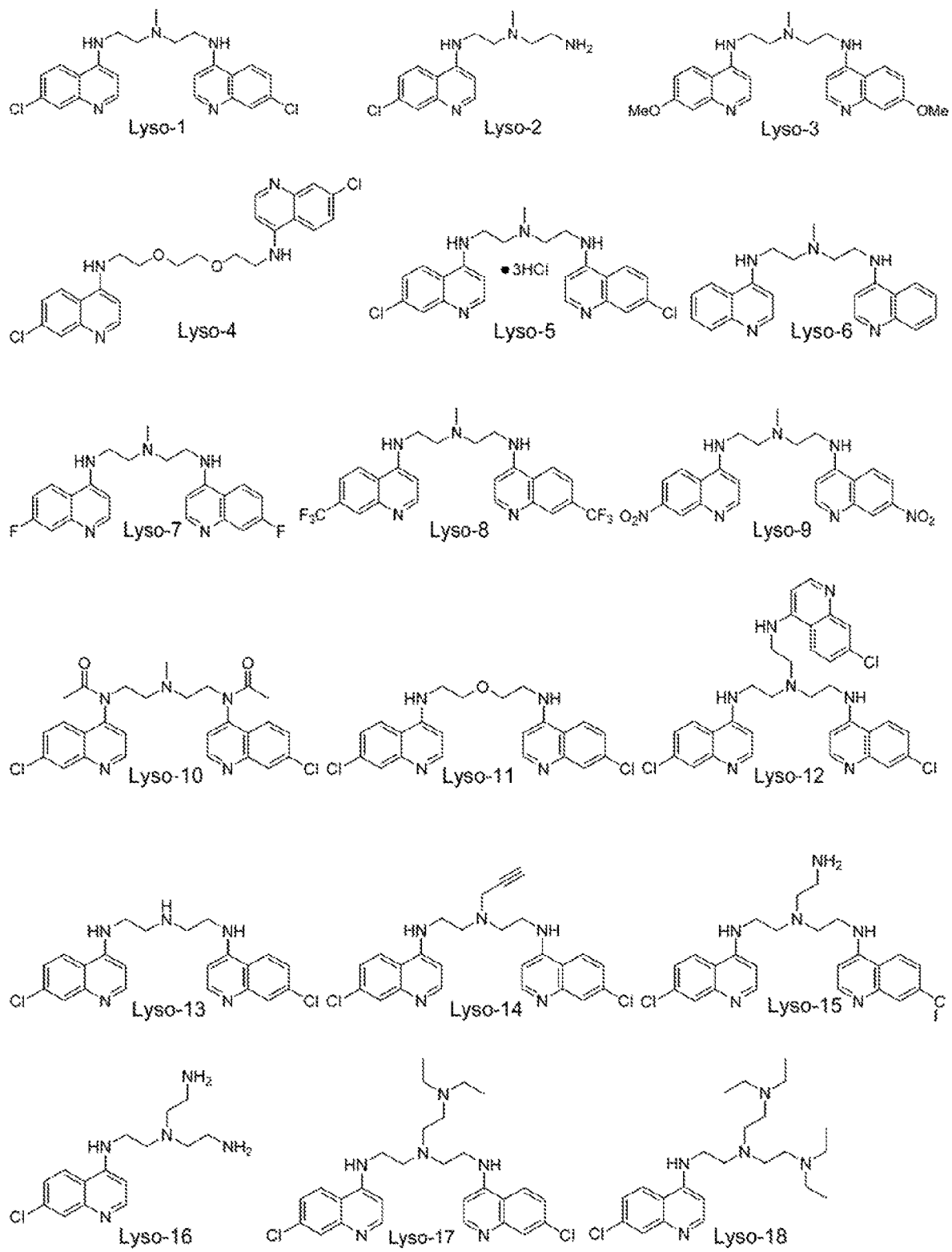
FIG. 12 shows representative chemical structures of compounds according to the present invention.
Figure 12:
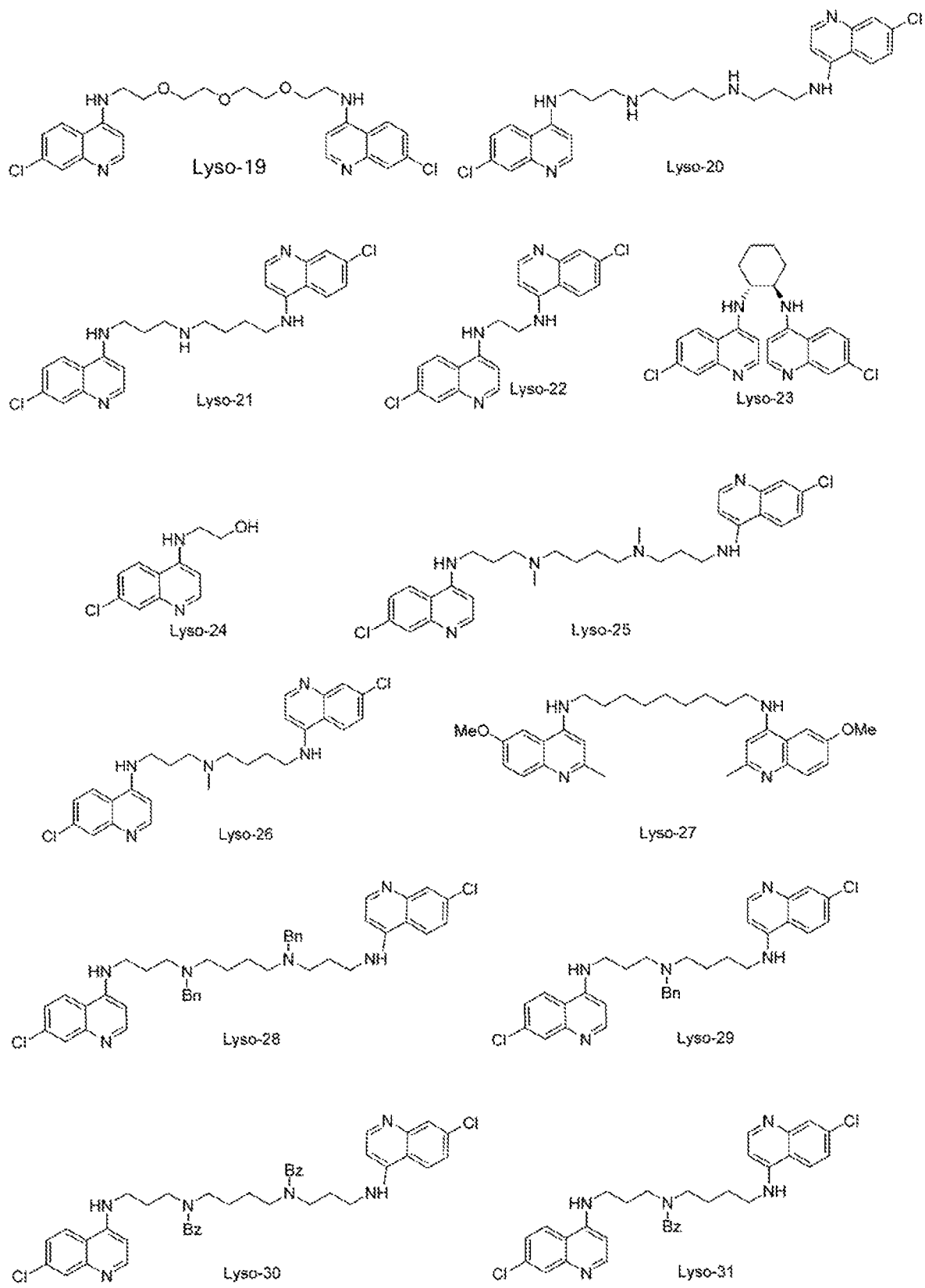
Figure 12:
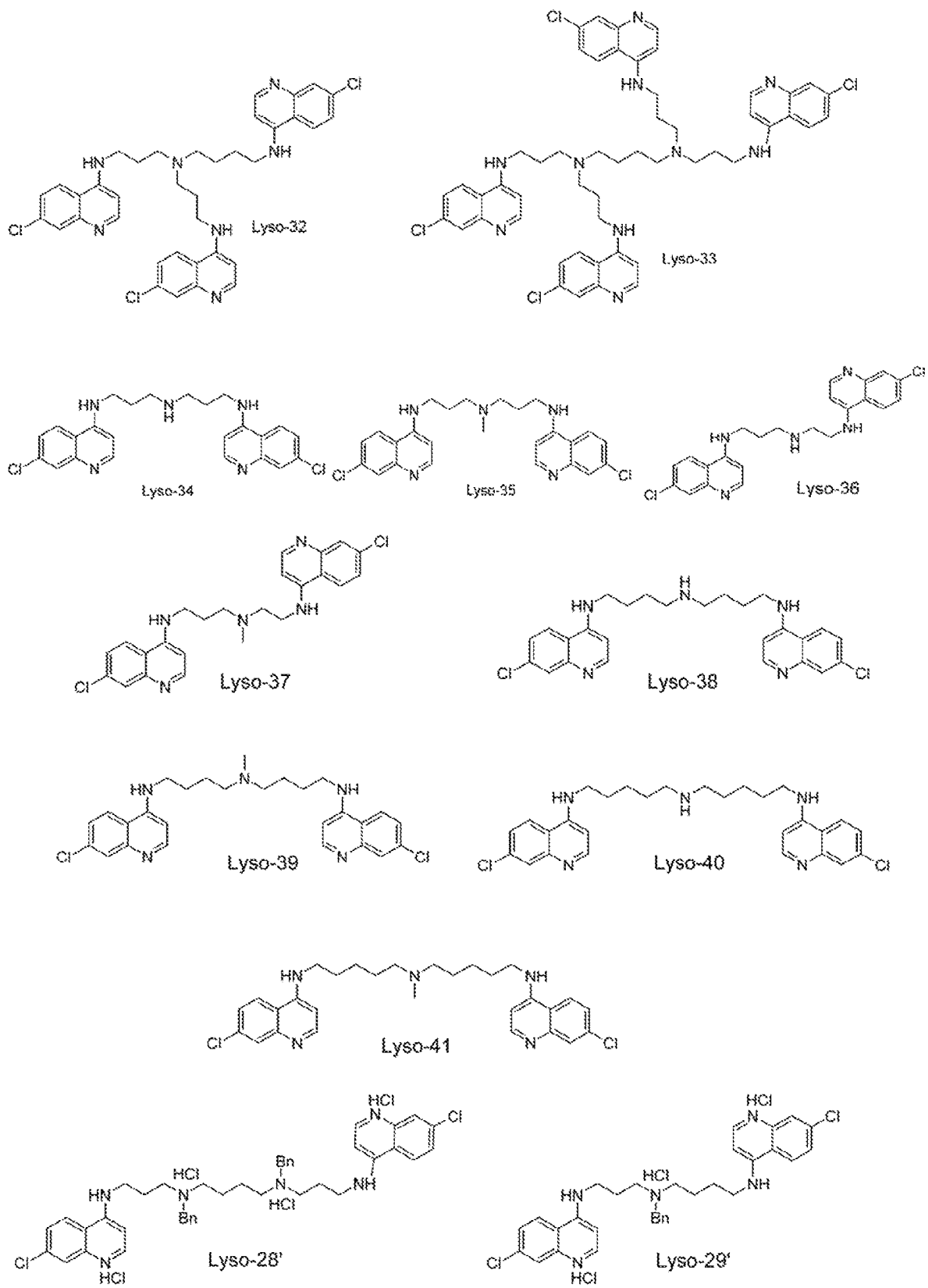
Figure 12:
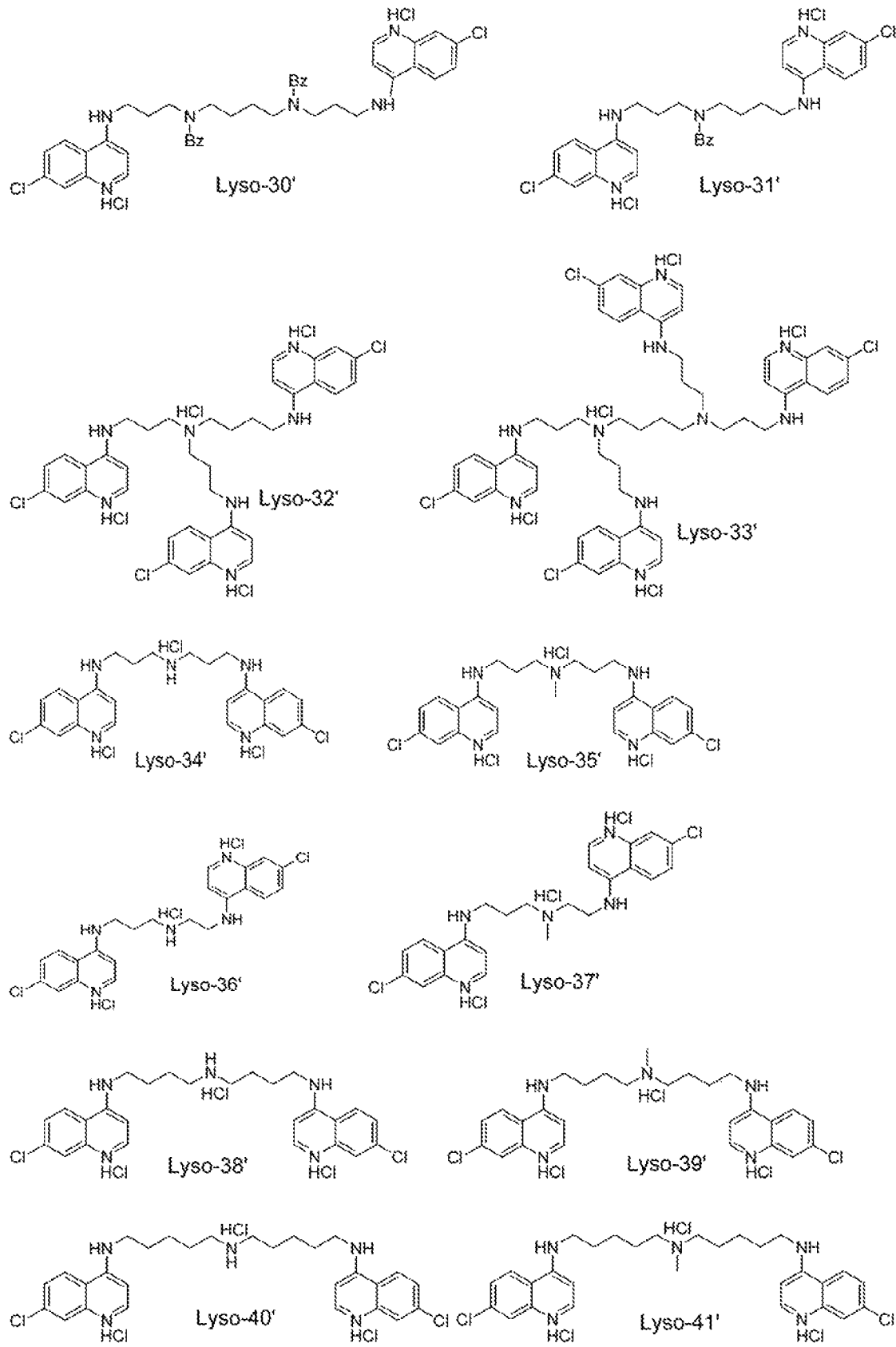
Figure 12:
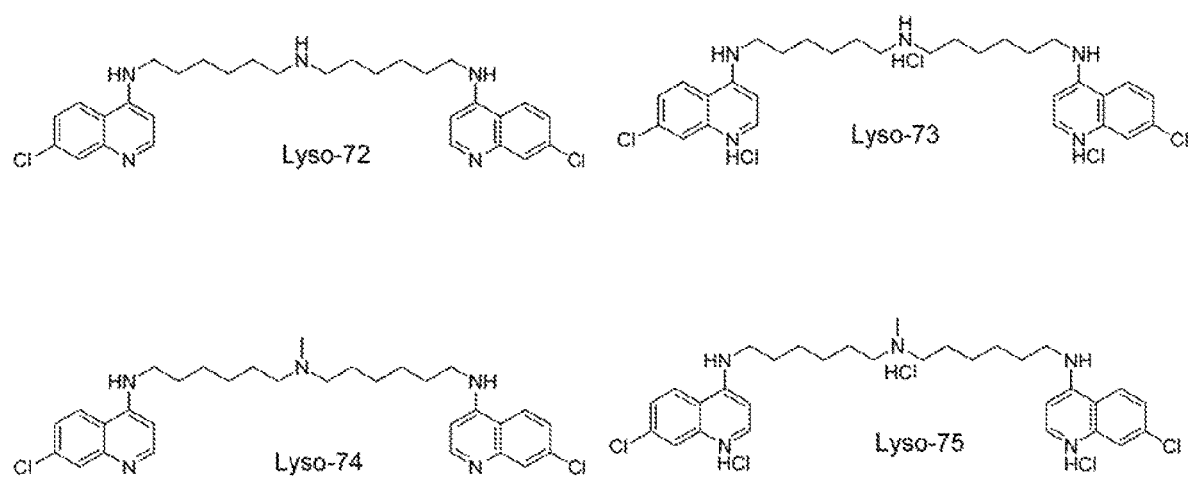

The following examples illustrate and describe the present invention but are not intended to limit the invention in any way.
Chemical Methods
Strategy for Synthesis of Bivalent Aminoquinoline Autophagy Inhibitors with Varying Linker Lengths The compounds are prepared as previously described (PNAS) by Buchwald-Hartwig coupling of the appropriate spacer molecule diamine with the requisite 4-substituted quinoline, which are either commercially available or could be readily prepared by standard methods. To establish the role of linker length, and of the asymmetric nature of the linker length of spermidine (3,4) relative to Lys01 (2,2), we have prepared a series of new compounds that systematically vary the number of methylenes, i.e., CH2 groups, between the nitrogen atoms of the linker, where x and y=1-4 in the formula —HN(CH2)xNR(CH2)yNH—. These compounds are listed in FIG. 10, Table 1, FIG. 11, Table 2 and FIG. 12 as Lys 34-41 and Lys 72-75.

In addition, numerous compounds according to the present invention may be readily prepared pursuant to the synthetic methods provided inter alis on pages 21-28 of international application PCT/US2012/035251 (WO 2012/149186), relevant portions of which are incorporated by reference herein. Additional compounds may be prepared by analogy from the disclosed methods as well as analogously from synthetic procedures which are well known in the art.

Chemistry Experimental Protocol (Exemplary Syntheses)

4-Bromo-7-chloroquinoline:[J. Org. Chem. 2007 (72) 2232]

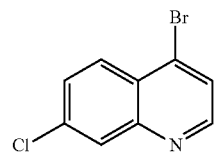 [SMILES: Clc1ccc2c(Br)ccnc2c1]

At 0° C. under an atmosphere of argon, phosphorus tribromide (5.8 mL, 0.079 moles, 1.10 equiv.) was added slowly to a solution of 7-chloro-4-hydroxyquinoline (13.02 g, 0.073 moles, 1.00 equiv.) in anhydrous DMF (150 mL, 0.5 M soln.). The reaction was allowed to warm to rt and followed by TLC. Complete consumption of starting material was observed after 90 minutes stirring. The reaction mixture was poured onto ice and the pH was rendered alkaline using solid sodium bicarbonate. This resulted in a white precipitate. The mixture was then filtered and the resulting solid was dried under vacuum affording an off-white solid (17.30 g, 99%). The material was recrystallised from ethyl acetate to give white needles (12.20 g, 70%). $R_f$=0.70 (hex:EtOAc; 1:1); Mp=99-101° C., EtOAc (lit.,[Eur. J. Org. Chem. 2002 4181] 103-104° C., hex).
Lyso-01:[McAfee et. al. PNAS]

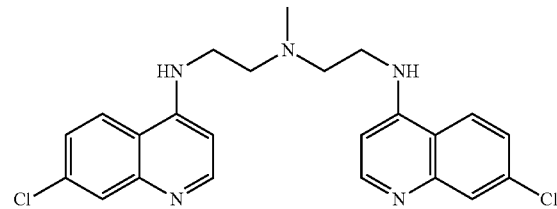 [SMILES: CN(CCNc1ccnc2cc(Cl)ccc12)CCNc1ccnc2cc(Cl)ccc12]

Under argon, a mixture of degassed dioxane and water (10:1; 22 mL, 0.4 M soln.) was added to 4-bromo-7-chloroquinoline (4.78 g, 19.840 mmol, 2.25 equiv.), BINAP (0.81 g, 1.302 mmol, 0.15 equiv.), Pd(OAc)$_2$ (0.16 g, 0.716 mmol, 0.08 equiv.), potassium phosphate tribasic (6.911 g, 32.560 mmol, 3.69 equiv.) and N-methylethane-1,2-diamine (0.94 mL, 8.814 mmol, 1.00 equiv.). The reaction was heated to 120° C. in a sealed tube and heating was maintained for 16 hours. The reaction was then cooled to rt and filtered on a pad of celite washing through with chloroform (3×50 mL). The reaction was rendered acidic via the addition of aqueous HCl (1 M, 18 mL, 17.628 mmol, 2 equiv.) resulting in the precipitation of the HCl salt. This precipitate was isolated via filtration and the remaining organic layer was extracted with deionised water (2×50 mL). The isolated HCl salt was added to the aqueous washings which was then rendered basic via the addition of ammonium hydroxide (until pH≥9). This now alkaline mixture was extracted with CHCl$_3$ (3×40 mL). Combined chloroform fractions were washed with brine, dried over Na$_2$SO$_4$ and filtered. Concentration under reduced pressure resulted in the isolation of pure compound as an orange solid (2.74 g, 71%). The material was recrystallised from EtOAc, resulting in the isolation of needles (43% recrystallised yield). $R_f$=0.70.
Lyso-05: [McAfee et al. PNAS]

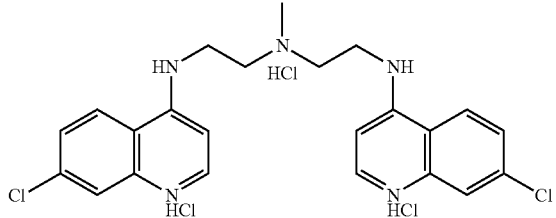

A solution of the Lyso-01 (2.68 g, 6.098 mmol, 1.00 equiv.) in MeOH (20 mL) was treated with 1M aqueous HCl (20 mL). The resulting reaction was stirred vigorously at room temperature for 4 hours. The product was insoluble in the reaction media and was collected via filtration. The residue was collected and taken up in excess water. Sonication and heating was necessary to solubilise the product. The aqueous solution was lyophilised to give a white crystalline solid (1.77 g, 53%). Starting material (0.726 g, 27%) was recovered from the reaction. Mp=270° C. (decomposition) (Lit., [PNAS] 270° C.); HPLC analysis of Lyso-05 showed >99% purity.

Lyso-10:

Lyso-1 (0.26 g, 0.60 mmol, 1.00 equiv.) was placed under a blanket of argon. Pyridine (0.5 mL, 5.95 mmol, 10.00 equiv.) followed by acetic anhydride (1.1 mL, 11.90 mmol, 20.00 equiv.) were added and the resulting reaction was heated to 150° C. for 2 hours. Following this the reaction mixture was poured onto a solvent mixture of $CHCl_3$ (40 mL) and water (40 mL) and agitated vigorously. The resulting layers were allowed to settle and separated. The aqueous layer was further extracted with $CHCl_3$ (3×40 mL). Combined $CHCl_3$ extracts were washed with brine (120 mL) and dried over $Na_2SO_4$. Filtration followed by solvent evaporation afforded a brown oil (0.12 g, 38% yield) which was found to be very pure.

Lyso-20:

To a microwave vial was added spermine (0.57 g, 2.83 mmol, 1.00 equiv.), 4-Bromo-7-chloroquinoline (1.32 g, 6.38 mmol, 2.25 equiv.), BINAP (0.11 g, 0.17 mmol, 0.06 equiv.), $Pd(OAc)_2$ (0.02 g, 0.09 mmol, 0.03 equiv.) and $K_3PO_4$ (1.80 g, 8.50 mmol, 3.00 equiv.). The vial was sealed and placed under argon. A solvent mixture of dioxane and water (10:1, 9 mL, 0.3 M) was added and the reaction was heated to 120° C. for 16 hours. The reaction was followed by TLC and NMR and once complete it was cooled to room temperature. Following this the reaction was filtered on celite, washing through with MeOH (100 mL). The resulting solution was concentrated to give a solid. This solid was washed with $CHCl_3$ (3×30 mL) to remove impurities, affording the product as a yellowish solid (1.09 g, 73% yield) which was found to be very pure.

Lyso-21:

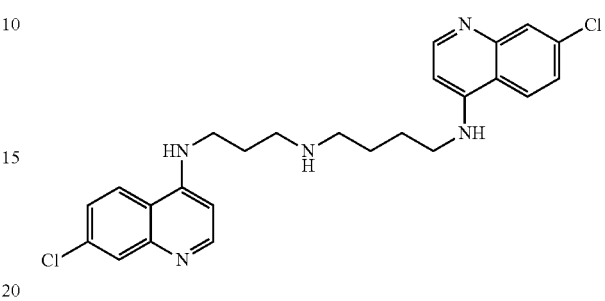

To a sealable tube was added spermidine (0.98 g, 6.76 mmol, 1.00 equiv.), 4-Bromo-7-chloroquinoline (3.69 g, 15.21 mmol, 2.25 equiv.), BINAP (0.17 g, 0.27 mmol, 0.04 equiv.), $Pd(OAc)_2$ (0.03 g, 0.14 mmol, 0.02 equiv.) and $K_3PO_4$ (4.30 g, 20.28 mmol, 3.00 equiv.). The vial was sealed and placed under argon. A solvent mixture of dioxane and water (10:1, 22.5 mL, 0.3 M) was added and the reaction was heated to 120° C. for 16 hours. The reaction was followed by TLC and NMR and once complete it was cooled to room temperature. Following this the reaction was filtered on celite, washing through with MeOH (100 mL). The resulting solution was concentrated to give a solid. This solid was solubilised in $CHCl_3$ (60 mL) and 1 $M_{aq}$ HCl (60 mL) was added. The mixture was stirred vigorously at room temperature for 30 minutes, affording the corresponding water soluble HCl-salt of the product. The mixture was allowed to settle and the resulting layers were separated. The aqueous layer, containing the product, was further washed with $CHCl_3$ (2×60 mL). These combined organic washings were discarded at this point.

Using $NH_4.OH$, the pH of the aqueous layer was adjusted to 11, resulting in the liberation of the free base of the product. The product was extracted into a solvent mixture of $CHCl_3$ and i-propanol (4:1; 3×40 mL). These combined extracts were washed with brine (120 mL) and dried over $Na_2SO_4$. Filtration followed by solvent evaporation afforded the product as a white solid (2.05 g, 65% yield). $R_f$=0.10 (EtOAc:MeOH:TEA; 80:15:5).

Lyso-25:

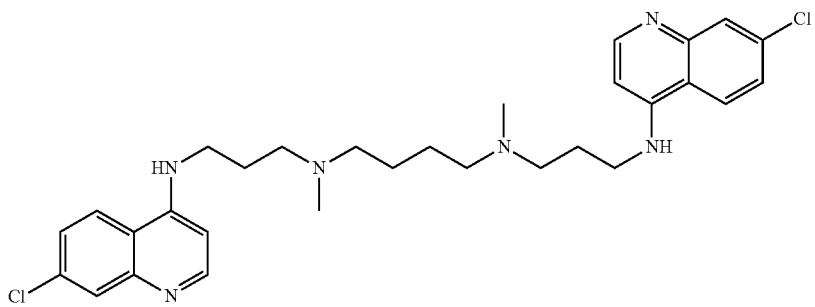 [SMILES: CN(CCCCN(C)CCCNc1ccnc2cc(Cl)ccc12)CCCNc1ccnc2cc(Cl)ccc12]

Lyso-20 (0.13 g, 0.25 mmol, 1.00 equiv.) was dissolved in DCM (2.5 mL, 0.1 M). Formaldehyde 37 wt % (0.08 g, 0.98 mmol, 4.00 equiv.), then sodium triacetoxyborohydride (0.21 g, 0.98 mmol, 4.00 equiv.) was added and the reaction was stirred at room temperature for 4 hours. At this point, TLC analysis showed complete consumption of Lyso-20. A 2 M$_{aq}$ NaOH solution (15 mL) was added to break up borane salts in the reaction mixture. The resulting mixture was stirred at rt for 1 hour before CHCl$_3$ (20 mL) was added. The resulting biphasic mixture was allowed to settle and separated. The aqueous layer was discarded at this point.

To the chloroform solution was added 1 M$_{aq}$ HCl solution (20 mL). The mixture was stirred vigorously at room temperature for 20 minutes, resulting in the formation of a water soluble salt of the desired product. The mixture was allowed to settle and both layers were separated. The aqueous layer was further washed with CHCl$_3$ (2×40 mL) and combined chloroform washings were discarded at this point.

Using NH$_4$.OH, the pH of the aqueous layer was adjusted to 11, resulting in the liberation of the free base of the product. The product was extracted into a solvent mixture of CHCl$_3$ and 1-propanol (4:1; 3×40 mL). These combined extracts were washed with brine (120 mL) and dried over Na$_2$SO$_4$. Filtration followed by solvent evaporation afforded the product as a white solid (16.0 mg, 12% yield). R$_f$=0.10 (EtOAc:MeOH:TEA; 80:15:5).

Lyso-26:

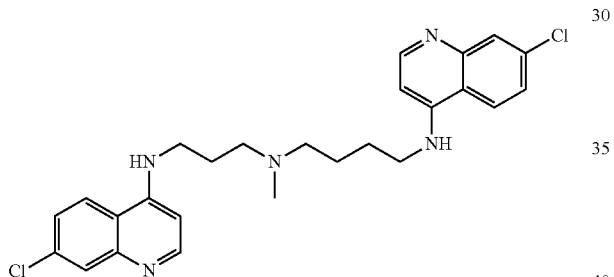

Lyso-21 (0.11 g, 0.23 mmol, 1.00 equiv.) was dissolved in DCM (2.5 mL, 0.1 M). Formaldehyde 37 wt % (0.04 g, 0.46 mmol, 2.00 equiv.), then sodium triacetoxyborohydride (0.19 g, 0.90 mmol, 4.00 equiv.) was added and the reaction was stirred at room temperature for 4 hours. At this point, TLC analysis showed complete consumption of Lyso-21. A 2 M$_{aq}$ NaOH solution (15 mL) was added to break up borane salts in the reaction mixture. The resulting mixture was stirred at rt for 1 hour before CHCl$_3$ (20 mL) was added. The resulting biphasic mixture was allowed to settle and separated. The aqueous layer was discarded at this point.

To the chloroform solution was added 1 M$_{aq}$ HCl solution (15 mL). The mixture was stirred vigorously at room temperature for 20 minutes, resulting in the formation of a water soluble salt of the desired product. The mixture was allowed to settle and both layers were separated. The aqueous layer was further washed with CHCl$_3$ (2×15 mL) and combined chloroform washings were discarded at this point.

Using NH$_4$.OH, the pH of the aqueous layer was adjusted to 11, resulting in the liberation of the free base of the product. The product was extracted into a solvent mixture of CHCl$_3$ and 1-propanol (4:1; 3×15 mL). These combined extracts were washed with brine (60 mL) and dried over Na$_2$SO$_4$. Filtration followed by solvent evaporation afforded the product as a white solid (86.0 mg, 79% yield). R$_f$=0.30 (EtOAc:MeOH:TEA; 80:15:5).

Ethyl (E)-3-((4-methoxyphenyl)amino)but-2-enoate

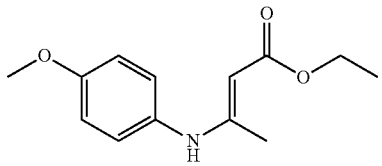 [SMILES: CCOC(=O)/C=C(\C)Nc1ccc(OC)cc1]

Prepared pursuant to *Tetrahedron*, 2012, 5522.

6-Methoxy-2-methylquinolin-4-ol

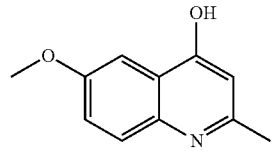

Prepared pursuant to *Euro. J. Med. Chem.* 2010, 3803.

4-Chloro-6-methoxy-2-methylquinoline: *Euro. J. Med. Chem.* 2010, 3803

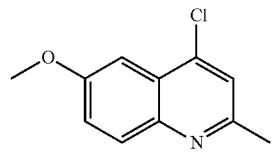

Prepared pursuant to *Euro. J. Med. Chem.* 2010, 3803.

Lyso-27:

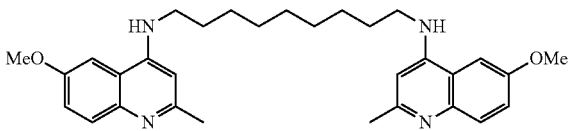 [SMILES: COc1ccc2nc(C)cc(NCCCCCCCCCNc3cc(C)nc4ccc(OC)cc34)c2c1]

To a 20 mL microwave vial was added 1,9-diamino nonane (0.34 g, 2.18 mmol, 1.00 equiv.), 4-Chloro-6-methoxy-2-methylquinoline (1.02 g, 4.90 mmol, 2.25 equiv.), BINAP (0.07 g, 0.12 mmol, 0.05 equiv.), Pd(OAc)$_2$ (0.02 g, 0.07 mmol, 0.03 equiv.) and K$_3$PO$_4$ (1.39 g, 6.53 mmol, 3.00 equiv.). The vial was sealed and placed under argon. Fully degasses solvent dioxane:water (10:1, 7 mL, 0.3 M) was added and the reaction was heated to 100° C. for 16 hours. The reaction was followed by TLC and NMR. The reaction was allowed to cool to room temperature and filtered on celite, washing through with MeOH (100 mL). The filtrate was concentrated to give 0.87 g (crude yield 80%) of an impure brown solid. This material was purified via flash column chromatography (eluent: EtOAc:MeOH:TEA; 90:9:1) to give the product as an off-white solid (0.43 g, 40% yield). R$_f$=0.25 (EtOAc:MeOH:TEA; 90:9:1).

Lyso-28:

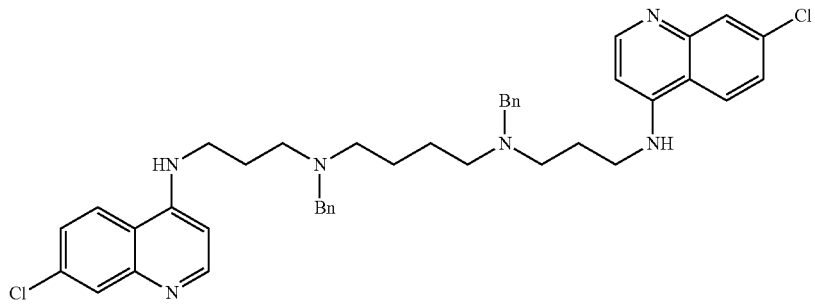

Lyso-20 (0.32 g, 0.62 mmol, 1.00 equiv.) was suspended in DCM (6 mL, 0.1 M). Freshly distilled benzaldehyde (0.4 mL, 3.69 mmol, 6.00 equiv) then sodium triacetoxyborohydride (1.30 g, 6.15 mmol, 10.00 equiv.) were added and the reaction was stirred at room temperature for 12 hours, until TLC analysis showed complete consumption of Lyso-20. A 2 $M_{aq}$ NaOH solution (30 mL) was then added to break up borane salts in the reaction mixture. The resulting mixture was stirred at rt for 1 hour before DCM (30 mL) was added. The resulting biphasic mixture was allowed to settle and separated. The aqueous layer was discarded at this point.

To the DCM solution was added 1 $M_{aq}$ HCl solution (30 mL). The mixture was stirred vigorously at room temperature for 20 minutes, resulting in the formation of a water soluble salt of the desired product. The mixture was allowed to settle and both layers were separated. The aqueous layer was further washed with CHCl$_3$ (2×30 mL) and combined DCM washings were discarded at this point.

Using NH$_4$.OH, the pH of the aqueous layer was adjusted to 11, resulting in the liberation of the free base of the product. The product was extracted into a solvent mixture of DCM (3×30 mL). These combined extracts were washed with brine (100 mL) and dried over Na$_2$SO$_4$. Filtration followed by solvent evaporation afforded a yellow oil (0.35 g, 80% crude yield) which contained impurities. This oil was purified via flash column chromatography [gradient: 100% EtOAc (150 mL); then EtOAc:MeOH:TEA; 90:9:1] to give the product as a yellow solid (0.21 g, 49% yield). $R_f$=0.30 (EtOAc:MeOH:TEA; 90:9:1).

N-(2-Cyanoethyl)-N-(3-cyanopropyl)-benzylamine

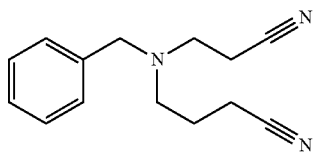 [SMILES: N#CCCCN(CCC#N)Cc1ccccc1]

Prepared pursuant to the procedure of *J. Org. Chem.* 1980, 1589.

N-(3-aminobutyl)-N-(3-aminopropyl)(phenylmethyl) amine: *J. Org. Chem.* 1980, 1589

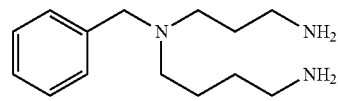 [SMILES: NCCCCN(CCCN)Cc1ccccc1]

Prepared pursuant to the procedure of *J. Org. Chem.* 1980, 1589.

Lyso-29:

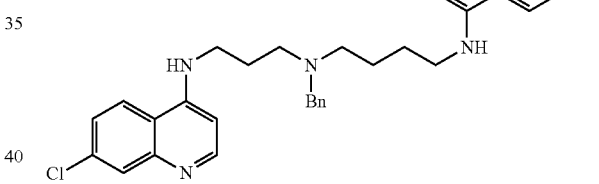

To a microwave tube was added N-(3-aminobutyl)-N-(3-aminopropyl)(phenylmethyl)amine (96.00 mg, 0.41 mmol, 1.00 equiv.), 4-Bromo-7-chloroquinoline (222.00 mg, 0.92 mmol, 2.25 equiv.), BINAP (10.00 mg, 0.02 mmol, 0.04 equiv.), Pd(OAc)$_2$ (2.00 mg, 0.01 mmol, 0.02 equiv.) and K$_3$PO$_4$ (260.00 mg, 1.22 mmol, 3.00 equiv.). The vial was sealed and placed under argon. A solvent mixture of dioxane and water (10:1, 1.5 mL, 0.3 M) was added and the reaction was heated to 100° C. for 13 hours. The reaction was followed by TLC and NMR and once complete it was cooled to room temperature. Following this the reaction was filtered on celite, washing through with MeOH (20 mL). The resulting solution was concentrated to give a yellow oil. This oil was solubilised in CHCl$_3$ (20 mL) and 1 $M_{aq}$ HCl (20 mL) was added. The mixture was stirred vigorously at room temperature for 30 minutes, affording the corresponding water soluble HCl-salt of the product. The mixture was allowed to settle and the resulting layers were separated. The aqueous layer, containing the product, was further washed with CHCl$_3$ (2×20 mL). These combined organic washings were discarded at this point.

Using NH$_4$.OH, the pH of the aqueous layer was adjusted to 11, resulting in the liberation of the free base of the product. The product was extracted into CHCl$_3$ (3×20 mL). These combined extracts were washed with brine (60 mL)

and dried over Na$_2$SO$_4$. Filtration followed by solvent evaporation afforded the product as a yellow solid (112.00 mg, 49% yield). R$_f$=0.60 (EtOAc:MeOH:TEA; 80:15:5).
Lyso-30:

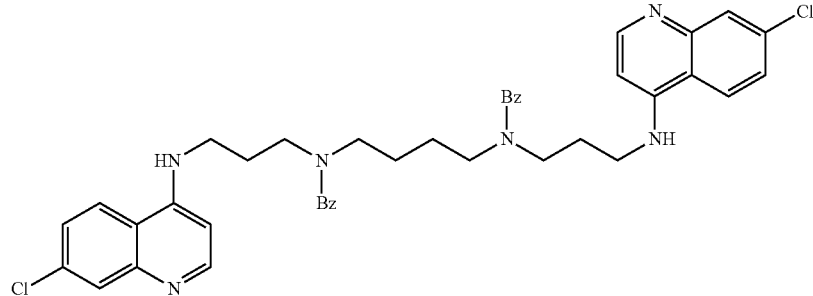

Under argon, Lyso-20 (0.25 g, 0.47 mmol, 1.00 equiv.) was dissolved in anhydrous pyridine (4.7 mL, 0.1 M) and freshly distilled benzoyl chloride (0.3 mL, 2.37 mmol, 5.00 equiv.) was added. The reaction was stirred at room temperature for 2 hours, until TLC analysis showed complete consumption of Lyso-20. Water (20 mL) and CHCl$_3$ (20 mL) were then added to the reaction mixture and stirring was maintained for a further 30 minutes. The layers of this biphasic mixture were then separated. Following this the aqueous layer was further extracted with CHCl$_3$ (2×10 mL). At this point the aqueous layer was discarded and the CHCl$_3$ extracts were combined.

To the CHCl$_3$ solution (containing the product) was added 1 M$_{aq}$ HCl (40 mL). The resulting mixture was stirred vigorously at room temperature for 30 minutes, resulting in the formation of the corresponding water soluble HCl-salt of the product. The mixture was allowed to settle and the resulting layers were separated. The aqueous layer, containing the product, was further washed with CHCl$_3$ (2×20 mL). These combined organic washings were discarded at this point.

Using NH$_4$.OH, the pH of the aqueous layer was adjusted to 11, resulting in the liberation of the free base of the product. The product was extracted into CHCl$_3$ (3×15 mL). These combined extracts were washed with brine (60 mL) and dried over Na$_2$SO$_4$. Filtration followed by solvent evaporation afforded the product as a white foam (0.13 g, 37% yield). R$_f$=0.40 (EtOAc:MeOH:TEA; 80:15:5).
Lyso-31:

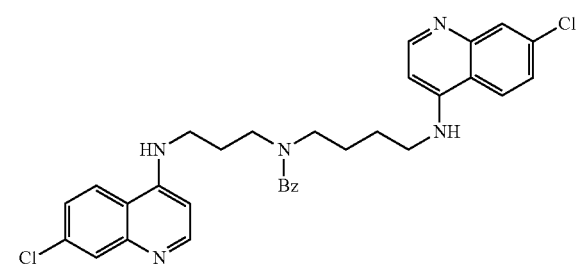 [SMILES: Clc1ccc2c(NCCCCN(CCCNc3ccnc4cc(Cl)ccc34)Cc3ccccc3)ccnc2c1]

Under argon, Lyso-21 (0.21 g, 0.45 mmol, 1.00 equiv.) was dissolved in anhydrous pyridine (4.5 mL, 0.1 M) and freshly distilled benzoyl chloride (0.3 mL, 2.27 mmol, 5.00 equiv.) was added. The reaction was stirred at room temperature for 2 hours, until TLC analysis showed complete consumption of Lyso-21. Water (10 mL) and CHCl$_3$ (10 mL) were then added to the reaction mixture and stirring was maintained for a further 30 minutes. The layers of this biphasic mixture were then separated. Following this the aqueous layer was further extracted with CHCl$_3$ (2×10 mL). At this point the aqueous layer was discarded and the CHCl$_3$ extracts were combined.

To the CHCl$_3$ solution (containing the product) was added 1 M$_{aq}$ HCl (30 mL) The resulting mixture was stirred vigorously at room temperature for 30 minutes, resulting in the formation of the corresponding water soluble HCl-salt of the product. The mixture was allowed to settle and the resulting layers were separated. The aqueous layer, containing the product, was further washed with CHCl$_3$ (2×10 mL). These combined organic washings were discarded at this point.

Using NH$_4$.OH, the pH of the aqueous layer was adjusted to 11, resulting in the liberation of the free base of the product. The product was extracted into CHCl$_3$ (3×15 mL). These combined extracts were washed with brine (60 mL) and dried over Na$_2$SO$_4$. Filtration followed by solvent evaporation afforded the 0.20 g (77% crude yield) of a red oil, which contained impurities. The material obtained was purified via flash column chromatography (eluent: EtOAc:MeOH:TEA; 84:15:1) to give the product as an orange solid (0.14 g, 55% yield). R$_f$=0.45 (EtOAc:MeOH:TEA; 80:15:5).

N-(tert-butylcarbonyl)-3-hydroxypropylamine

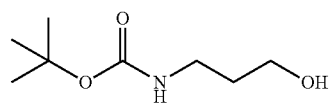

Prepared pursuant to the procedure of *J. Med. Chem.* 2009, 7029.

N-(tert-butylcarbonyl)-3-amino-propionaldehyde

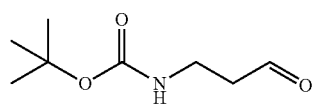

Prepared pursuant to the procedure of *J. Med. Chem.* 2009, 7029.

Compound XX1

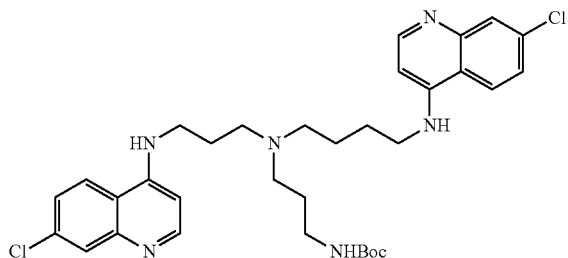 [SMILES: CC(C)(C)OC(=O)NCCCN(CCCCNc1ccnc2cc(Cl)ccc12)CCCNc1ccnc2cc(Cl)ccc12]

Lyso-21 (0.30 g, 0.64 mmol, 1.00 equiv.) was dissolved in DCM (13 mL, 0.05 M). N-(tert-butylcarbonyl)-3-aminopropionaldehyde (0.33 g, 1.92 mmol, 3.00 equiv.), then sodium triacetoxyborohydride (0.73 g, 3.84 mmol, 6.00 equiv.) was added and the reaction was stirred at room temperature for 12 hours. At this point, TLC analysis showed complete consumption of Lyso-21. A 2 $M_{aq}$ NaOH solution (30 mL) was added to break up borane salts in the reaction mixture. The resulting mixture was stirred at rt for 1 hour before DCM (20 mL) was added. The resulting biphasic mixture was allowed to settle and separated. The aqueous layer was discarded at this point.

To the DCM solution was added 1 $M_{aq}$ HCl solution (30 mL). The mixture was stirred vigorously at room temperature for 20 minutes, resulting in the formation of a water soluble salt of the desired product. The mixture was allowed to settle and both layers were separated.

The aqueous layer was further washed with DCM (2×30 mL) and combined DCM washings were then discarded.

Using $NH_4.OH$, the pH of the aqueous layer was adjusted to 11, resulting in the liberation of the free base of the product. The product was extracted into DCM (3×30 mL). These combined extracts were washed with brine (100 mL) and dried over $Na_2SO_4$. Filtration followed by solvent evaporation afforded a white foam which contained some impurities. This foam was purified via flash column chromatography (eluent: gradient, 100% EtOAc→EtOAc: MeOH:TEA; 80:15:5) to give the product as a white solid (0.23 g, 57% yield). $R_f$=0.50 (EtOAc:MeOH:TEA; 80:15:5).

Compound XX2

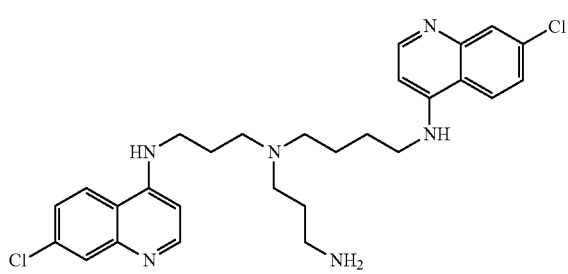 [SMILES: NCCCN(CCCCNc1ccnc2cc(Cl)ccc12)CCCNc1ccnc2cc(Cl)ccc12]

A solution of the compound from above (Compound XX1) (0.21 g, 0.34 mmol, 1.00 equiv.) in DCM (3.5 mL, 0.1 M) was treated with TFA (2 mL, 26.118 mmol, 77.00 equiv.). The resulting reaction was stirred at room temperature and followed by TLC. After 4 hrs, the reaction was found to have reached completion and was quenched via the addition of saturated $NaHCO_3$ solution. Once the reaction mixture was neutralised, it was further basified to pH 11 using 2 $M_{aq}$ NaOH solution. The now alkaline mixture was extracted with a solvent mixture of $CHCl_3$ and i-PrOH (4:1; 3×40 mL). Combined organic extracts were washed with brine (100 mL) and dried over $Na_2SO_4$. Filtration followed by solvent evaporation afforded the product as a yellow solid (0.13 g, 75% yield). $R_1$=0.00 (EtOAc:MeOH:TEA; 80:15:5).

Lyso-32:

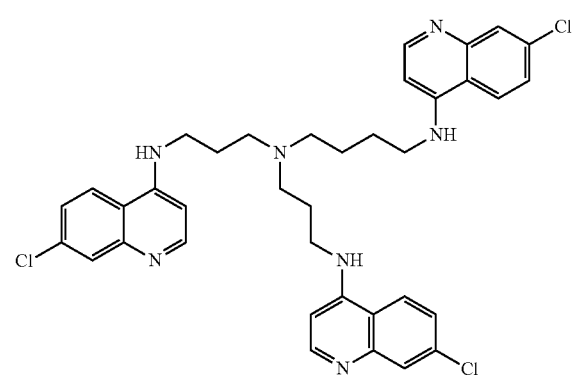 [SMILES: Clc1ccc2c(NCCCCN(CCCNc3ccnc4cc(Cl)ccc34)CCCNc3ccnc4cc(Cl)ccc34)ccnc2c1]

To a microwave tube was added compound XX2 (133.00 mg, 0.25 mmol, 1.00 equiv.), 4-Bromo-7-chloroquinoline (86.00 mg, 0.35 mmol, 1.40 equiv.), BINAP (8.00 mg, 0.01 mmol, 0.05 equiv.), $Pd(OAc)_2$ (2.00 g, 0.008 mmol, 0.03 equiv.) and $K_3PO_4$ (107.00 g, 0.51 mmol, 2.00 equiv.). The vial was sealed and placed under argon. A solvent mixture of dioxane and water (10:1, 1.0 mL, 0.3 M) was added and the reaction was heated to 120° C. for 13 hours. The reaction was followed by TLC and NMR and once complete it was cooled to room temperature. Following this the reaction was filtered on celite, washing through with MeOH (50 mL). The resulting solution was concentrated to give 223.00 mg of a brown solid. This solid was solubilised in $CHCl_3$ (30 mL) and 1 $M_{aq}$ HCl (30 mL) was added. The mixture was stirred vigorously at room temperature for 30 minutes, affording the corresponding water soluble HCl-salt of the product. The mixture was allowed to settle and the resulting layers were separated. The aqueous layer, containing the product, was further washed with $CHCl_3$ (2×30 mL). These combined organic washings were discarded at this point.

Using $NH_4.OH$, the pH of the aqueous layer was adjusted to 11, resulting in the liberation of the free base of the product. The product was extracted into a solvent mixture of $CHCl_3$ and i-PrOH (4:1; 3×50 mL). These combined extracts were washed with brine (150 mL) and dried over $Na_2SO_4$. Filtration followed by solvent evaporation afforded 155.00 mg (89% crude yield) of a white foam which contained some starting material. This foam was purified via flash column chromatography (eluent: gradient EtOAc:MEOH:TEA; 90:9:1→EtOAc:MeOH:TEA; 85:15:5) to give the product as an orange solid (77.00 mg, 44% yield). $R_f$=0.60 (EtOAc: MeOH:TEA; 80:15:5).

Compound XX3

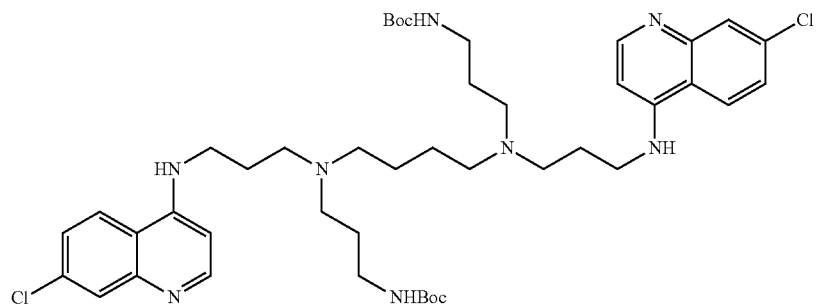 [SMILES: CC(C)(C)OC(=O)NCCCN(CCCCN(CCCNC(=O)OC(C)(C)C)CCCNc1ccnc2cc(Cl)ccc12)CCCNc1ccnc2cc(Cl)ccc12]

Lyso-20 (0.23 g, 0.43 mmol, 1.00 equiv.) was dissolved in DCM (9 mL, 0.05 M). N-(tert-butylcarbonyl)-3-amino-propionaldehyde (0.50 g, 2.86 mmol, 6.00 equiv.), then sodium triacetoxyborohydride (0.91 g, 4.31 mmol, 10.00 equiv.) was added and the reaction was stirred at room temperature for 12 hours. At this point, TLC analysis showed complete consumption of Lyso-20. A 2 $M_{aq}$ NaOH solution (30 mL) was added to break up borane salts in the reaction mixture. The resulting mixture was stirred at rt for 1 hour before DCM (20 mL) was added. The resulting biphasic mixture was allowed to settle and separated. The aqueous layer was discarded at this point.

To the DCM solution was added 1 $M_{aq}$ HCl solution (30 mL). The mixture was stirred vigorously at room temperature for 20 minutes, resulting in the formation of a water soluble salt of the desired product. The mixture was allowed to settle and both layers were separated. The aqueous layer was further washed with DCM (2×30 mL) and combined DCM washings were then discarded.

Using $NH_4.OH$, the pH of the aqueous layer was adjusted to 11, resulting in the liberation of the free base of the product. The product was extracted into DCM (3×30 mL). These combined extracts were washed with brine (100 mL) and dried over $Na_2SO_4$. Filtration followed by solvent evaporation afforded the product as a white foam (0.29 g, 81% yield). $R_f$=0.50 (EtOAc:MeOH:TEA; 80:15:5).

Compound XX4

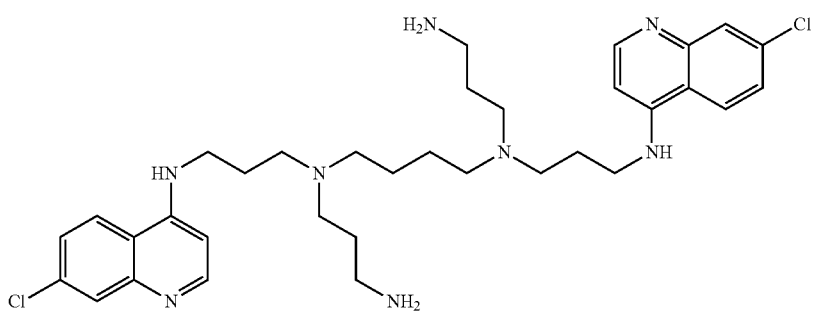 [SMILES: NCCCN(CCCCN(CCCN)CCCNc1ccnc2cc(Cl)ccc12)CCCNc1ccnc2cc(Cl)ccc12]

A solution of Compound XX3 (0.28 g, 0.33 mmol, 1.00 equiv.) in DCM (3.3 mL, 0.1 M) was treated with TFA (2 mL, 26.118 mmol, 79.00 equiv.). The resulting reaction was stirred at room temperature and followed by TLC. After 4 hrs, the reaction was found to have reached completion and was quenched via the addition of saturated $NaHCO_3$ solution. Once the reaction mixture was neutralised, it was further basified to pH 11 using 2 $M_{aq}$ NaOH solution. The now alkaline mixture was extracted with a solvent mixture of $CHCl_3$ and i-PrOH (4:1; 3×40 mL). Combined organic extracts were washed with brine (100 mL) and dried over $Na_2SO_4$. Filtration followed by solvent evaporation afforded the product as a yellow solid (0.09 g, 42% yield). $R_f$=0.00 (EtOAc:MeOH:TEA; 80:15:5).

Lyso-33:

separated. The aqueous layer, containing the product, was further washed with $CHCl_3$ (2×30 mL). These combined organic washings were discarded at this point.

Using $NH_4.OH$, the pH of the aqueous layer was adjusted to 11, resulting in the liberation of the free base of the product. The product was extracted into a solvent mixture of $CHCl_3$ and i-PrOH (4:1; 3×50 mL). These combined extracts were washed with brine (150 mL) and dried over $Na_2SO_4$. Filtration followed by solvent evaporation afforded 85.00 mg (63% crude yield) of a brown foam which contained some starting material. This foam was purified via flash column chromatography (eluent: $CHCl_3$:MeOH:TEA; 85:15:5) to give the product as a white solid (49.00 mg, 36% yield). $R_f$=0.55 ($CHCl_3$:MeOH:TEA; 80:15:5).

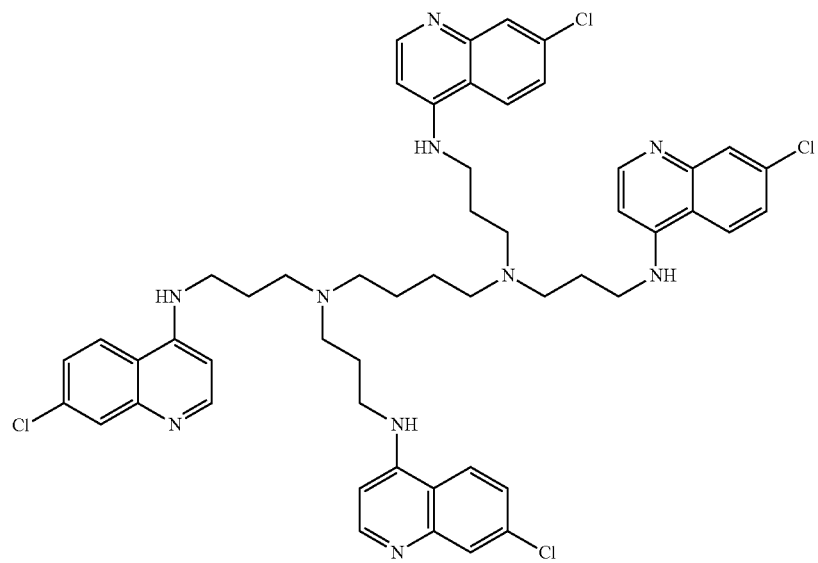 [SMILES: Clc1ccc2c(NCCCN(CCCCN(CCCNc3ccnc4cc(Cl)ccc34)CCCNc3ccnc4cc(Cl)ccc34)CCCNc3ccnc4cc(Cl)ccc34)ccnc2c1]

To a microwave tube was added compound XX3 (90.00 mg, 0.14 mmol, 1.00 equiv.), 4-Bromo-7-chloroquinoline (48.00 mg, 0.20 mmol, 1.40 equiv.), BINAP (4.00 mg, 0.007 mmol, 0.05 equiv.), $Pd(OAc)_2$ (1.00 mg, 0.004 mmol, 0.03 equiv.) and $K_3PO_4$ (60.00 mg, 0.28 mmol, 2.00 equiv.). The vial was sealed and placed under argon. A solvent mixture of dioxane and water (10:1, 0.5 mL, 0.3 M) was added and the reaction was heated to 120° C. for 13 hours. The reaction was followed by TLC and NMR and once complete it was cooled to room temperature. Following this, the reaction was filtered on celite, washing through with MeOH (50 mL). The resulting solution was concentrated to give 139.00 mg of a brown solid. This solid was solubilised in $CHCl_3$ (30 mL) and 1 $M_{aq}$ HCl (30 mL) was added. The mixture was stirred vigorously at room temperature for 30 minutes, affording the corresponding water soluble HCl-salt of the product. The mixture was allowed to settle and the resulting layers were N,N-Bis(3-cyanopropyl)-benzylamine

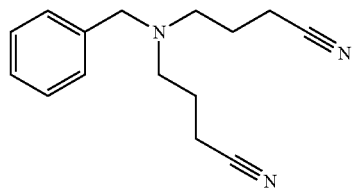 [SMILES: N#CCCCN(CCCC#N)Cc1ccccc1]

Prepared by the method described in *Bioorg. Med. Chem. Lett.* 2003. 3267.

N,N-Bis(4-aminobutyl)-benzylamine

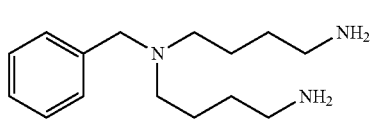 [SMILES: NCCCCN(CCCCN)Cc1ccccc1]

Prepared by the method described in *Bioorg. Med. Chem. Lett.* 2003. 3267.

Bis-(4-aminobutyl)-amine

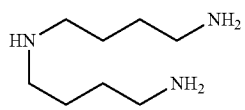 [SMILES: NCCCCNCCCCN]

Prepared by the method described in *Bioorg. Med. Chem. Lett.* 2003. 3267.

Lyso-38:

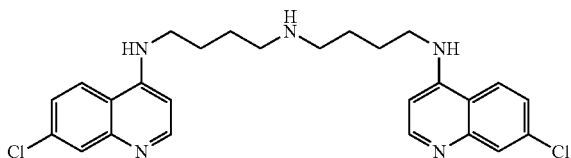 [SMILES: Clc1ccc2c(NCCCCNCCCCNc3ccnc4cc(Cl)ccc34)ccnc2c1]

To a microwave tube was added bis-(4-aminobutyl)-amine (0.31 g, 1.96 mmol, 1.00 equiv.), 4-bromo-7-chloro-quinoline (1.06 g, 4.41 mmol, 2.25 equiv.), BINAP (0.09 g, 0.15 mmol, 0.08 equiv.), Pd(OAc)$_2$ (0.02 g, 0.10 mmol, 0.05 equiv.) and K$_3$PO$_4$ (1.90 g, 7.84 mmol, 4.00 equiv.). The vial was sealed and placed under argon. A solvent mixture of dioxane and water (10:1, 6.5 mL, 0.3 M) was added and the reaction was heated to 120° C. for 12 hours. The reaction was followed by TLC and NMR and once complete it was cooled to room temperature. Following this, the reaction was filtered on celite, washing through with MeOH (50 mL). The resulting solution was concentrated under reduced pressure. This solid was solubilised in DCM (40 mL) and 1 M$_{aq}$ HCl (40 mL) was added. The mixture was stirred vigorously at room temperature for 30 minutes, affording the corresponding water soluble HCl-salt of the product. The mixture was allowed to settle and the resulting layers were separated. The aqueous layer, containing the product, was further washed with CHCl$_3$ (2×40 mL). These combined organic washings were discarded at this point.

Using NH$_4$.OH, the pH of the aqueous layer was adjusted to 11, resulting in the liberation of the free base of the product. The product was extracted into a solvent mixture of CHCl$_3$ and i-PrOH (4:1; 3×40 mL). These combined extracts were washed with brine (120 mL) and dried over Na$_2$SO$_4$. Filtration followed by solvent evaporation afforded the product as a white solid (0.44 g, 46% yield). R$_f$=0.10 (EtOAc:MeOH:TEA; 80:15:5).

Lyso-39:

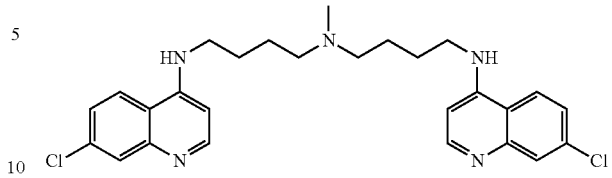

A solution of Lyso-38 (0.13 g, 0.27 mmol, 1.00 equiv.) in DCM (3 mL, 0.1 M) was treated with formaldehyde 37 wt % (0.04 g, 0.55 mmol, 2.00 equiv.) then sodium triacetoxyborohydride (0.23 g, 1.09 mmol, 4.00 equiv.). The resulting reaction was stirred at room temperature for 6 hours. Following this, 2 M$_{aq}$ NaOH (15 mL) was added to the reaction mixture to break up any borane salts. This mixture was stirred at room temperature for 1 hour before the product was extracted into CHCl$_3$ (3×15 mL). The basic aqueous layer was discarded at this point.

To the chloroform solution was added 1 M$_{aq}$ HCl (40 mL). The mixture was stirred vigorously at room temperature for 30 minutes, affording the corresponding water soluble HCl-salt of the product. The mixture was allowed to settle and the resulting layers were separated. The aqueous layer, containing the product, was further washed with CHCl$_3$ (2×15 mL). These combined organic washings were discarded at this point.

Using NH$_4$.OH, the pH of the aqueous layer was adjusted to 11, resulting in the liberation of the free base of the product. The product was extracted into a solvent mixture of CHCl$_3$ and i-PrOH (4:1; 3×15 mL). These combined extracts were washed with brine (50 mL) and dried over Na$_2$SO$_4$. Filtration followed by solvent evaporation afforded the product as a white solid (0.08 g, 60% yield). R$_f$=0.30 (EtOAc:MeOH:TEA; 80:15:5).

N,N-Bis(4-cyanobutyl)-benzylamine

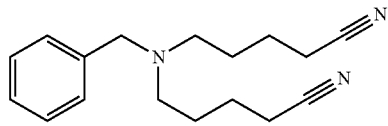 [SMILES: N#CCCCCN(CCCCC#N)Cc1ccccc1]

Prepared by the method described in *Bioorg. Med. Chem. Lett.* 2003. 3267.

N,N-Bis(5-aminopentyl)-benzylamine

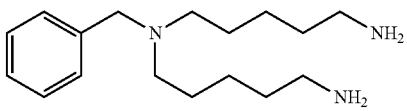

Prepared by the method described in *Bioorg. Med. Chem. Lett.* 2003. 3267.

Bis-(4-aminopentyl)-amine: [Bioorg. Med. Chem. Lett. 2003. 3267]

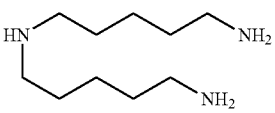

Prepared by the method described in Bioorg. Med. Chem. Lett. 2003. 3267.

Lyso-40:

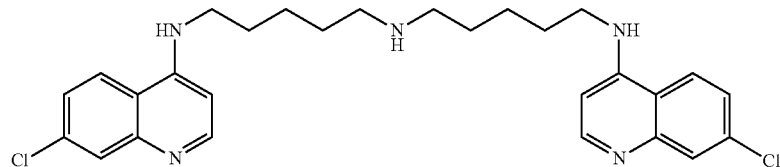 [SMILES: Clc1ccc2c(NCCCCCNCCCCCNc3ccnc4cc(Cl)ccc34)ccnc2c1]

To a microwave tube was added Bis-(4-aminopentyl)-amine (0.40 g, 1.43 mmol, 1.00 equiv.), 4-bromo-7-chloro-quinoline (0.78 g, 3.23 mmol, 2.25 equiv.), BINAP (0.07 g, 0.11 mmol, 0.08 equiv.), Pd(OAc)$_2$ (0.02 g, 0.07 mmol, 0.05 equiv.) and K$_3$PO$_4$ (1.22 g, 5.74 mmol, 4.00 equiv.). The vial was sealed and placed under argon. A solvent mixture of dioxane and water (10:1, 5 mL, 0.3 M) was added and the reaction was heated to 120° C. for 12 hours. The reaction was followed by TLC and NMR and once complete it was cooled to room temperature. Following this, the reaction was filtered on celite, washing through with MeOH (50 mL). The resulting solution was concentrated under reduced pressure. This solid was solubilised in CHCl$_3$ (20 mL) and 1 M$_{aq}$ HCl (20 mL) was added. The mixture was stirred vigorously at room temperature for 30 minutes, affording the corresponding water soluble HCl-salt of the product. The mixture was allowed to settle and the resulting layers were separated. The aqueous layer, containing the product, was further washed with CHCl$_3$ (2×20 mL). These combined organic washings were discarded at this point.

Using NH$_4$.OH, the pH of the aqueous layer was adjusted to 11, resulting in the liberation of the free base of the product. The product was extracted into a solvent mixture of CHCl$_3$ and i-PrOH (4:1; 3×30 mL). These combined organic extracts were washed with brine (100 mL) and dried over Na$_2$SO$_4$. Filtration followed by solvent evaporation afforded the product as a yellow solid (0.51 g, 69% yield). R$_f$=0.05 (EtOAc:MeOH:TEA; 84:15:1).

Lyso-41:

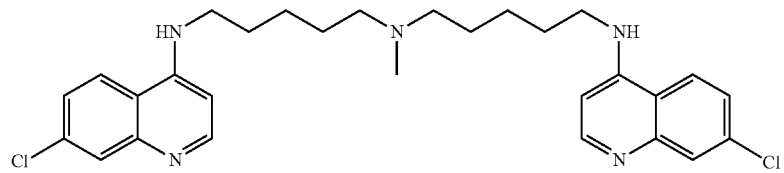 [SMILES: CN(CCCCCNc1ccnc2cc(Cl)ccc12)CCCCCNc1ccnc2cc(Cl)ccc12]

A solution of Lyso-40 (0.45 g, 0.88 mmol, 1.00 equiv.) in DCM (9 mL, 0.1 M) was treated with formaldehyde 37 wt % (0.14 g, 1.76 mmol, 2.00 equiv.) then sodium triacetoxyborohydride (0.74 g, 3.51 mmol, 4.00 equiv.). The resulting reaction was stirred at room temperature for 6 hours. Following this, 2 M$_{aq}$ NaOH (30 mL) was added to the reaction mixture to break up any borane salts. This mixture was stirred at room temperature for 1 hour before the product was extracted into CHCl$_3$ (3×30 mL). The basic aqueous layer was discarded at this point.

To the chloroform solution was added 1 M$_{aq}$ HCl (40 mL). The mixture was stirred vigorously at room temperature for 30 minutes, affording the corresponding water soluble HCl-salt of the product. The mixture was allowed to settle and the resulting layers were separated. The aqueous layer, containing the product, was further washed with CHCl$_3$ (2×30 mL). These combined organic washings were discarded at this point.

Using NH$_4$.OH, the pH of the aqueous layer was adjusted to 11, resulting in the liberation of the free base of the product. The product was extracted into a solvent mixture of CHCl$_3$ and i-PrOH (4:1; 3×30 mL). These combined extracts were washed with brine (100 mL) and dried over Na$_2$SO$_4$. Filtration followed by solvent evaporation afforded the product as a white solid (0.39 g, 85% yield). R$_f$=0.10 (EtOAc:MeOH:TEA; 84:15:1).

Lys 42:

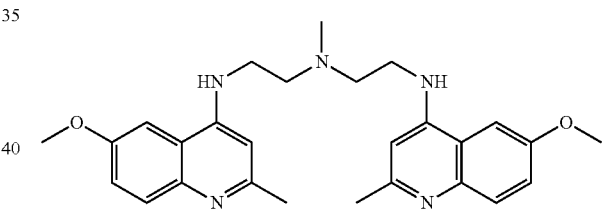

To a vial was added 4-Chloro-6-methoxy-2-methylquinoline (508.00 mg, 2.45 mmol, 2.40 equiv,), BINAP (95.00 mg, 0.15 mmol, 0.15 equiv.), Pd(OAc)$_2$ (17.00 mg, 0.08 mmol, 0.075 equiv.), finely ground K$_3$PO$_4$ (867.00 mg, 4.09 mmol, 4.00 equiv.) and N-(2-aminoethyl)-N-methyl-1,2-ethanediamine (130.0 μL, 1.02 mmol, 1.00 equiv.). The reagents were placed under a blanket of Argon; then a mixture of degassed dioxane and water (4 mL, 10:1) was added. The reaction vial was sealed and heated to 120° C. for 12 hours. The reaction was then cooled to room temperature and filtered on a pad of celite; washing with chloroform (3×10 mL). Combined organic layers were acidified to pH 1 using 1M aqueous HCl solution (4 mL, 4.09 mmol, 4.00 equiv.) and diluted with water (20 mL). The resulting biphasic mixture was separated and the water layer was washed with chloroform (2×15 mL). The pH of the aqueous layer was adjusted to 11 using ammonium hydroxide. The now alkaline mixture was washed with chloroform (3×20 mL). These 3 chloroform extracts were combined, washed with brine, dried over Na$_2$SO$_4$ and concentrated to give the product as an off-white solid (415.00 mg, 88% yield, ≥95% purity). Recrystallisation from EtOAc afforded off-white crystals (0.225 g, 48% recrystallised yield). R$_f$=0.45 (CHCl$_3$:MeOH:TEA; 85:10:5); Mp=205-206° C. with decomp. (EtOAc).

Lys 43:

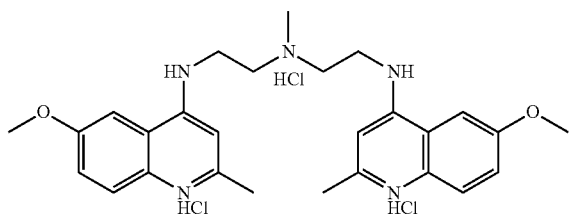

A solution of Lyso-42 (1 equiv.) in DCM was treated with a 1 M solution of HCl in diethyl ether (10 equiv.). HPLC analysis of Lyso-43 showed >99% purity.

Lys 44:

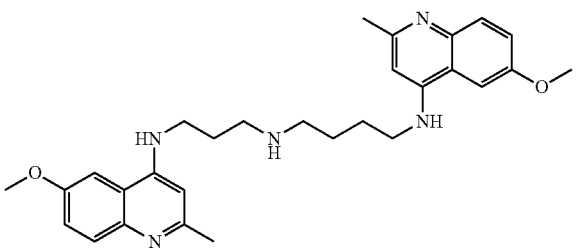

To a vial was added 4-Chloro-6-methoxy-2-methylquinoline (559.00 mg, 2.70 mmol, 2.40 equiv,), BINAP (105.00 mg, 0.17 mmol, 0.15 equiv.), Pd(OAc)$_2$ (19.00 mg, 0.08 mmol, 0.075 equiv.), finely ground K$_3$PO$_4$ (1061.00 mg, 5.00 mmol, 4.00 equiv.) and spermidine (180.0 µL, 1.13 mmol, 1.00 equiv.). The reagents were placed under a blanket of Argon; then a mixture of degassed dioxane and water (4 mL, 10:1) was added. The reaction vial was sealed and heated to 120° C. for 12 hours. The reaction was then cooled to room temperature and filtered on a pad of celite; washing with chloroform (3×10 mL). Combined organic layers were acidified to pH 1 using 1M aqueous HCl solution (5 mL, 4.5 mmol, 4.00 equiv.) and diluted with water (20 mL). The resulting biphasic mixture was separated and the water layer was washed with chloroform (2×15 mL). The pH of the aqueous layer was adjusted to 11 using ammonium hydroxide. The now alkaline mixture was washed with chloroform (3×20 mL). These 3 chloroform extracts were combined, washed with brine, dried over Na$_2$SO$_4$ and concentrated to give the product as an off-white solid (549.00 mg, 99% yield, ≥90% purity). Recrystallisation from EtOAc afforded off-white crystals (123 mg, 22% recrystallised yield). R$_f$=0.05 (CHCl$_3$:MeOH:TEA; 85:10:5); Mp=198-199° C. with decomp. (EtOAc).

Lys 45:

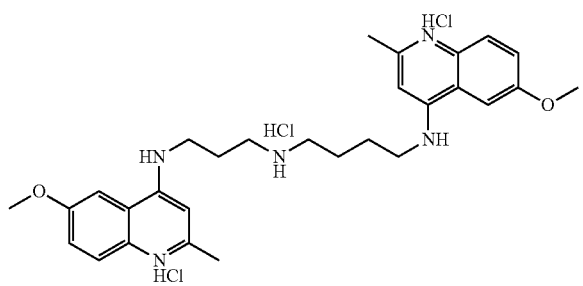

A solution of Lyso-44 (1 equiv.) in DCM was treated with a 1 M solution of HCl in diethyl ether (10 equiv.). HPLC of Lyso-45 analysis showed >97% purity.

Lys 46:

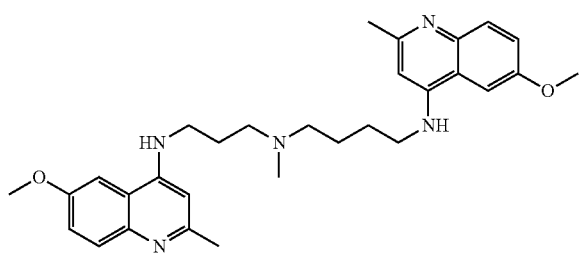

To a stirred mixture of Lys 44 (272.00 mg, 0.56 mmol, 1.00 equiv.) in formic acid (2.2 mL, 0.25 M) was added 37% aqueous formaldehyde (99.8 mg, 1.23 mmol, 2.20 equiv.). The reaction was heated to 100° C. and heating was maintained for 2 hours. TLC analysis revealed that all the starting material had been consumed. The reaction mixture was poured onto ice and basified via the addition of ammonium hydroxide (until pH>9). The now alkaline mixture was extracted with chloroform (3×15 mL). Combined organic extracts were washed with brine and dried over Na$_2$SO$_4$. Filtration followed by solvent evaporation afforded the product as an off-white solid (261.00 mg, 93% yield, ≥85% purity). The material was purified via flash column chromatography (gradient: 100% EtOAc→84:15:1; EtOAc:MeOH:TEA) to give a pure off-white solid (102.00 mg, 36% yield). R$_1$=0.15 (CHCl$_3$:MeOH:TEA; 85:10:5); Mp=140-141° C.

Lys 47:

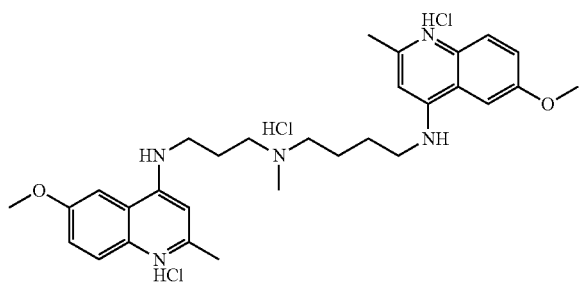

A solution of Lyso-46 (1 equiv.) in DCM was treated with a 1 M solution of HCl in diethyl ether (10 equiv.). HPLC analysis of Lyso-47 showed >99% purity.

Lyso-72:

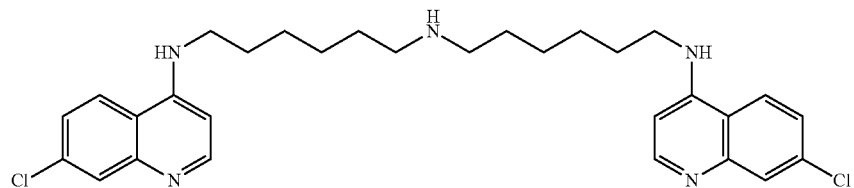 [SMILES: Clc1ccc2c(NCCCCCCNCCCCCCNc3ccnc4cc(Cl)ccc34)ccnc2c1]

To a microwave tube was added Bis-(hexamethyl)-triamine (0.73 g, 3.40 mmol, 1.00 equiv.), 4-bromo-7-chloroquinoline (1.86 g, 7.66 mmol, 2.25 equiv.), BINAP (0.11 g, 0.17 mmol, 0.05 equiv.), Pd(OAc)$_2$ (0.02 g, 0.10 mmol, 0.03 equiv.) and K$_3$PO$_4$ (2.17 g, 10.21 mmol, 3.00 equiv.). The vial was sealed and placed under argon. A solvent mixture of dioxane and water (10:1, 11 mL, 0.3 M) was added and the reaction was heated to 120° C. for 14 hours. The reaction was followed by TLC and NMR and once complete it was cooled to room temperature. Following this, the reaction was filtered on celite, washing through with MeOH (50 mL). The resulting solution was concentrated under reduced pressure. This solid was solubilised in CHCl$_3$ (50 mL) and 1 M$_{aq}$ HCl (50 mL) was added. The mixture was stirred vigorously at room temperature for 30 minutes, affording the corresponding water soluble HCl-salt of the product. The mixture was allowed to settle and the resulting layers were separated. The aqueous layer, containing the product, was further washed with CHCl$_3$ (2×50 mL). These combined organic washings were discarded at this point.

Using NH$_4$.OH, the pH of the aqueous layer was adjusted to 11, resulting in the liberation of the free base of the product. The product was extracted into a solvent mixture of CHCl$_3$ and i-PrOH (4:1; 3×40 mL). These combined organic extracts were washed with brine (120 mL) and dried over Na$_2$SO$_4$. Filtration followed by solvent evaporation afforded the product as a yellow solid (1.66 g, 90% yield). R$_f$=0.10 (EtOAc:MeOH:TEA; 80:15:5); Mp=100-102° C.

Lyso-73:

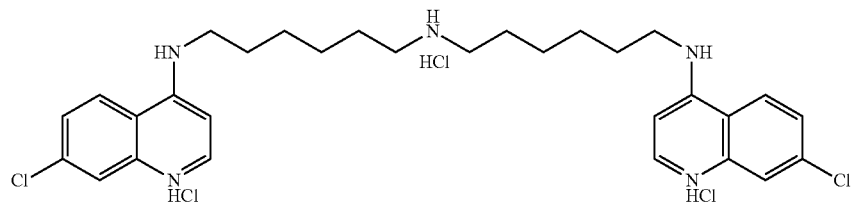

A solution of Lyso-72 (1 equiv.) in DCM was treated with a 1 M solution of HCl in diethyl ether (10 equiv.). HPLC analysis of Lyso-73 showed >99% purity.

Lyso-74:

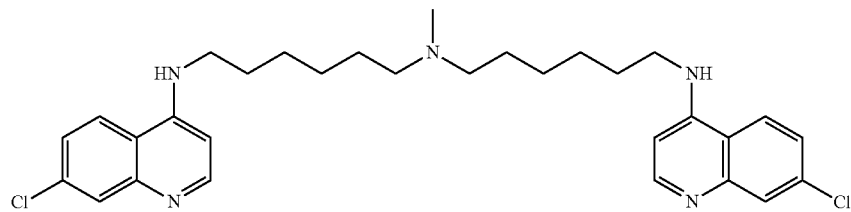 [SMILES: CN(CCCCCCNc1ccnc2cc(Cl)ccc12)CCCCCCNc1ccnc2cc(Cl)ccc12]

A solution of Lyso-72 (0.93 g, 1.73 mmol, 1.00 equiv.) in THF (17 mL, 0.1 M) was treated with formaldehyde 37 wt % (0.28 g, 3.45 mmol, 2.00 equiv.) then sodium triacetoxyborohydride (1.46 g, 6.91 mmol, 4.00 equiv.). The resulting reaction was stirred at room temperature for 4 hours. Following this, 2 M$_{aq}$ NaOH (30 mL) was added to the reaction mixture to break up any borane salts. This mixture was stirred at room temperature for 1 hour before the product was extracted into CHCl$_3$ (30 mL). The basic aqueous layer was discarded at this point.

To the chloroform solution was added 1 M$_{aq}$ HCl (30 mL). The mixture was stirred vigorously at room temperature for 30 minutes, affording the corresponding water soluble HCl-salt of the product. The mixture was allowed to settle and the resulting layers were separated. The aqueous layer, containing the product, was then further washed with CHCl$_3$ (2×30 mL). These combined organic washings were discarded at this point.

Using NH$_4$.OH, the pH of the aqueous layer was adjusted to 11, resulting in the liberation of the free base of the product. The product was extracted into a solvent mixture of CHCl$_3$ and i-PrOH (4:1; 3×30 mL). These combined extracts were washed with brine (120 mL) and dried over Na$_2$SO$_4$. Filtration followed by solvent evaporation afforded the product as a yellow solid (0.34 g, 36% yield). R$_f$=0.35 (EtOAc:MeOH:TEA; 80:15:5); Mp=58-60° C.

Lyso-75:

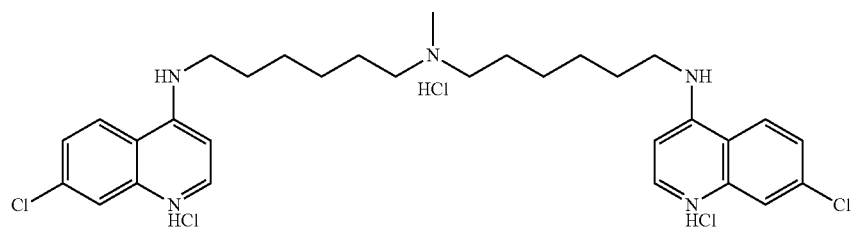

A solution of Lyso-74 (1 equiv.) in DCM was treated with a 1 M solution of HCl in diethyl ether (10 equiv.). HPLC analysis of Lyso-75 showed >99% purity.

Lyso-82:

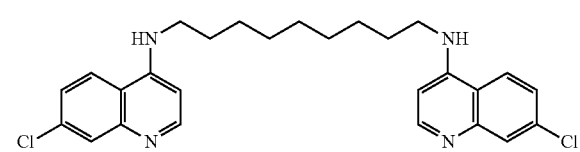 [SMILES: Clc1ccc2c(NCCCCCCCCCNc3ccnc4cc(Cl)ccc34)ccnc2c1]

To a 20 mL microwave vial was added 1,9-diaminononane (0.27 g, 1.72 mmol, 1.00 equiv.), 4-bromo-7-chloroquinoline (1.00 g, 4.12 mmol, 2.40 equiv.), BINAP (0.05 g, 0.09 mmol, 0.05 equiv.), Pd(OAc)$_2$ (0.01 g, 0.05 mmol, 0.03 equiv.) and K$_3$PO$_4$ (1.09 g, 5.15 mmol, 3.00 equiv.). The vial was sealed and placed under argon. Fully degasses solvent dioxane:water (10:1, 6 mL, 0.3 M) was added and the reaction was heated to 120° C. for 12 hours. The reaction was followed by TLC and NMR. The reaction was allowed to cool to room temperature and filtered on celite, washing through with MeOH (100 mL). The filtrate was concentrated to give 1.09 g (crude yield 131%) of an impure solid. This material was purified via flash column chromatography (eluent: Gradient; 100% EtOAc→EtOAc:MeOH:TEA; 90:9:1) to give the product as a white solid (0.40 g, 37% yield). R$_f$=0.40 (EtOAc:MeOH:TEA; 90:9:1); Mp=158-160° C.

Lyso-83:

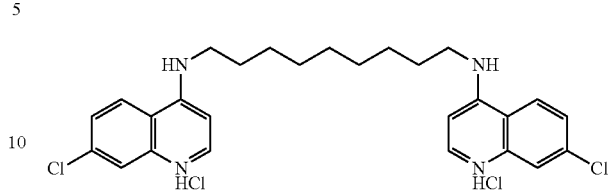

A solution of Lyso-82 (1 equiv.) in DCM was treated with a 1 M solution of HCl in diethyl ether (10 equiv.). HPLC analysis of Lyso-83 showed >90% purity.

Results

The present analogs have been designed to test an important factor: the role of the linker between the two chloroquinoline moieties. Toward that end, we have observed that replacement of the linker of Lys01 with longer linkers, such as spermine (Lys 20 and 25) and spermidine (Lys21 and 26) lead to significant increases in potency. While the spermine linker introduces an additional nitrogen functionality (and an additional positive charge under physiological conditions), the spermidine linker is more similar to the Lys01 linker. However, unlike the Lys01 linker, the spermidine linker is not symmetrical. The spermidine linker contains three and four methylenes, respectively, between the three nitrogen atoms of the triamine linker, while the Lys01 connector contains two methylenes between each of the three nitrogen atoms.

Cytotoxic Activity of Longer and Assymetric Linker Compounds in Cancer Cells.

LN229 glioma cells, and A375P melanoma cells were plated in a 384 well format and compounds CQ, HCQ, and Lys01-Lys41 and 72-75 (structures provided in Appendix A, Chemical Structures) were delivered in concentrations between 0.01-10 micromolar using robotic assisted dispenser. After 72 hours incubation at 37 degrees, Alamar blue was applied and viability was determined using absorbance. Absorbance was normalized to DMSO control, and a log IC50 was estimated using Graphpad Prism software (FIG. 11, Table 1). LN229 cells produced similar data (data not shown). Selected IC50s of the most promising compounds are presented in FIG. 1A. The increased cytotoxicity of longer linker and assymetric compounds was confirmed in a 2 week colony formation assay using 5 different cell lines (FIG. 1B). Analysis of the cytotoxicity findings alone elucidated some key features of potential structure activity relationships. First, substitution of the central nitrogen substitution beyond methyl reduces activity. Second, there was no clear advantage of assymetric versus symmetric linkers (FIG. 2A) with regards to cytotoxicity alone. Third, increasing Linker length from Lys05 was associated with increased activity but beyond a certain threshold of linker carbons, there is no increased potency for these compounds in the alamar blue viability assay (FIG. 2B).

Longer Linker Compounds Localize to the Lysosome.

To confirm that dimeric CQ's with longer linkers retain their presumed lysosomal subcellular localization, Lys21/26 was functionalized into a fluorescent probe by attaching a Cy3 dye to the central nitrogen. This compound referred to as Lys21-Cy3 (FIG. 3A) was used to treat A375 melanoma (FIG. 3B). Costaining with lysotracker green and subsequent fluorescent microscopy allowed the visualization of lysosomal localization for the Lys21 derivative. After 48 hours of treatment lysosomal mass had decreased and the red fluorescence was more cytoplasmic indicative of lysosomal rupture and diffusion of intact compound.

Figure 4:
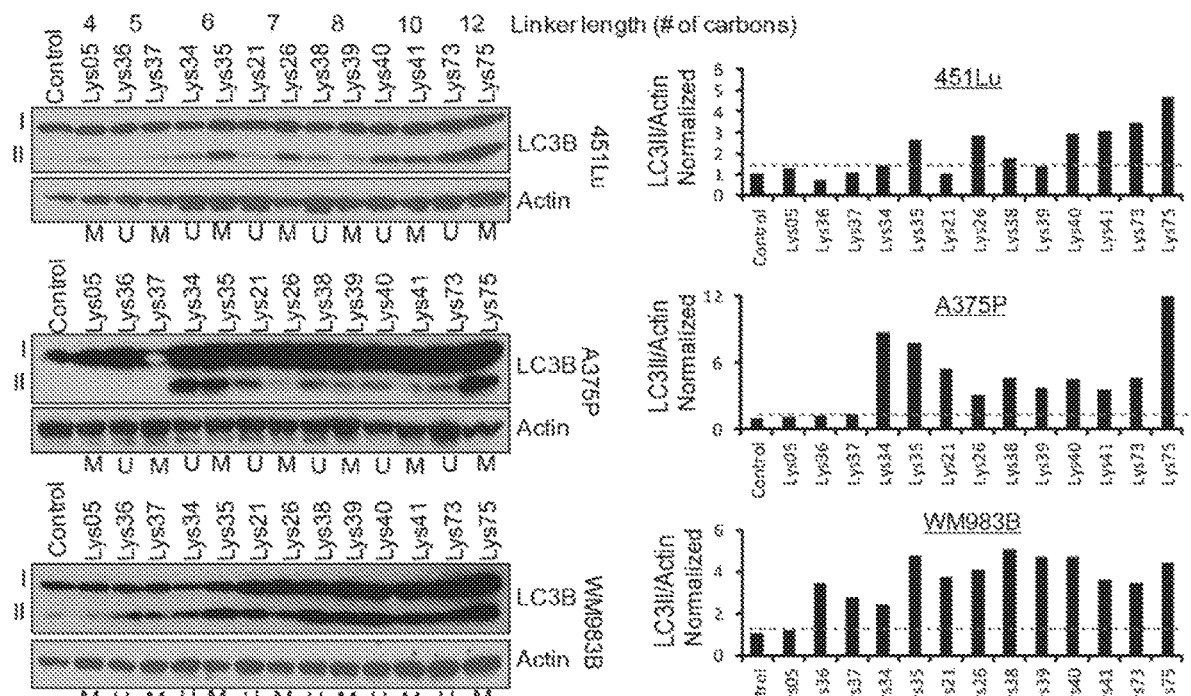
FIG. 4 shows autophagy modulation of dimeric chloroquines with longer linkers in melanoma cell lines. LC3B and actin immunoblotting in 3 different melanoma cell lines. Each compound was administered at 1 uM concentrations for 24 hours. Quantification of LC3II/actin indicates all dimeric CQs with longer linker produced higher levels of LC3II/actin compared with Lys05 (dotted line).
Figure 5:
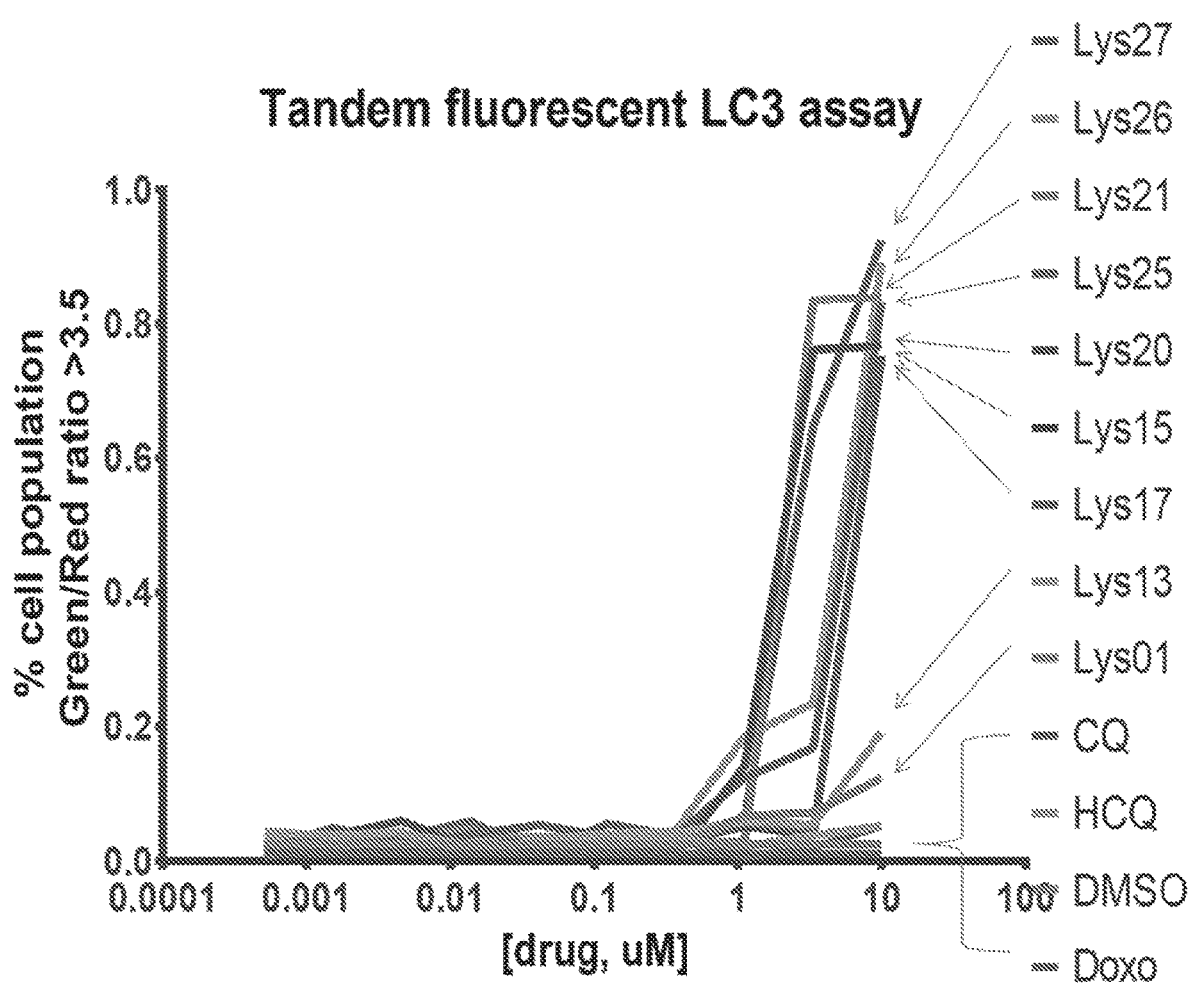
FIG. 5 shows high throughput phenotypic screen of autophagy inhibition for Lys01 derivatives. A375PmCherry-eGFP-LC3 cells were seeded in 384 well plates. Doxorubicin, HCQ, CQ and Lys01-Lys27 (in 0.1% DMSO) were administered through robotic assisted pin tool transfer at concentrations of 0-10 µM. Images were obtained by the Operetta high-content fluorescent microscopy. Image analysis using Harmony software reports fraction of nucleated cells with ratio of >3.5 in cells treated with 10 µM compound.
Figure 6:
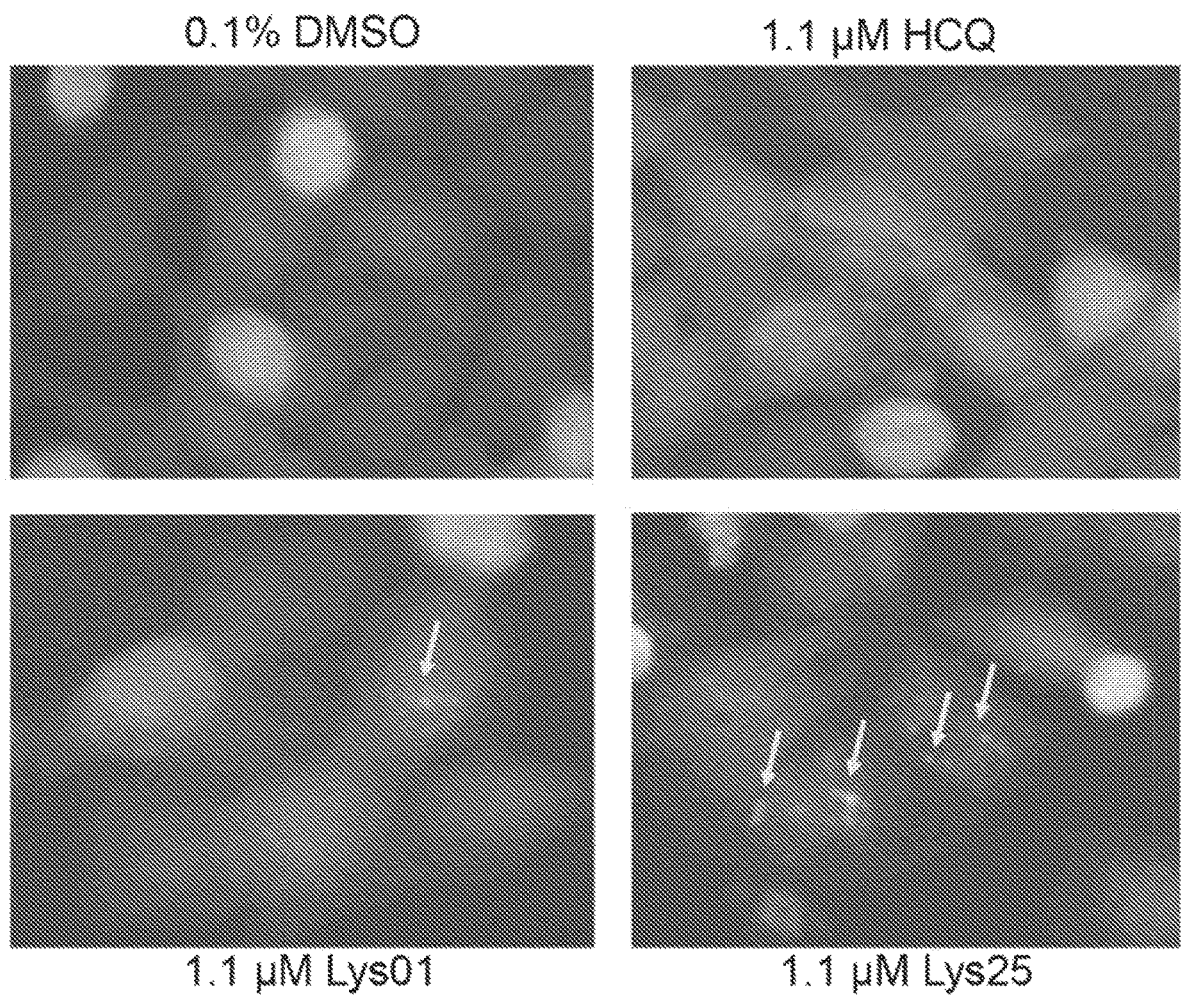
FIG. 6 shows high throughput fluorescence microscopy images of A375P mCherry-eGFP-LC3 melanoma cells treated with indicated chloroquine derivatives.
Figure 7:
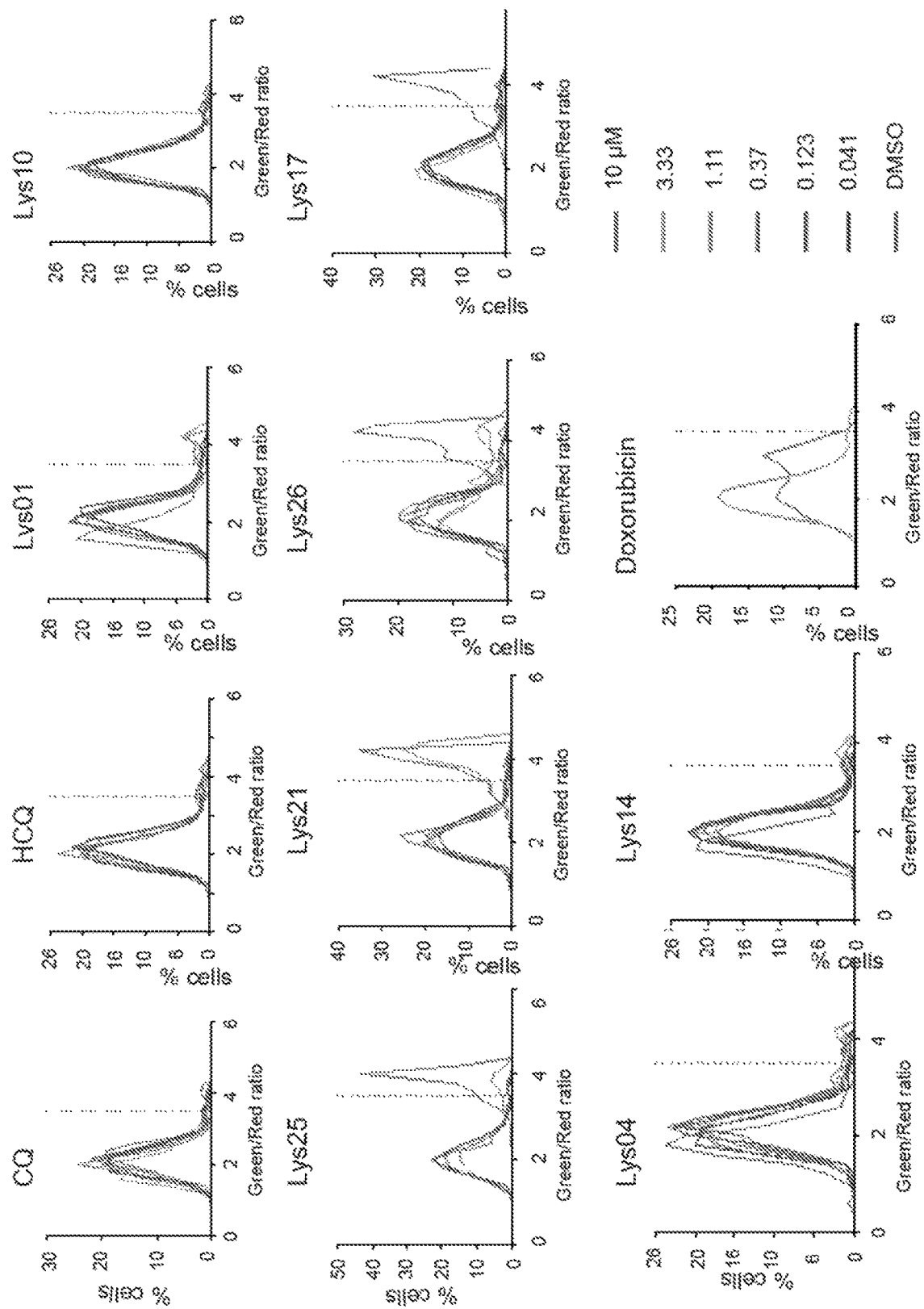
FIG. 7 shows histograms of green/red ratio in Lys01-derivative treated A375PmCherry-GFP-LC3 cells.
Figure 8:
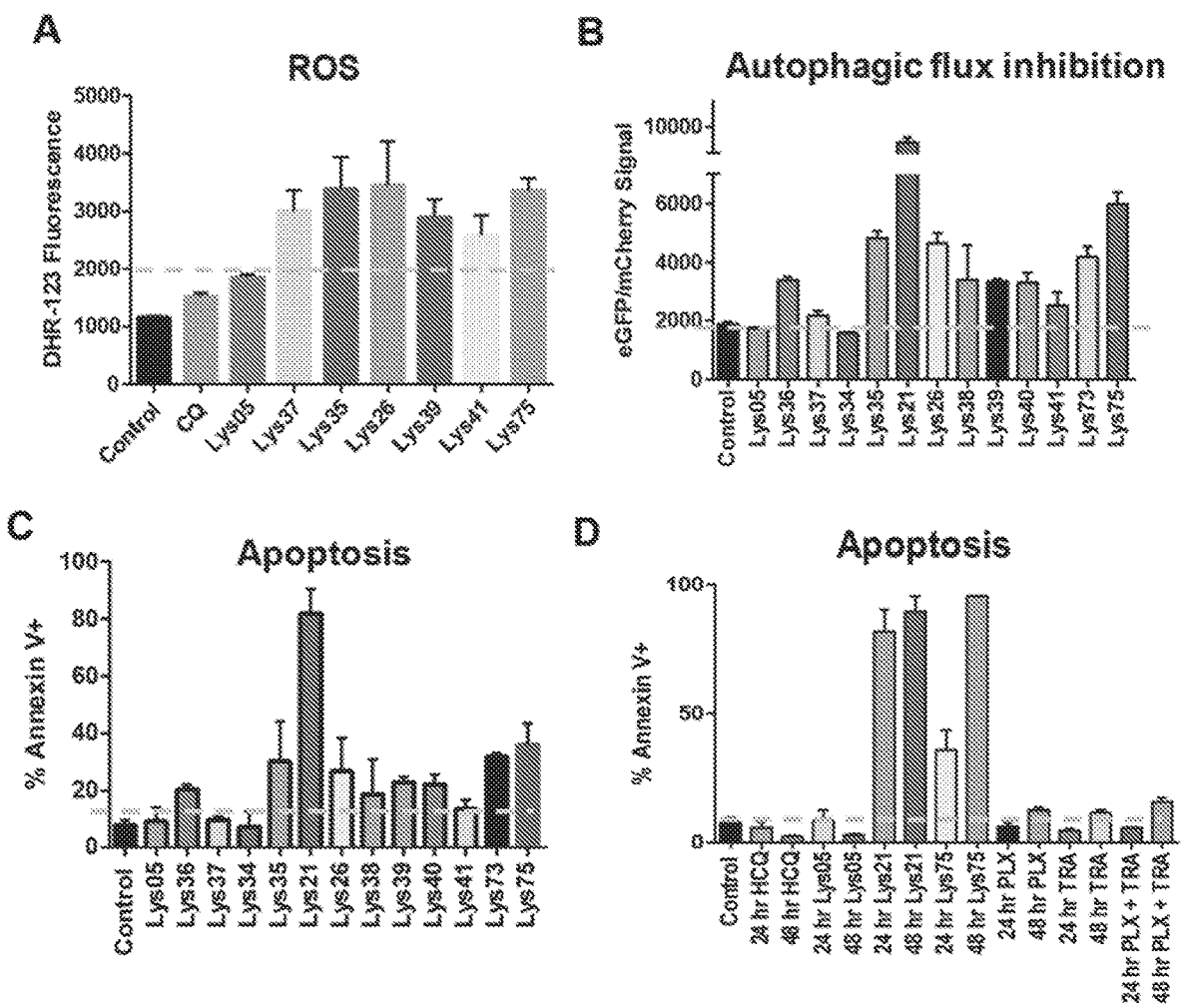
FIG. 8 shows flow cytometry quantification of reactive oxygen species (ROS), autophagy inhibition and apoptosis associated with dimeric CQs with longer linkers. (A) ROS reflected by DHR_123 fluorescence in A375 cells after 24 hours of treatment with 1 uM compound (B) Autophagy inhibition reflected by green/red ratio of A375 mCherry-egfpLC3 cells treated with 1 uM indicated compound for 24 hours. (C) Apoptosis reflected by annexin V detection in A375 cells treated with 1 uM compound at the 24 hours. (D) Apoptosis reflected by annexin V detection in A375 cells treated with indicatd compounds at 3 uM for 24 or 48 hours. PLX: PLX4720; TRA: trametinib.

Longer Linker Compounds are Associated with More Profound Autophagy Modulation, Reactive Oxygen Species (ROS) and Apoptosis As an initial method of determining the effects of the longer linker compounds on autophagic vesicle accumulation, a series of most cytotoxic dimeric CQ's were used to treat 3 different cell lines (1 uM, 24 hours). Cell lysates were collected and immunoblotting against LC3 and actin as performed (FIG. 4). To determine if increased cytotoxicity associated with Lys01 derivatives correlated with more potent inhibition of autophagy, LC3 immunoblotting was performed. LC3 is a ubiquitin-like protein which exists as a unconjugated form (LC3I) or conjugated to AV membranes (LC3II)(23). Quantification of LC3II/actin bands demonstrated that all of the longer linker compounds were superior to Lys05 at modulating LC3II levels. Although there was some variability across melanoma cell lines, in all cases the longest linker compound Lys75 produced the most consistent and substantial increase in the LC3II/actin ration. To confirm that LC3II modulation observed was indeed due to the inhibition of autophagic flux, A375P mCherry-GFP-LC3 cells were used in a high throughput phenotypic screen. In cells expressing this tandem fluorescent reporter construct autophagy induction results in accumulation of red puncta, because the green GFP fluorescence is partially quenched when autophagic vesicles fuse with the lysosomes. In cells where autophagic flux is inhibited distally due to lysosomal impairment, the green signal persists, turning puncta into a yellow color. Lys01-Lys27, HCQ, CQ and doxorubicin which serves as a control were administered to cells in concentrations ranging from 0-10 uM using pinwheel transfer, Operetta confocal imaging allowed image capture for high content analysis (FIG. 5, FIG. 6). Simple analysis of per cell (based on nuclear Hoescht staining) basis demonstrated that at 10 µM concentrations, compounds which had previously been identified as having lower IC50 in viability experiments also produced green/red fluorescent ratios>3.5. Histograms of % cells with green:red ratio>3.5 demonstrates that in some cases lower doses of the compounds also produced this phenotype indicative of effective autophagy inhibition (FIG. 7). Previous studies have demonstrated that CQ derivatives produce ROS in cancer cells. Each of the longer linker Lys01 derivative was superior to Lys05 in inducing ROS (FIG. 8A). Lys26 (closely related to Lys21) and Lys75 produced the highest levels of ROS. Flow cytometry was used to quantify the green/red ration indicative of inhibition of autophagic flux in A375P mCherry-eGFP-LC3 cells treated with longer linker dimeric CQs (FIG. 8B). Again, Lys21 and Lys75 were most effective at inhibiting autophagic flux. Finally, to determine if this inhibition of autophagic flux had a functional consequence of cell death, annexin V which reflects apoptosis was measured in A375 cells treated with compounds. Similar to the results observed with autophgic flux, Lys21 and Lys75 produced the most apoptosis at the 24 hour timepoint (FIG. 8C). To put this degree of apoptosis into clinical context, BRAF mutant melanoma cells were treated with longer linker dimeric CQs or standard of care BRAF, or BRAF (PLX4720) and MEK inhibitor (trametinib). The longer linker Lys01 derivatives produced significantly more apoptosis than clinically approved kinase inhibitors despite equimolar dosing (FIG. 8D).

Dimeric CQ's with Longer Linkers Impair Growth and Invasion of Melanoma in a 3 Dimensional Tissue Like Culture System.

The 3D spheroid model has been used extensively to mimic the tumor microenvironment (Ma et al *Clin Can Research* 2011). Autophagy levels are more reflective of in vivo autophagy dynamics in the 3D models compared to traditional two dimensional cell culture. In this format cancer cells are grown as spheroids and then implanted in a collagen matrix. The spheroids then begin to invade and grow within this tissue microenvironment. Treatment with various longer linker dimeric chloroquines once again demonstrated that Lys75 was the most potent compound at inhibiting growth and invasion of the 3D spheroids (FIG. 9A, B).

Longer Linker Compounds

Figure 13:
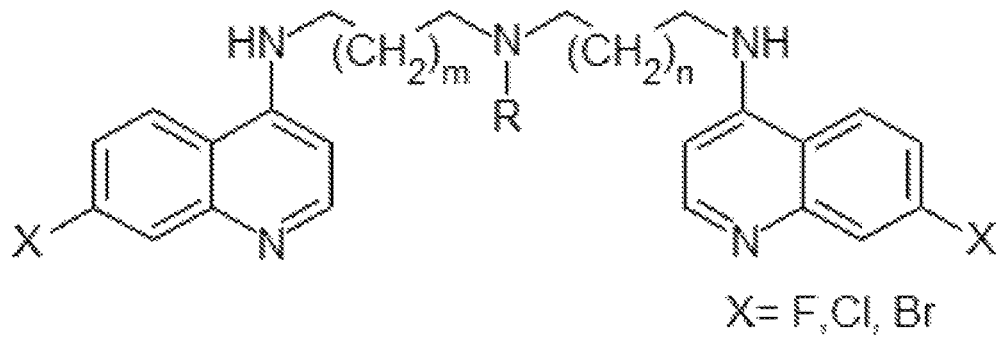
FIG. 13 shows the chemical structures of a number of novel bisaminoquinolines according to the present invention with various halo-substituents (F, Cl, Br) on the 7-position of the quinoline moiety.

To further investigate the role of linker length with regards to potency we prepare a series of compounds with even longer linkers (FIG. 13 Compounds Lys86-Lys97). We also revisit the effects of quinolone ring substitution in the setting of these longer linked compound (FIG. 13).

Summary and Conclusion

Increasing linker length between quinolone rings in dimeric chloroquines significantly improved anti-cancer cytoxicity, ROS production, and autophagy inhibition. Assymetric dimeric chloroquines showed similar anticancer cytotoxicity in 72 hour viability assays to comparable symmetric counterparts. However in the case of Lys21, superior autophagy inhibition and ability to induce apoptosis was observed compared to comparable compounds that were symmetric.

The GI toxicity associated with Paneth cell dysfunction observed at LD30 doses of Lys05, support the mechanism of action of the present invention, and also suggests that colon cancers, which often share features with Paneth cells, may be a tumor type, among others, that may be particularly sensitive to Lys05 and its optimized derivatives. Additional cancers which represent particularly important targets include melanoma, and non-small cell lung cancer, since melanoma cell lines demonstrated the highest difference in sensitivity to Lys01 compared to HCQ, and an EGFR mutated lung cancer cell line demonstrated sensitivity to both HCQ and Lys05. Further mechanistic studies are planned that will potentially identify pharmacodynamics assays that guide drug development. Pharmacokinetic studies are planned in mice to establish initial in vivo profile.

Advantages over other similar technologies: The present invention represents the most potent bisaminoquinoline derivatives reported thus far in cell lines. Other autophagy compounds are not focused on the lysosome as a target and consequently do not evidence the level of activity of compounds according to the present invention.

A. References Cited:
1. Lum J J, DeBerardinis R J, and Thompson C B. Autophagy in metazoans: cell survival in the land of plenty. *Nat Rev Mol Cell Biol.* 2005; 6(6):439-48.

2. Amaravadi R K, and Thompson C B. The roles of therapy-induced autophagy and necrosis in cancer treatment. *Clin Cancer Res.* 2007; 13(24):7271-9.
3. Amaravadi R K, Yu D, Lum J J, Bui T, Christophorou M A, Evan G I, Thomas-Tikhonenko A, and Thompson C B. Autophagy inhibition enhances therapy-induced apoptosis in a Myc-induced model of lymphoma. *J Clin Invest.* 2007; 117(2):326-36.
4. Degenhardt K, Mathew R, Beaudoin B, Bray K, Anderson D, Chen G, Mukherjee C, Shi Y, Gelinas C, Fan Y, et al. Autophagy promotes tumor cell survival and restricts necrosis, inflammation, and tumorigenesis. *Cancer Cell.* 2006; 10(1):51-64.
5. Amaravadi R K. Autophagy-induced tumor dormancy in ovarian cancer. *J Clin Invest.* 2008.
6. Carew J S, Nawrocki S T, Kahue C N, Zhang H, Yang C, Chung L, Houghton J A, Huang P, Giles F J, and Cleveland J L. Targeting autophagy augments the anticancer activity of the histone deacetylase inhibitor SAHA to overcome Bcr-Abl-mediated drug resistance. *Blood* 2007.
7. Degtyarev M, De Maziere A, Orr C, Lin J, Lee B B, Tien J Y, Prior W W, van Dijk S, Wu H, Gray D C, et al. Akt inhibition promotes autophagy and sensitizes PTEN-null tumors to lysosomotropic agents. *J Cell Biol.* 2008; 183(1):101-16.
8. Amaravadi R K, Lippincott-Schwartz J, Yin X M, Weiss W A, Takebe N, Timmer W, Dipaola R S, Lotze M T, and White E. Principles and Current Strategies for Targeting Autophagy for Cancer Treatment. *Clin Cancer Res.* 2011; 17(4):654-66.
9. Rebecca V W, Massaro R R, Fedorenko I V, Sondak V K, Anderson A R, Kim E, Amaravadi R K, Maria-Engler S S, Messina J L, Gibney G T, et al. Inhibition of autophagy enhances the effects of the AKT inhibitor MK-2206 when combined with paclitaxel and carboplatin in BRAF wild-type melanoma. *Pigment Cell Melanoma Res.* 2014; 27(3):465-78.
10. Mahalingam D, Mita M, Sarantopoulos J, Wood L, Amaravadi R, Davis L E, Mita A, Curiel T J, Espitia C M, Nawrocki S T, et al. Combined autophagy and HDAC inhibition: A phase I safety, tolerability, pharmacokinetic, and pharmacodynamic analysis of hydroxychloroquine in combination with the HDAC inhibitor vorinostat in patients with advanced solid tumors. *Autophagy.* 2014; 10(8).
11. Rangwala R, Chang Y C, Hu J, Algazy K, Evans T, Fecher L, Schuchter L, Torigian D A, Panosian J, Troxel A, et al. Combined MTOR and autophagy inhibition: Phase I trial of hydroxychloroquine and temsirolimus in patients with advanced solid tumors and melanoma. *Autophagy.* 2014; 10(8).
12. Rangwala R, Leone R, Chang Y C, Fecher L, Schuchter L, Kramer A, Tan K S, Heitjan D F, Rodgers G, Gallagher M, et al. Phase I trial of hydroxychloroquine with dose-intense temozolomide in patients with advanced solid tumors and melanoma. *Autophagy.* 2014; 10(8).
13. Rosenfeld M R, Ye X, Supko J G, Desideri S, Grossman S A, Brem S, Mikkelson T, Wang D, Chang Y C, Hu J, et al. A phase I/II trial of hydroxychloroquine in conjunction with radiation therapy and concurrent and adjuvant temozolomide in patients with newly diagnosed glioblastoma multiforme. *Autophagy.* 2014; 10(8).
14. Vance D, Shah M, Joshi A, and Kane R S. Polyvalency: a promising strategy for drug design. *Biotechnol Bioeng.* 2008; 101(3):429-34.
15. Shrivastava A, Nunn A D, and Tweedle M F. Designer peptides: learning from nature. *urr Pharm Des.* 2009; 15(6):675-81.
16. Girault S, Grellier P, Berecibar A, Maes L, Lemiere P, Mouray E, Davioud-Charvet E, and Sergheraert C. Antiplasmodial activity and cytotoxicity of bis-, tris-, and tetraquinolines with linear or cyclic amino linkers. *J Med Chem.* 2001; 44(11):1658-65.
17. Vennerstrom J L, Ager A L, Jr., Dom A, Andersen S L, Gerena L, Ridley R G, and Milhous W K. Bisquinolines. 2. Antimalarial N,N-bis(7-chloroquinolin-4-yl)heteroalkanediamines. *J Med Chem.* 1998; 41(22):4360-4.
18. Burnett J C, Schmidt J J, Stafford R G, Panchal R G, Nguyen T L, Hermone A R, Vennerstrom J L, McGrath C F, Lane D J, Sausville E A, et al. Novel small molecule inhibitors of botulinum neurotoxin A metalloprotease activity. *Biochem Biophys Res Commun.* 2003; 310(1):84-93.
19. Hu C, Raja Solomon V, Cano P, and Lee H. A 4-aminoquinoline derivative that markedly sensitizes tumor cell killing by Akt inhibitors with a minimum cytotoxicity to non-cancer cells. *Eur J Med Chem.* 2010; 45(2):705-9.
20. Solomon V R, Hu C, and Lee H. Design and synthesis of chloroquine analogs with anti-breast cancer property. *Eur J Med Chem.* 2010; 45(9):3916-23.
21. McAfee Q, Zhang Z, Samanta A, Levi S M, Ma X H, Piao S, Lynch J P, Uehara T, Sepulveda A R, Davis L E, et al. Autophagy inhibitor Lys05 has single-agent antitumor activity and reproduces the phenotype of a genetic autophagy deficiency. *Proc Natl Acad Sci USA.* 2012; 109(20:8253-8.
22. Cadwell K, Liu J Y, Brown S L, Miyoshi H, Loh J, Lennerz J K, Kishi C, Kc W, Carrero J A, Hunt S, et al. A key role for autophagy and the autophagy gene Atg16l1 in mouse and human intestinal Paneth cells. *Nature.* 2008; 456(7219):259-63.
23. Tanida I, Ueno T, and Kominami E. LC3 conjugation system in mammalian autophagy. *Int J Biochem Cell Biol.* 2004; 36(12):2503-18.

What is claimed is:

1. A compound of Formula IA:

wherein
R$^1$ and R$^{1'}$ are each independently H, F, Cl, Br, I, CN, NO$_2$, optionally substituted C$_1$-C$_6$ alkyl, optionally substituted C$_1$-C$_6$ alkyl, optionally substituted C$_2$-C$_7$ acyl, optionally substituted —(NH)-acyl, or optionally substituted C$_2$-C$_7$ ester;
R and R' are each independently H, a C$_1$-C$_6$ optionally substituted alkyl group, a C$_1$-C$_7$ optionally substituted acyl group, or a C$_2$-C$_7$ optionally substituted carboxy ester group (which forms a urethane group with the nitrogen atom to which R or R' is bonded);
R" is H, Cy$^1$ or (C═O)z-G, where Cy$^1$ is an optionally substituted cycloalkyl, aryl or heteroaryl group G is an optionally substituted C$_0$-C$_{12}$ alkyl, alkene or alkynyl group (wherein optional substituents include a $C_1$-$C_{12}$ alkyl, alkene or alkynyl group substituted by (N—$R^J$)—($C_1$-$C_8$ alkyl, alkene or alkynyl group)$_z$-($Cy^2$)$_x$, where $R^J$ is H or a $C_1$-$C_8$ alkyl, alkene or alkynyl group, z is 0, 1, 2, 3, 4 or 5, x is 0 or 1 and $Cy^t$ is an optionally substituted aryl or heteroaryl group);

$R^M$ is independently at each occurrence H, F, Cl, Br, I, an optionally substituted $C_1$-$C_{12}$ alkyl, alkene, alkynyl or alkoxy group;

Each p in linker group $L^{1A}$ is independently 1, 2, 3, 4, 5, 6, 7, 8, 9, or 10 with the proviso that when R" is H, if one p in linker group $L^{1A}$ is 1, then the other p is 2, 3, 4, 5, 6, 7, 8, 9 or 10; if one p is 2, then the other p is 1, 4, 5, 6, 7, 8, 9, or 10;

and the pharmaceutically acceptable salts, enantiomers, diastereomers, solvates and polymorphs thereof.

2. A compound of Formula IB

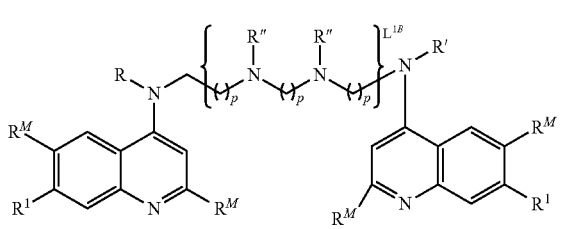

IB wherein $R^1$ and $R^{1'}$ are each independently H, F, Cl, Br, I, CN, $NO_2$, optionally substituted $C_1$-$C_6$ alkyl, optionally substituted O—$C_1$-$C_6$ alkyl, optionally substituted $C_2$-$C_7$ acyl, an optionally substituted —(NH)-acyl, or optionally substituted $C_2$-$C_7$ ester;

R and R' are each independently H, a $C_1$-$C_6$ optionally substituted alkyl group, a $C_1$-$C_7$ optionally substituted acyl group, or a $C_2$-$C_7$ optionally substituted carboxy ester group (which forms a urethane group with the nitrogen atom to which R or R' is bonded);

R" is H, $Cy^1$ or (C=O)z-G, where $Cy^1$ is an optionally substituted cycloalkyl, aryl or heteroaryl group G is an optionally substituted $C_0$-$C_{12}$ alkyl, alkene or alkynyl group (wherein optional substituents include a $C_1$-$C_{12}$ alkyl, alkene or alkynyl group substituted by (N—$R^J$)—($C_1$-$C_8$ alkyl, alkene or alkynyl group)$_z$-($Cy^2$)$_x$, where $R^J$ is H or a $C_1$-$C_8$ alkyl, alkene or alkynyl group, z is 0, 1, 2, 3, 4 or 5, x is 0 or 1 and $Cy^2$ is an optionally substituted aryl or heteroaryl group);

$R^M$ is independently at each occurrence H, F, Cl, Br, I, an optionally substituted $C_0$-$C_{12}$ alkyl, alkene, alkynyl or alkoxy group;

p and p' in linker $L^{1B}$ are each independently 1-10 (1, 2, 3, 4, 5, 6, 7, 8, 9 or 10), and the pharmaceutically acceptable salts, enantiomers, diastereomers, solvates and polymorphs thereof.

3. A compound of Formula IC:

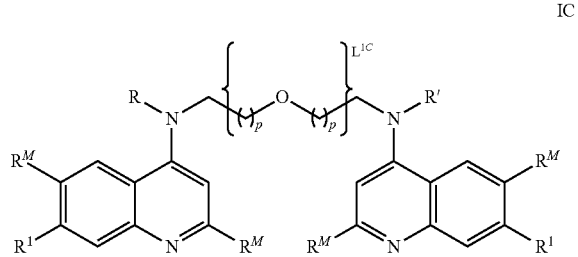

IC wherein $R^1$ and $R^{1'}$ are each independently H, F, Cl, Br, I, CN, $NO_2$, optionally substituted $C_1$-$C_6$ alkyl, optionally substituted O—$C_1$-$C_6$ alkyl, optionally substituted $C_2$-$C_7$ acyl, an optionally substituted —(NH)-acyl, or optionally substituted $C_2$-$C_7$ ester;

R and R' are each independently H, a $C_1$-$C_6$ optionally substituted alkyl group, a $C_1$-$C_7$ optionally substituted acyl group, or a $C_2$-$C_7$ optionally substituted carboxy ester group (which forms a urethane group with the nitrogen atom to which R or R' is bonded);

$R^M$ is independently at each occurrence H, F, Cl, Br, I, an optionally substituted $C_0$-$C_{12}$ alkyl, alkene, alkynyl or alkoxy group;

each p in linker group $L^{1C}$ is independently 1-10 (1, 2, 3, 4, 5, 6, 7, 8, 9 or 10);

and the pharmaceutically acceptable salts, enantiomers, diastereomers, solvates and polymorphs thereof.

4. A compound of Formula ID:

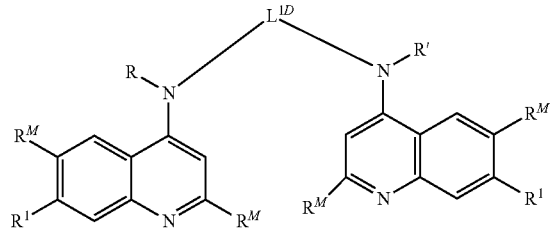

wherein $R^1$ and $R^{1'}$ are each independently H, F, Cl, Br, I, CN, $NO_2$, optionally substituted $C_1$-$C_6$ alkyl, optionally substituted O—$C_1$-$C_6$ alkyl, optionally substituted $C_2$-$C_7$ acyl, optionally substituted —(NH)-acyl, or optionally substituted $C_2$-$C_7$ ester;

R and R' are each independently H, a $C_1$-$C_6$ optionally substituted alkyl group, a $C_1$-$C_7$ optionally substituted acyl group, or a $C_2$-$C_7$ optionally substituted carboxy ester group (which forms a urethane group with the nitrogen atom to which R or R' is bonded), with the proviso that R and R' are not both H;

$R^M$ is independently at each occurrence H, F, Cl, Br, I, an optionally substituted $C_0$-$C_{12}$ alkyl, alkene, alkynyl or alkoxy group;

Linker group $L^{1D}$ is an optionally substituted alkylene group containing from 1-20 methylene groups;

and the pharmaceutically acceptable salts, enantiomers, diastereomers, solvates and polymorphs thereof.

5. A compound of formula IE:

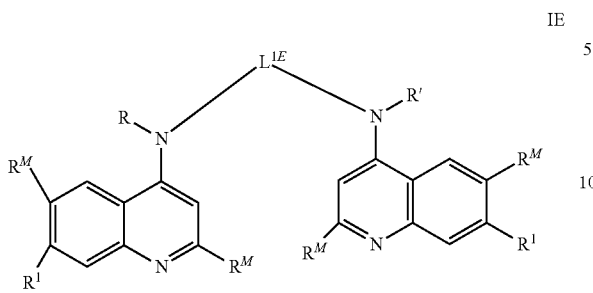

wherein
- $R^1$ and $R^{1'}$ are each independently H, F, Cl, Br, CN, $NO_2$, optionally substituted $C_1$-$C_6$ alkyl, optionally substituted O—$C_1$-$C_6$ alkyl, optionally substituted —(NH)-acyl, optionally substituted $C_2$-$C_7$ acyl or optionally substituted $C_2$-$C_7$ ester that is an oxycarbonyl ester or a carboxyester;
- $R^M$ is independently at each occurrence H, F, Cl, Br, I, an optionally substituted $C_1$-$C_{12}$alkyl, alkene, alkynyl or alkoxy group;
- R and R' are each independently H, a $C_1$-$C_6$ optionally substituted alkyl group, a $C_1$-$C_7$ optionally substituted acyl group, or a $C_2$-$C_7$ optionally substituted carboxy ester group (which forms a urethane group with the nitrogen atom to which R or R' is bonded);
- Linker group $L^{1E}$ is a A-$(CH_2$—$CH_2$—$Z)_n$-A' group wherein at least one of the $CH_2$ groups in $L^{1E}$ is optionally substituted with an optionally substituted $C_1$-$C_6$ alkyl group including a cyclic alkyl group, or at least two methylene groups are optionally substituted with alkylene groups to form an optionally substituted $C_3$-$C_8$ cycloalkyl group, or linker group $L^{1E}$ is a (poly)ethylene glycol group having from 1 to 20 ethylene glycol units, each (poly)ethylene glycol group being optionally substituted at one or both of its distal ends with an A group, or $L^{1E}$ is a linear group containing from 1 to 5 non-contiguous amine groups N—R", each amine group being separated from an adjacent amine group by an alkylene group containing from 1, 2, 3, 4, 5, 6, 7, or 8 methylene groups or an ethylene glycol containing group having from 1 to 6 ethylene glycol units;
- R" is H or an optionally substituted $C_1$-$C_6$ alkyl group or an amine protecting group; each j is independently 1, 2, 3, 4, 5 or 6;
- each n is independently 1, 2, 3, 4, 5, 6, 7, 8, 9 or 10;
- A is absent, C=O or $(CH_2)j$ and A' is C=O or $(CH_2)j$ wherein at least one $CH_2$ group in A or A' is optionally substituted;
- Z is O or N—$R^z$;
- $R^z$ is H or an optionally substituted $C_j$-$C_3$ alkyl group, or a pharmaceutically acceptable salt, enantiomer, diastereomer, solvent or polymorph thereof.

6. The compound according to claim 5 wherein at least two $R^M$ are other than H.

7. The compound according to claim 5 wherein $R^1$ and $R^{1'}$ are each independently H or a halo group.

8. The compound according to claim 5 wherein Linker group $L^{1E}$ is an alkylene group containing from 6 to 20 methylene groups ($C_6$-$C_{20}$ alkylene group).

9. The compound according to claim 5 wherein Linker group $L^{1E}$ is a (poly)ethylene glycol group having from 1 to 20 ethylene glycol units optionally substituted at one or both distal ends of said (poly)ethylene glycol group with an A group.

10. The compound according to claim 5 wherein Linker group $L^{1E}$ is a linear group containing from 1 to 5 non-contiguous amine groups N—R", each amine group being separated from an adjacent amine group by an alkylene group containing 1, 2, 3, 4, 5, 6, 7, or 8 methylene groups or an ethylene glycol containing group containing 1, 2, 3, 4, 5 or 6 ethylene glycol units.

11. A compound that is:

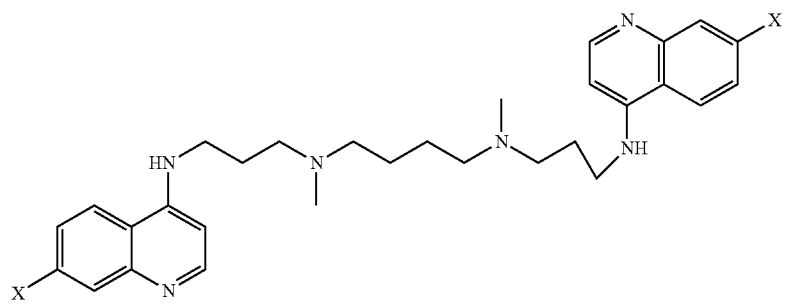

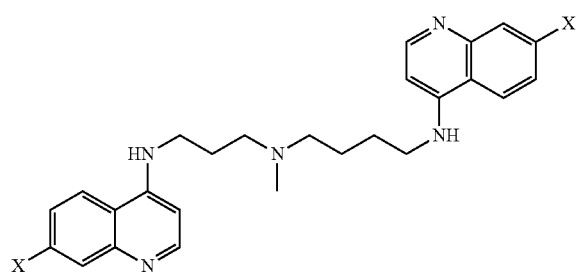

-continued

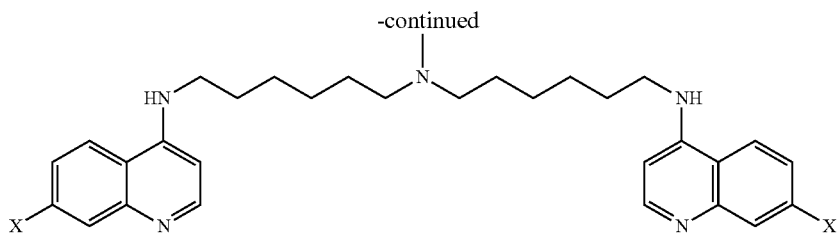

where X is a halogen
or a pharmaceutically acceptable salt thereof, solvate thereof, or polymorph thereof.

12. A compound according to claim 5 wherein $R^1$ and $R^{1'}$ are each Cl, or a pharmaceutically acceptable salt thereof.

13. A pharmaceutical composition comprising a therapeutically effective amount of at least one compound according to claim 1 in combination with a pharmaceutically acceptable carrier, additive or excipient.

14. The composition according to claim 13 comprising a compound according to claim 11.

15. The composition according to claim 14 wherein said compound is:

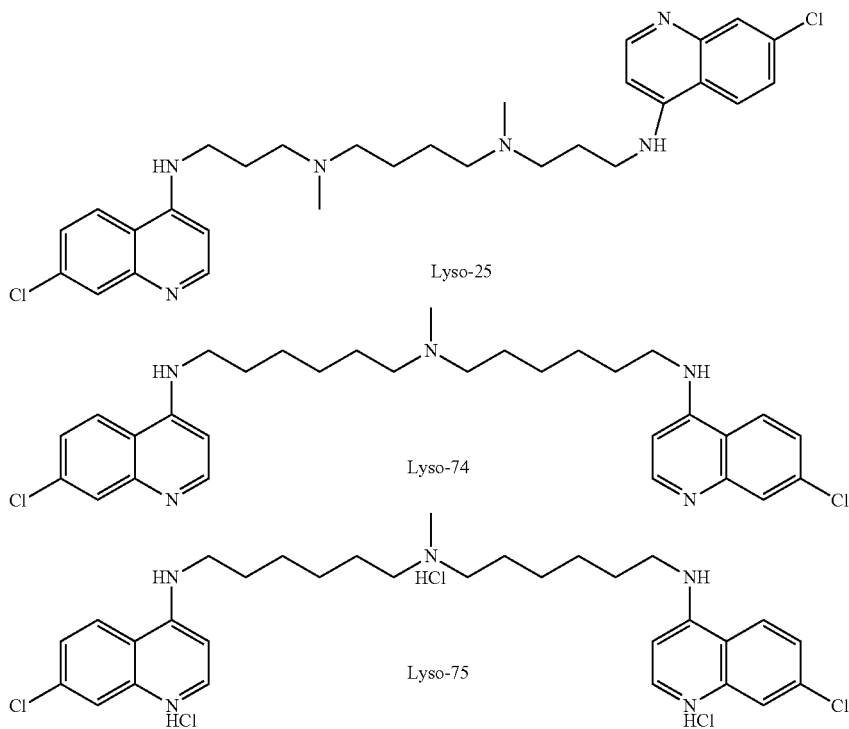

a mixture thereof or a pharmaceutical acceptable salt(s) thereof.

16. The composition according to claim 13 further comprising an effective amount of at least one additional anticancer agent.

17. The composition according to claim 16 wherein said anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PT3 kinase inhibitors, an AKT inhibitor, a JAK/STAT inhibitor, a checkpoint-1 or 2 inhibitor, a focal adhesion kinase inhibitor, a Map kinase (mek) inhibitor, a VEGF trap antibody or a mixture thereof.

18. The composition according to claim 16 wherein said anticancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-1 10, BIO 140, CC 8490, cilengitide, gimatecan, IL13-PE38QQR, INO 1001, IPdR, KRX-0402, lucanthone, LY317615, neuradiab, vitespan, Rta 744, Sdx 102, talampanel, atrasentan, Xr 311, romidepsin, ADS-100380, sunitimb, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl) ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1Cl, CH1R-258, 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-$NH_2$ acetate[$C_{59}H_{84}N_{18}O_{14}$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, F-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovasta BMS-275291, squalamine, endostatin, SU5416, SI J 6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PT 787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib and mixtures thereof.

19. A method of inhibiting autophagy in a biological system in which inhibition of autophagy is desired, said method comprising exposing said biological system to an effective amount of at least one compound according to claim 1.

20. A method of treating cancer in a patient wherein the cancer is mediated by autophagy comprising administering to said patient an effective amount of at least one composition according to claim 13.

21. The method according to claim 20, wherein said cancer is metastatic; or wherein said cancer is recurrent; or wherein said cancer is a drug-resistant cancer.

22. The method according to claim 20, wherein said cancer is a carcinoma, cancer of the esophagus, head, kidney, liver, lung, nasopharyngeal, neck, ovary, pancreas, prostate, and stomach; a leukemia, a malignant lymphoma, a malignant melanoma; myeloproliferative diseases; a sarcoma, a tumor of the central nervous system, a germ-line tumor, lung cancer, ovarian cancer, testicular cancer, thyroid cancer, astrocytoma, esophageal cancer, pancreatic cancer, stomach cancer, liver cancer, colon cancer, melanoma, or a mixed type of neoplasia.

23. The method according to claim 22, wherein said leukemia is acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia or stem cell leukemia.

24. The method according to claim 22, wherein said lymphoma is Burkitt's lymphoma, Non-Hodgkin's lymphoma or B-cell lymphoma;

wherein said sarcoma is Ewing's sarcoma, hemangiosarcoma, Kaposi's sarcoma, liposarcoma, myosarcomas, peripheral neuroepithelioma or synovial sarcoma;

wherein said tumor of the central nervous system is a glioma, astrocytoma, oligodendroglioma, ependymoma, glioblastoma, neuroblastoma, ganglioneuroma, ganglioglioma, medulloblastoma, pineal cell tumor, meningioma, meningeal sarcoma, neurofibroma, or Schwannoma;

wherein said germ-line tumor is bowel cancer, breast cancer, prostate cancer, cervical cancer or uterine cancer;

wherein said lung cancer is small cell lung cancer, mixed small cell and non-small cell cancer, pleural mesothelioma, metastatic pleural mesothelioma, small cell lung cancer or non-small cell lung cancer; or wherein said mixed neoplasia is carcinosarcoma and Hodgkin's disease and said tumors of mixed origin is Wilms' tumor and teratocarcinomas.

25. The method according to claim 22, wherein said cancer is ovarian, breast, colon, head and neck, medulloblastoma or B-cell lymphoma, melanoma or non-small cell lung cancer.

26. A compound that is:

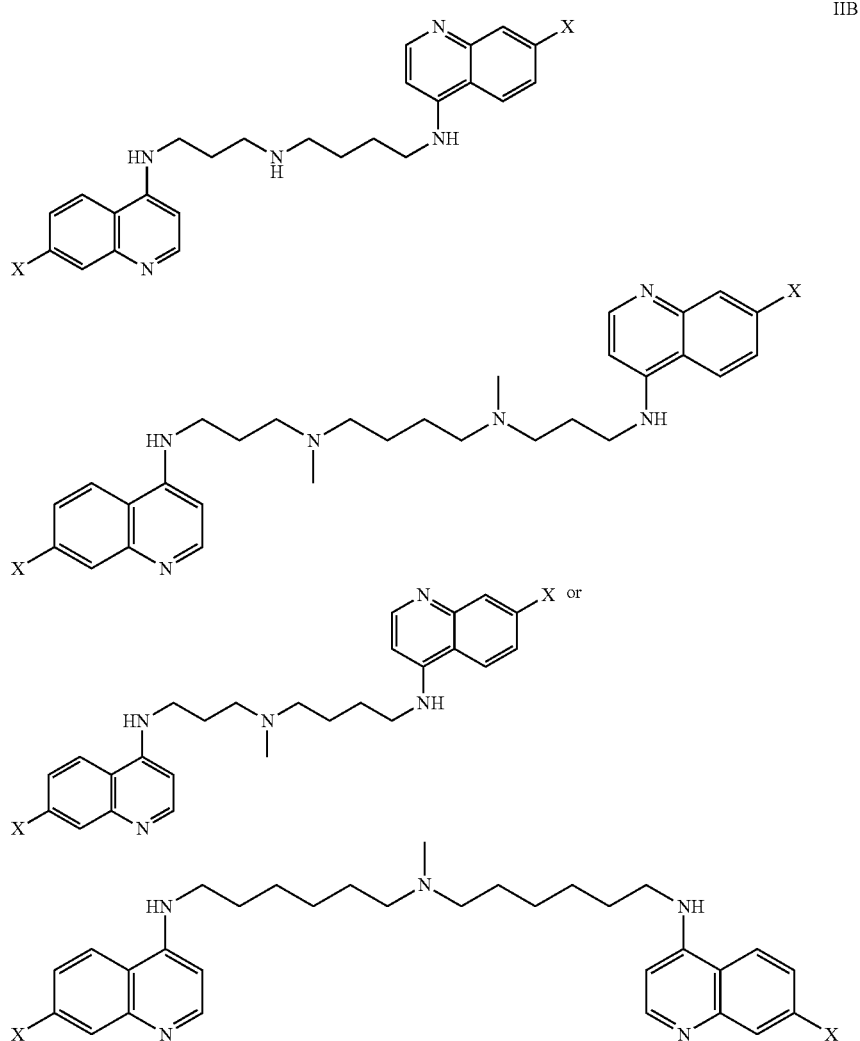

IIB wherein X is F, or a pharmaceutically acceptable salt, solvate, or polymorph thereof.

27. The compound according to claim 7, wherein the halo group is F or Cl.

28. The compound according to claim 5, wherein n is 0, $R^1$ and $R^{1'}$ are $(CH_2)_j$, where j is at least 1 and at least one $CH_2$ group is substituted with a $C_1$-$C_3$ alkyl group that is optionally substituted with one or two hydroxyl groups or one, two, or three halo groups.

29. The compound according to claim 5, wherein at least one $CH_2$ group in A or A' is substituted with a $C_1$-$C_3$ alkyl group which is itself optionally substituted.

30. The compound according to claim 11, wherein X is F or Cl.

* * * * *